United States Patent
Marineo

(10) Patent No.: US 8,380,317 B2
(45) Date of Patent: Feb. 19, 2013

(54) APPARATUS AND METHOD FOR QUICK PAIN SUPPRESSION

(76) Inventor: Giuseppe Marineo, Rome (IT)

( * ) Notice: Subject to any disclaimer, the term of this patent is extended or adjusted under 35 U.S.C. 154(b) by 1087 days.

(21) Appl. No.: 12/080,434

(22) Filed: Apr. 2, 2008

(65) Prior Publication Data

US 2009/0076568 A1 Mar. 19, 2009

Related U.S. Application Data

(63) Continuation of application No. PCT/IT2007/000647, filed on Sep. 18, 2007.

(51) Int. Cl.
*A61N 1/36* (2006.01)
(52) U.S. Cl. .......................................................... 607/46
(58) Field of Classification Search .............. 607/2, 46, 607/66, 68–73
See application file for complete search history.

(56) References Cited

U.S. PATENT DOCUMENTS

| | | | | |
|---|---|---|---|---|
| 4,699,143 | A * | 10/1987 | Dufresne et al. ................. | 607/46 |
| 5,891,182 | A * | 4/1999 | Fleming ............................ | 607/50 |
| 7,551,956 | B2 * | 6/2009 | Osorio et al. .................... | 600/545 |
| 2007/0293818 | A1 | 12/2007 | Stout et al. | |
| 2007/0293917 | A1 | 12/2007 | Thompson et al. | |
| 2007/0293918 | A1 | 12/2007 | Thompson et al. | |

OTHER PUBLICATIONS

Serafini, et al; "Scrambler Therapy: a new option in neuropathic pain treatment?"; The Pain Clinic, vol. 12, No. 4, pp. 287-298 (2000).
Marineo, et al; "Artificial neurons in oncological pain: the potential of Scrambler Therapy to modify a biological information"; International Congress Series 2358 (2003); vol. 1255, pp. 381-388.
Kumazawa, T; "The Polymodal Receptor: Bio-warning and Defense System"; Progress in Brain Research, vol. 113, 1996.
Park, H. et al.; "Design and Implementation of Wireless Transcutaneous Electrical Nerve Stimulator (TENS) for SMart Phone"; Electronics Express, vol. 6, No. 22, 1587-1594; 2009.
Beissner, F., et al.; "Quick Discrimination of Adelta and C. Fibe3r Mediated Pain Based on Three Verbal Descriptors"; http://www.ncbi.nlm.nih.gov/pmc/articles/PMC2944851/?tool+pmcent; 2012.

* cited by examiner

Primary Examiner — George Evanisko
(74) Attorney, Agent, or Firm — Edwards Wildman Palmer LLP; Barry Kramer; George N. Chaclas

(57) ABSTRACT

Apparatus and methods for quick acute and chronic pain suppression, particularly useful and effective towards high-grade pains and/or pains resistant to other analgesic drugs such as opiates. One apparatus and method generate synthetic "non-pain" information strings of great clinical effectiveness, allowing high reproducibility of the clinical result. Synthesis of the strings occurs by combining novel geometries of complex waveforms in a sequence, perceived as "self" and "non-pain" by the CNS.

29 Claims, 41 Drawing Sheets

APPARATUS AND METHOD FOR QUICK PAIN SUPPRESSION

CROSS-REFERENCE TO RELATED APPLICATION

This application claims the benefit of and priority to PCT Patent Application No. PCT/IT2007/000647, filed Sep. 18, 2007, which is incorporated herein by reference.

BACKGROUND OF THE INVENTION

1. Field of the Invention

The present invention refers to an apparatus and a method for quick acute and chronic pain suppression, particularly useful and effective towards high-grade pains and/or pains resistant to other analgesic drugs such as opiates.

2. Background of the Related Art

Pain therapy by electrostimulation is practiced with apparatuses normally producing wave trains ranging from 5 to 100 Hz, with variable duty cycle, at times implementing automatic frequency and amplitude scanning. These apparatuses are generally referred to as TENS when used in a non-invasive manner with surface electrodes, or as implanted electric stimulators when they are invasive. With reference to substantiated scientific literature, this kind of electroanalgesia works only with some types of pain, yet almost never or with largely unsatisfactory and unforeseeable results in high-grade chronic pain, neuropathic pain, pain non-responsive to morphine and/or derivatives thereof.

Moreover, these electric stimulations have a heuristic base of scientific and technological development; in fact, in the scientific literature, no commonly accepted explanation exists for the biological mechanisms of the analgesic effect that is produced in some cases. One of the theories, still erroneously considered as plausible to date, is that the electric stimulus fosters endorphin production, and endorphins, in turn, are accountable for the analgesia. Actually, targeted and published clinical research experimentally invalidated this explanation attempt, leaving this method to empiricism. More reliable is the explanation of operation according to Gate Control theory. Accordingly, these electric stimulations are deemed to have an inhibiting function on painful stimulus transmission, by blocking electric-type nerve conduction.

Ultimately, though using electronic technologies, the operation principle does not diverge much from the first attempts at electroanalgesia, historically ascribable to Hippocrates, who used torpedo fish to cure gout pains.

In preceding studies, the problem of oncological pain and that of high-grade chronic pain non-responsive to protocols have been specifically dealt with. These studies have led to the development of an "artificial neuron" able to generate "non-pain" information strings. The artificial bioinformation, by modulating suitable electric potentials carried into the nerve network by surface electrodes, overlaps pain-coding endogenous information, attaining a powerful analgesic effect.

Italian Patent N° 1324899, to the same Inventor, begins to introduce the concepts of a so-called "Scrambler Therapy", based on the concept of synthetic "non-pain" information for therapeutic purposes. The patent relates to the manufacture of an apparatus able to generate an "artificial neuron" allowing concrete use of this theoretical research and the subsequent technological development in clinical practice. Neuronal synthesis used in Italian Patent N° 1324899 yielded waveform geometries quite similar to action potentials produced by human nerve cells (see FIG. 1), organized according to pre-programmed sequences that achieved a concrete result in terms of analgesic effect.

However, subsequent clinical testing of the neuronal synthesis used in Italian Patent N° 1324899 exhibited some limitations, both in the method and in the hardware implementation of the apparatus, which entailed a less than satisfactory efficiency from the standpoint of reproducibility of clinical data, data that was operator-dependent, and in the difficulties encountered when treating more complex polyneuropathy cases, which appeared hardly manageable and rapidly recurring. Moreover, stimulation perception in some patients who were more sensitive, also due to neuropathic damage, was hardly tolerable. This compliance problem increased when treating particularly sensitive zones, such as the face, or specific regions of the body very rich in nerve terminations.

Synthesis was carried out by setting a string comprised of n action potentials of alike geometry, imitating that typical of nerve cells to which a control algorithm subtracted, in determined points, variable blocks of individual potentials, in order to create the required synthetic information in the form of strings. Such a procedure, initially being of a survey type, was mainly aimed at replacing the "pain" information with a bland nociception one; this to be sure to fall within information that the Central Nervous System (hereinafter, CNS) might easily recognize as "self", therefore assessing with greater ease the exactness of the theoretical premise, reducing experimental variability.

This resulted in an extremely compressed dynamics of the putative "non-pain" synthetic information, as well as compressed was the ability to recruit polymodal receptors.

SUMMARY OF THE INVENTION

Hence, an object of the present technology is to overcome the drawbacks mentioned above with reference to the known art, by providing an apparatus for quick pain suppression, including a main module comprising data storage and processing means, said data storage including first parameters ($V_i$) identifying a set of primitive waveforms (S00-S15), each primitive waveform ($S_i$) having a periodic and predetermined pattern over time and second parameters (T-pack$_i$, Freq$_i$, T-slot$_i$) associable with each of said primitive waveforms ($S_i$). The data storage and processing means are able to process a data set ($B_i$) identifying a sequence (S) consisting of one or more of said primitive waveforms ($S_i$) in a time sequence, each of the primitive waveforms of the sequence (S) being processed on the basis of one or more of said second parameters (T-pack$_i$, Freq$_i$, T-slot$_i$). The apparatus also includes a synthesizer module comprising means for generating an electric output signal corresponding to said sequence (S) and one or more channel modules (Ch$_k$) comprising means for applying said electric output signal to a patient's body.

Further, another object of the present technology is to provide a definition of one or more waveforms to be made and used for generating an electric signal in a therapy for quick pain suppression.

Still further, another object of the present invention is a method for generating an electric signal to be used in a therapy for quick pain suppression.

The present technology, by overcoming the mentioned problems of the known art, entails several evident advantages. One advantage lies in that the outcome of this inventive process is the generation of synthetic "non-pain" information strings of great effectiveness, capable of allowing a high reproducibility of the clinical outcome.

Known-art limitations were overcome by restructuring the geometries of primitive waveforms, in order to construct different and more complex dynamic "non-pain" information, jointly with the need to engage a greater number of nerve fibres, especially the polymodal ones, intrinsically able to carry a wider dynamic of non-strictly nociceptive information, therefore also able to establish a greater patient compliance.

In one embodiment, the method of widening the variability of "non-pain" synthetic information entails the need to use, for a dynamic management of the novel and different waveform geometries (constituting a base comparable to "letters of the alphabet" of the synthetic information with a wider "non-pain" variability), novel control algorithms for the definitive assembly into dynamic strings, i.e., information more complex than the individual waveforms.

A further advantage attained is an increase in patient compliance. With the preceding known-art system, the use of substitutive information mainly based on bland nociception synthesis, especially in particularly sensitive persons, created a certain stress and a state of apprehension for fear of feeling pain grow or receiving "jolts" during the treatment. Replacement of this information with other information always perceived as "self" and "non-pain" by the CNS, instead produced in treated patients opposite emotional responses, in some cases also described as: "sensations difficult to describe, but anyhow very pleasant".

Therefore, the outcome of this inventive process is the generation of synthetic "non-pain" information strings of great clinical effectiveness, not merely in immediate analgesia, but also in medium and long-term effects, and allows high reproducibility of the result for damage typology, as well as a sensible increase in the compliance of patients subjected to therapy.

A further advantage of the present technology is making less critical the use of the method in clinical practice, thanks to the increase in the likelihood of recruiting groups of fibres involved in the carrying of synthetic "non-pain" information, and therefore to a less critical selection of surface receptors useful to carry the synthetic "non-pain" information. The studies and testing carried out, whose results are summarised in the graphs of FIGS. 12A to 12C, illustrate the effectiveness of the subject technology, which certainly will become the basis of new technologies used for pain control by means of antagonist synthetic information.

It should be appreciated that the present technology can be implemented and utilized in numerous ways, including without limitation as a process, an apparatus, a system, a device, a method for applications now known and later developed or a computer readable medium.

BRIEF DESCRIPTION OF THE DRAWINGS

Other advantages, features and the operation modes of the present invention will be made apparent in the following detailed description of an embodiment thereof, given by way of example and not for limitative purposes. Reference will be made to the figures of the annexed drawings, wherein.

DETAILED DESCRIPTION OF PREFERRED EMBODIMENTS

Figure 1:
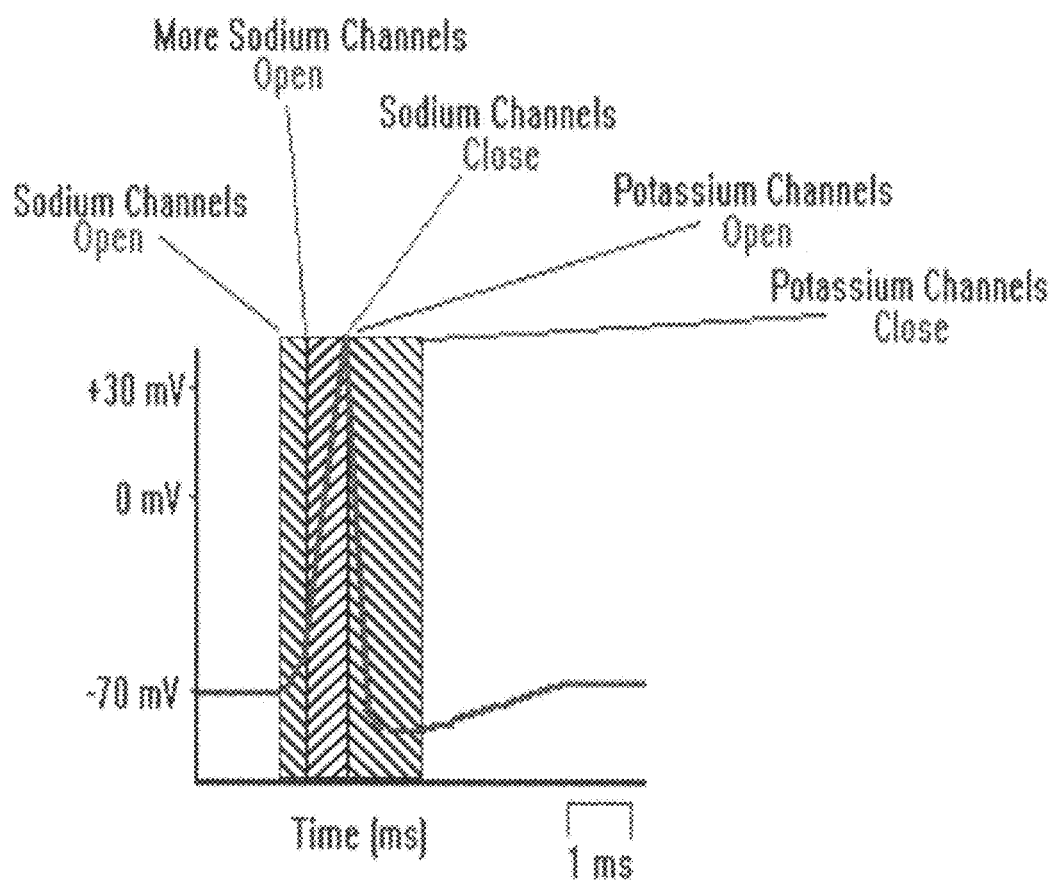
FIG. 1 shows a typical action potential produced by human nerve cells.

The present invention overcomes many of the prior art problems associated with managing pain. The advantages, and other features of the technology disclosed herein, will become more readily apparent to those having ordinary skill in the art from the following detailed description of certain preferred embodiments taken in conjunction with the drawings which set forth representative embodiments of the present invention and wherein like reference numerals identify similar structural elements.

The present invention is based on the following theoretical observation. As it is known, the "pain system" is characterized by a high level of information content, which per se forms its essence. The data of interest taken into account here is the central role of control of "pain" information as to the chemico-structural variations of the pain system on the whole, and in its varied clinical manifestations.

Therefore, according to the present technology, it is deemed possible to control the lower levels of complexity of the pain system, i.e., the biochemical ones, by manipulating at higher levels of complexity (the bioelectric ones generated by nerve cells) the associated "information" variable alone, which in these levels of emerging properties is easily treatable by coding electric potentials into synthesis of waveforms having variable geometry and dynamic assembly structure, with informative functionality analogous to that peculiar to nerve cells.

Therefore, the present invention is carried out by manipulating the endogenous "pain" information, replacing it with a synthetic, yet recognized as "self" by the body, "non-pain" one.

From an informative standpoint, the geometry of the individual primitive waveforms (see FIGS. 2A to 2P) substantially represents an alphabet of "letters" that, when dynamically assembled into strings of variable length and content, constructs the equivalent of plural synthetic "non-pain" information, which the nervous system recognizes as "self" once carried therein.

The synthetic information is able to overmodulate the endogenous pain information, attaining as a clinical effect the immediate disappearance of perception of pain; this regardless of pain intensity, frequency, benign or oncological typology, presence of neuropathic damage, resistance to opiates or to other forms of electroanalgesia.

By precisely selecting the geometry of the primitive waveforms and applying the waveforms in a specific sequence manner, excellent results can be accomplished.

It is also easy to imagine that, in principle, synthesis options are substantially infinite, as there is no general rule such waveforms have to meet. Therefore, the selection according to the present technology was carried out through the several studies and clinical testing performed therefor.

Therefore, since these are synthetic waveforms not simply describable by mathematic models, hereinafter there will be described a set of primitive waveforms (S00-S15) used on the basis of respective first parameters $V_i$ identifying them, in particular of their respective amplitude values, and used just for the synthesis. Each primitive waveform has a periodic and predetermined pattern over time. This, in association to a definite time basis that will be pointed out, allows an exact reconstruction thereof.

In the following Table 1 there are reported the amplitude values, expressed in the hexadecimal system, used for waveform synthesis.

According to a preferred embodiment of the present technology, each individual primitive waveform $S_i$ is numerically represented by a vector $V_i$ of 64 8-bit values.

TABLE 1

| Primitive waveform | vector $V_i$ of amplitude values (i = 0 . . . 15) |
|---|---|
| S00 | B6 FE FE FE FE FE FE FE FE FE FE FE FE FE EC DA C8 B6 A4 92 80 00 20 40 60 6E 80 80 80 80 80 80 80 80 80 80 80 80 80 80 80 80 80 80 80 80 80 80 80 80 80 80 80 80 80 80 80 80 80 80 80 80 80 80 |
| S01 | 81 B6 FE FE FE FE FE FE FE FE FE FE FE FE FE FE FE FE FE FE FA EC DE D0 C2 B4 A6 9A 8E 00 20 40 60 6E 80 80 80 80 80 80 80 80 80 80 80 80 80 80 80 80 80 80 80 80 80 80 80 80 80 80 80 80 80 80 |
| S02 | 81 AA D4 FE FE FE FE FE FE FE FE FE FE FE FE FE FE FE FE FE FE FE FE FE F0 E2 D4 C6 B8 AA 9C 8E 80 00 20 40 60 6E 80 80 80 80 80 80 80 80 80 80 80 80 80 80 80 80 80 80 80 80 80 80 80 80 80 80 |
| S03 | 81 AA D4 FE FE FE FE FE FE FE FE FE FE FE FE FE FE FE FE FE FE FE FE FE F5 EC E3 DA D1 C8 BF B6 AD A5 9B 92 80 00 20 40 60 6E 80 80 80 80 80 80 80 80 80 80 80 80 80 80 80 80 80 80 80 80 80 80 |
| S04 | B6 FE FE FE FE FE FE FE FE FE FE FE FE FE EC DA C8 B6 A4 92 80 00 10 20 30 40 60 70 80 80 80 80 80 80 80 80 80 80 80 80 80 80 80 80 80 80 80 80 80 80 80 80 80 80 80 80 80 80 80 80 80 80 80 80 |
| S05 | 81 B6 FE FE FE FE FE FE FE FE FE FE FE FE FE FE FE FE FE FE FA EC DE D0 C2 B4 A6 9A 8E 00 10 20 30 40 60 70 80 80 80 80 80 80 80 80 80 80 80 80 80 80 80 80 80 80 80 80 80 80 80 80 80 80 80 80 |
| S06 | 81 AA D4 FE FE FE FE FE FE FE FE FE FE FE FE FE FE FE FE FE FE FE FE FE F0 E2 D4 C6 B8 AA 9C 8E 80 00 10 20 30 40 60 70 80 80 80 80 80 80 80 80 80 80 80 80 80 80 80 80 80 80 80 80 80 80 80 80 |
| S07 | 81 AA D4 FE FE FE FE FE FE FE FE FE FE FE FE FE FE FE FE FE FE FE FE FE F5 EC E3 DA D1 C8 BF B6 AD A5 9B 92 80 00 10 20 30 40 60 70 80 80 80 80 80 80 80 80 80 80 80 80 80 80 80 80 80 80 80 80 |
| S08 | B6 FE FE FE FE FE FE FE FE FE FE FE FE FE EC DA C8 B6 A4 92 80 00 04 08 0C 10 16 1C 22 28 2E 34 3A 40 50 60 70 78 80 80 80 80 80 80 80 80 80 80 80 80 80 80 80 80 80 80 80 80 80 80 80 80 80 80 |
| S09 | 81 B6 FE FE FE FE FE FE FE FE FE FE FE FE FE FE FE FE FE FE FA EC DE D0 C2 B4 A6 9A 8E 00 04 08 0C 10 16 1C 22 28 2E 34 3A 40 50 60 70 78 80 80 80 80 80 80 80 80 80 80 80 80 80 80 80 80 80 80 |
| S10 | 81 AA D4 FE FE FE FE FE FE FE FE FE FE FE FE FE FE FE FE FE FE FE FE FE F0 E2 D4 C6 B8 AA 9C 8E 80 00 04 08 0C 10 16 1C 22 28 2E 34 3A 40 50 60 70 78 80 80 80 80 80 80 80 80 80 80 80 80 80 80 |
| S11 | 81 AA D4 FE FE FE FE FE FE FE FE FE FE FE FE FE FE FE FE FE FE FE FE FE F5 EC E3 DA D1 C8 BF B6 AD A5 9B 92 80 00 04 08 0C 10 16 1C 22 28 2E 34 3A 40 50 60 70 78 80 80 80 80 80 80 80 80 80 80 |
| S12 | B6 FE FE FE FE FE FE FE FE FE FE FE FE FE EC DA C8 B6 A4 92 89 00 05 09 0E 18 1E 20 22 28 2E 34 3A 40 49 52 5B 64 6D 77 7F 80 80 80 80 80 80 80 80 80 80 80 80 80 80 80 80 80 80 80 80 80 80 80 |
| S13 | 81 B6 FE FE FE FE FE FE FE FE FE FE FE FE FE FE FE FE FE FE FA EC DE D0 C2 B4 A6 9A 8E 00 05 09 0E 18 1E 20 22 28 2E 34 3A 40 49 52 5B 64 6D 77 7F 80 80 80 80 80 80 80 80 80 80 80 80 80 80 80 |
| S14 | 81 AA D4 FE FE FE FE FE FE FE FE FE FE FE FE FE FE FE FE FE FE FE FE FE F0 E2 D4 C6 B8 AA 9C 8E 80 00 05 09 0E 18 1E 20 22 28 2E 34 3A 40 49 52 5B 64 6D 77 7F 80 80 80 80 80 80 80 80 80 80 80 |
| S15 | 81 AA D4 FE FE FE FE FE FE FE FE FE FE FE FE FE FE FE FE FE FE FE FE FE F5 EC E3 DA D1 C8 BF B6 AD A5 9B 92 80 00 05 09 0E 18 1E 20 22 28 2E 34 3A 40 49 525B 64 6D 77 7F 80 80 80 |

Figure 2A:
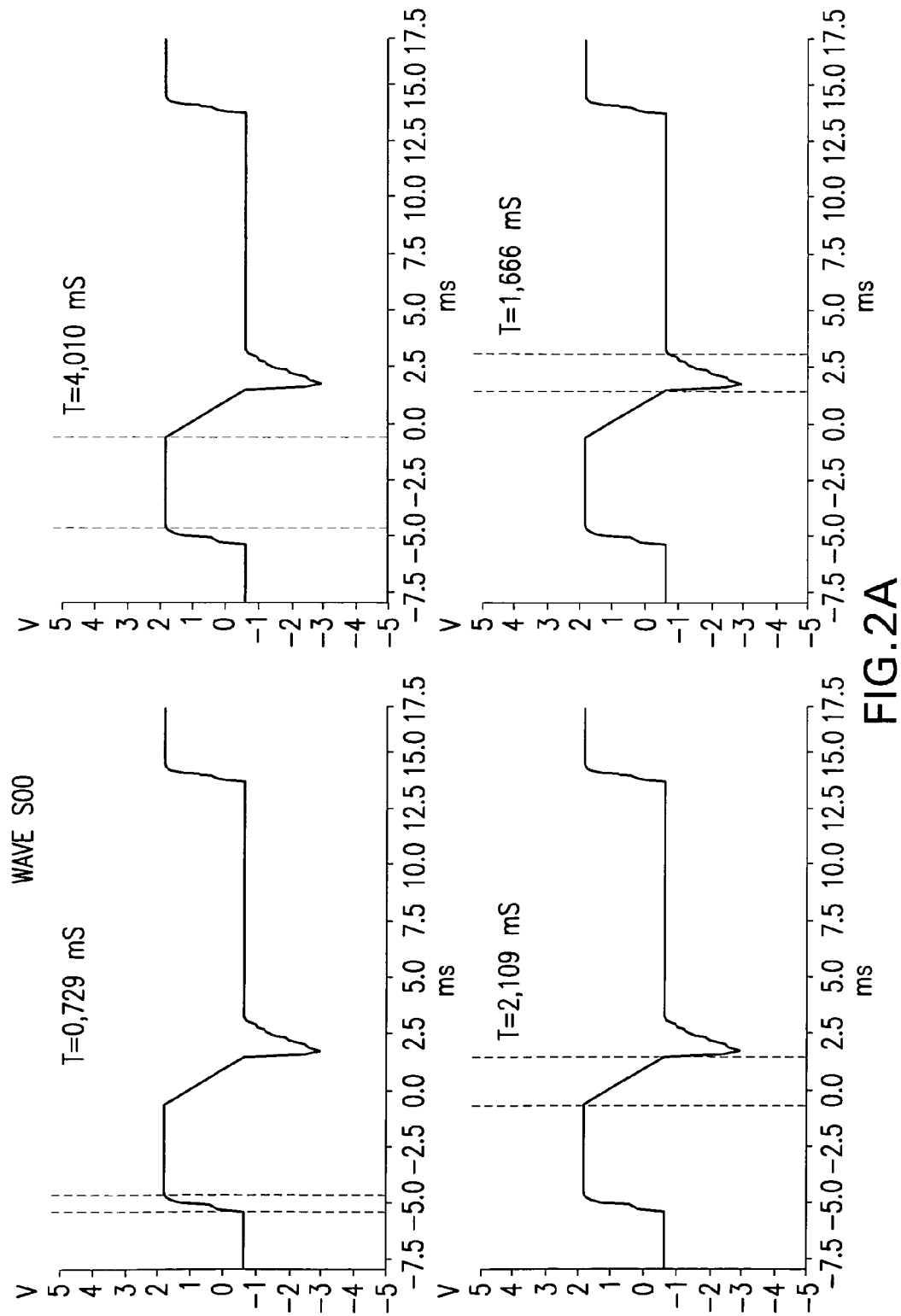
FIGS. 2A to 2P are graphs depicting the pattern over time of the primitive waveforms according to the present invention.
Figure 2B:
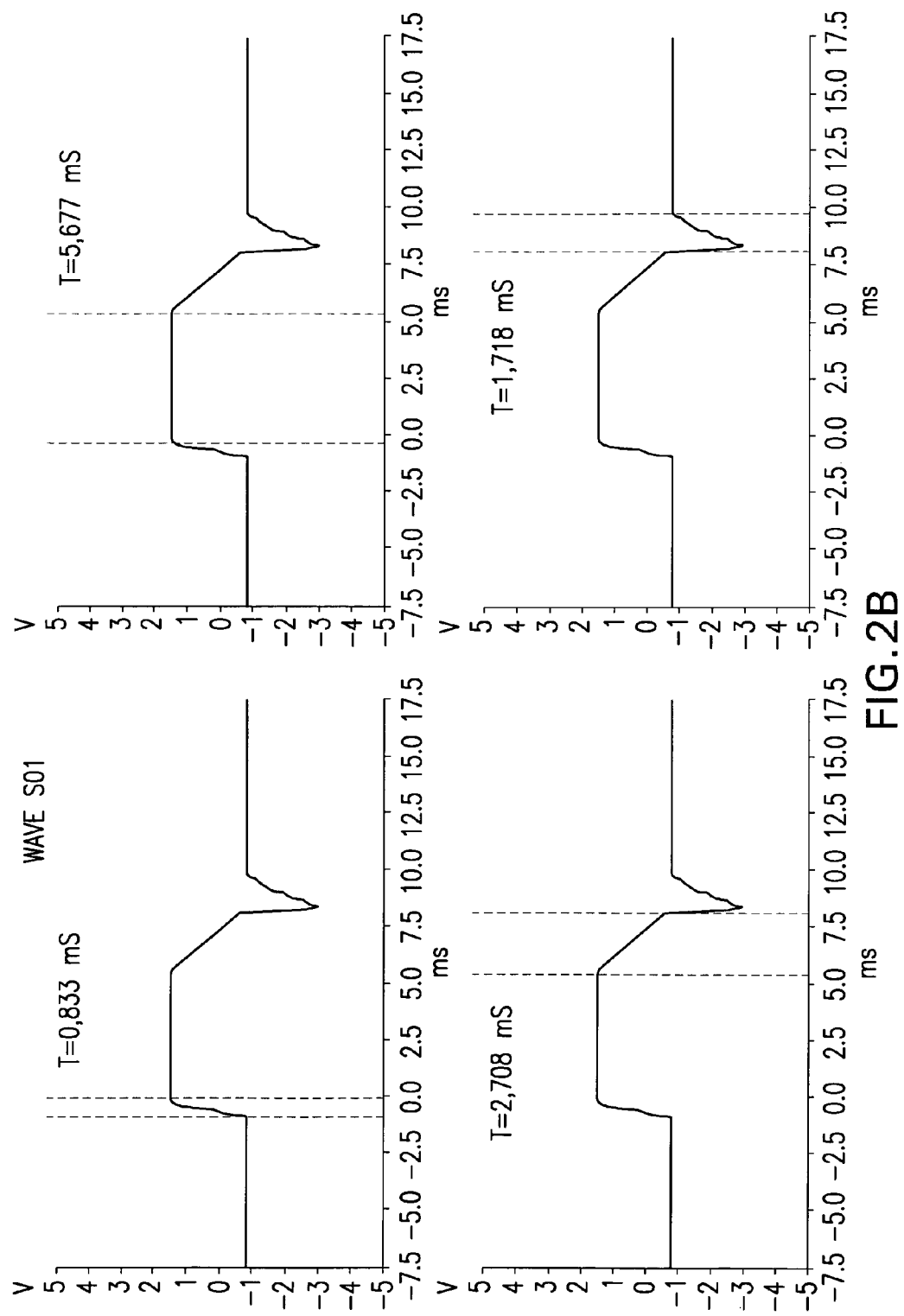
Figure 2C:
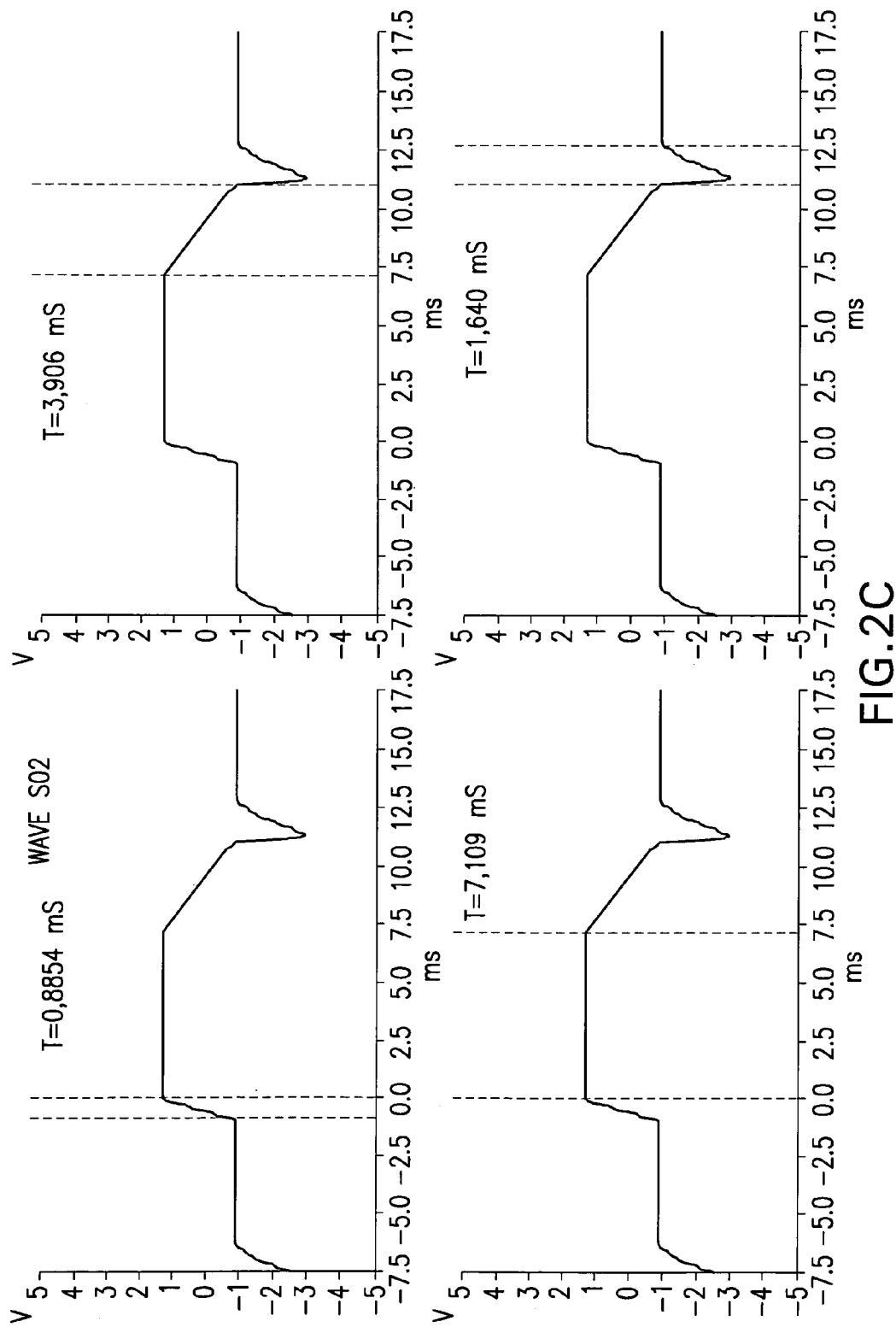
Figure 2D:
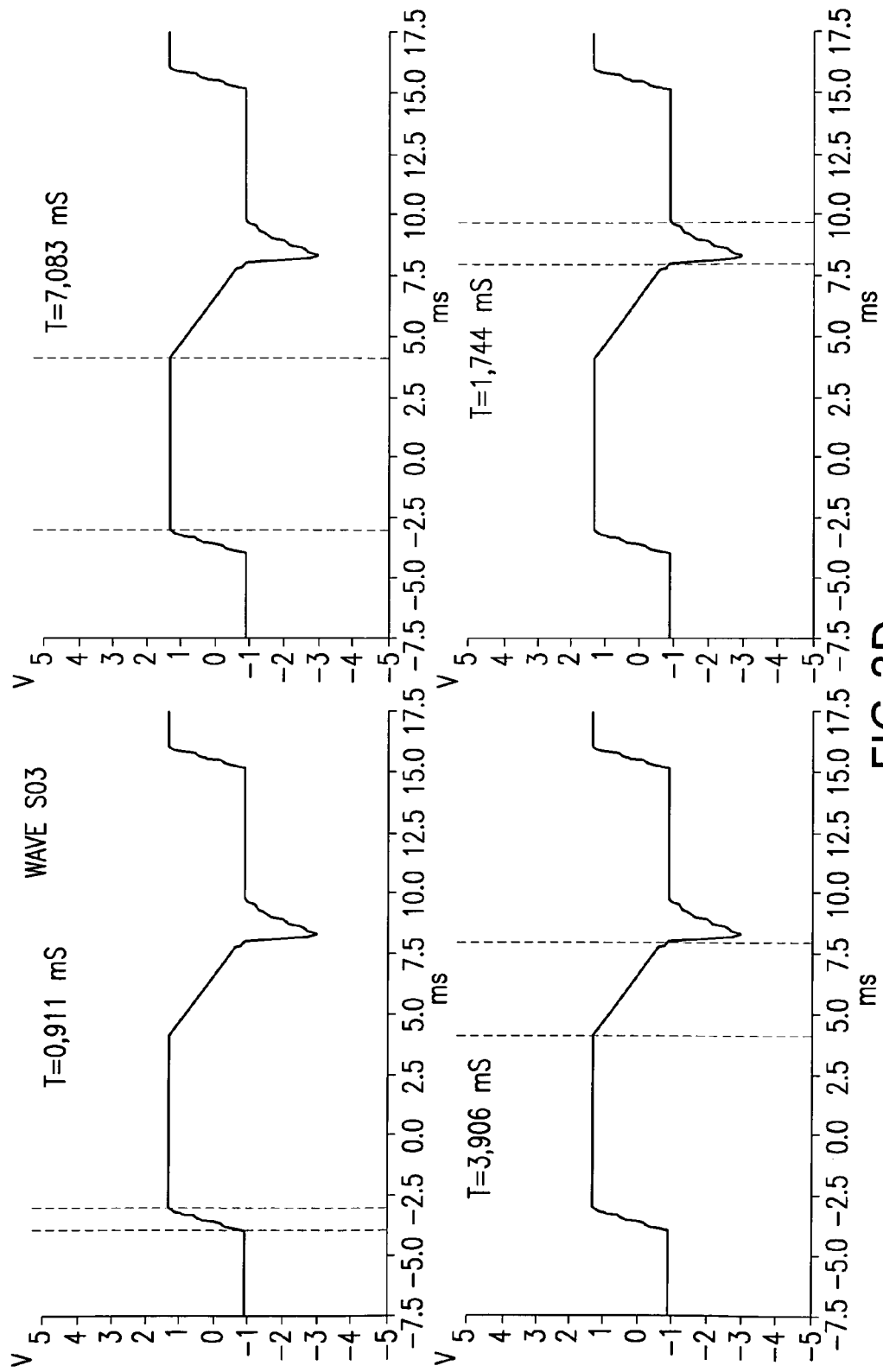
Figure 2E:
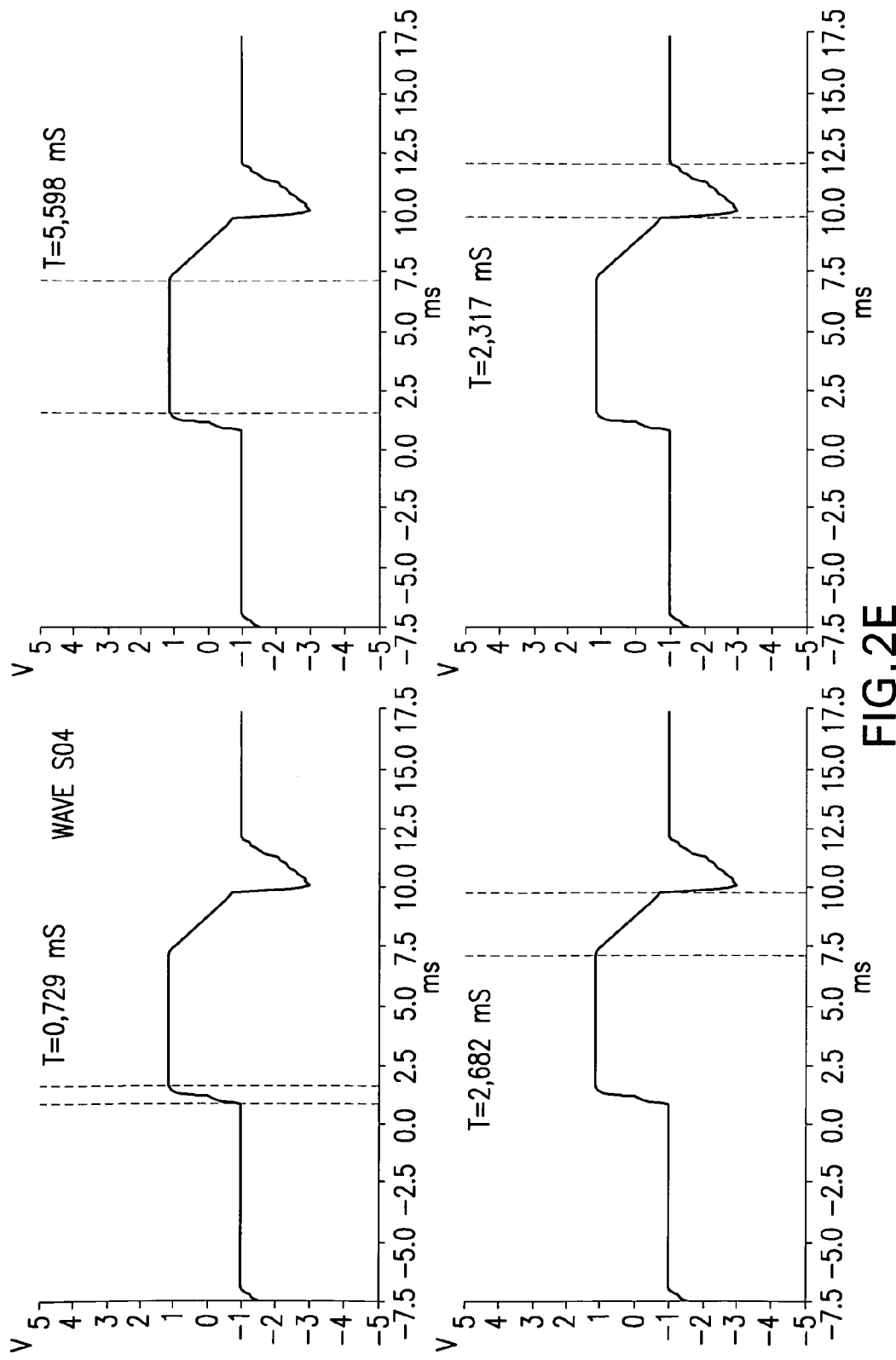
Figure 2F:
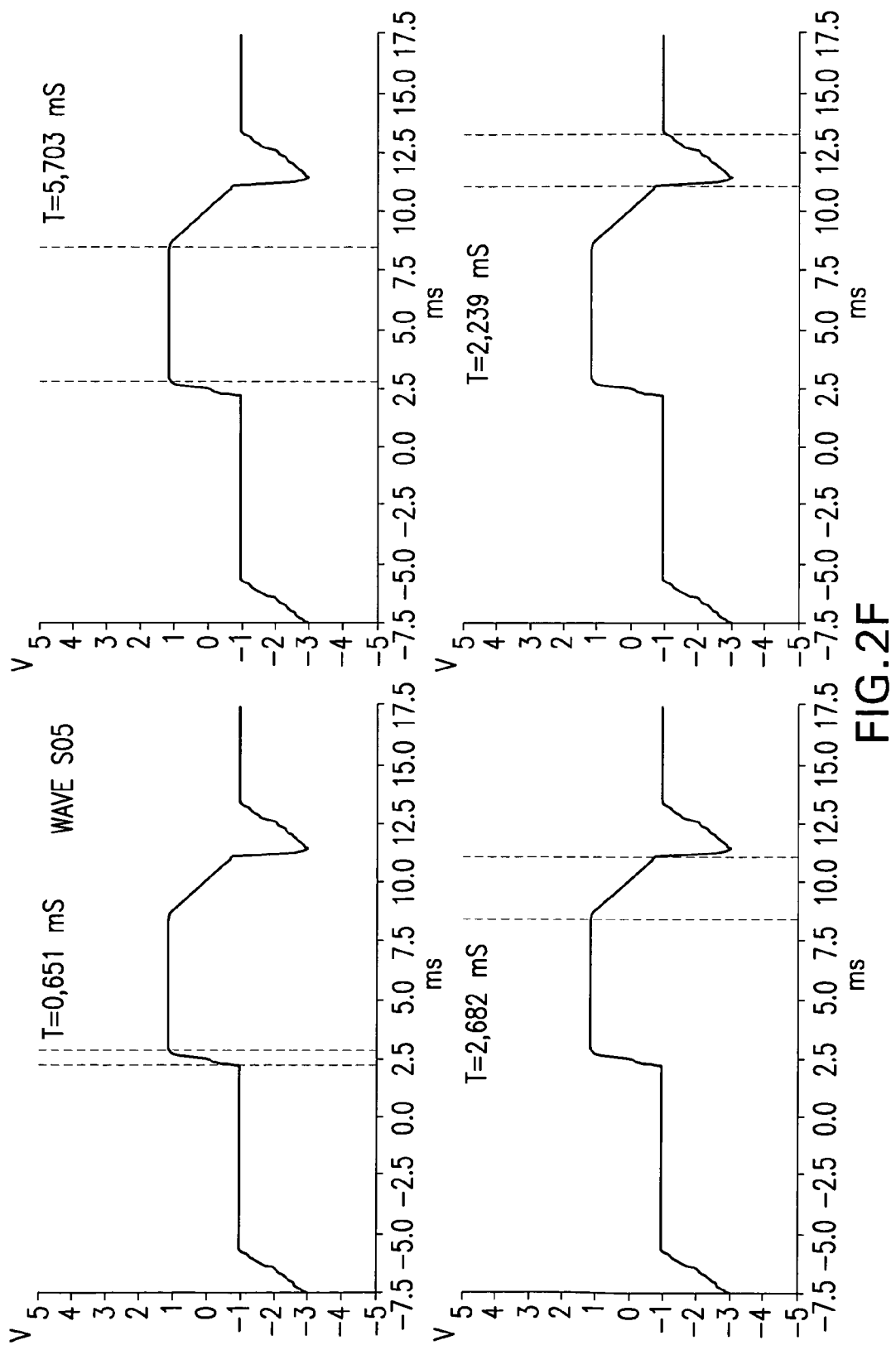
Figure 2G:
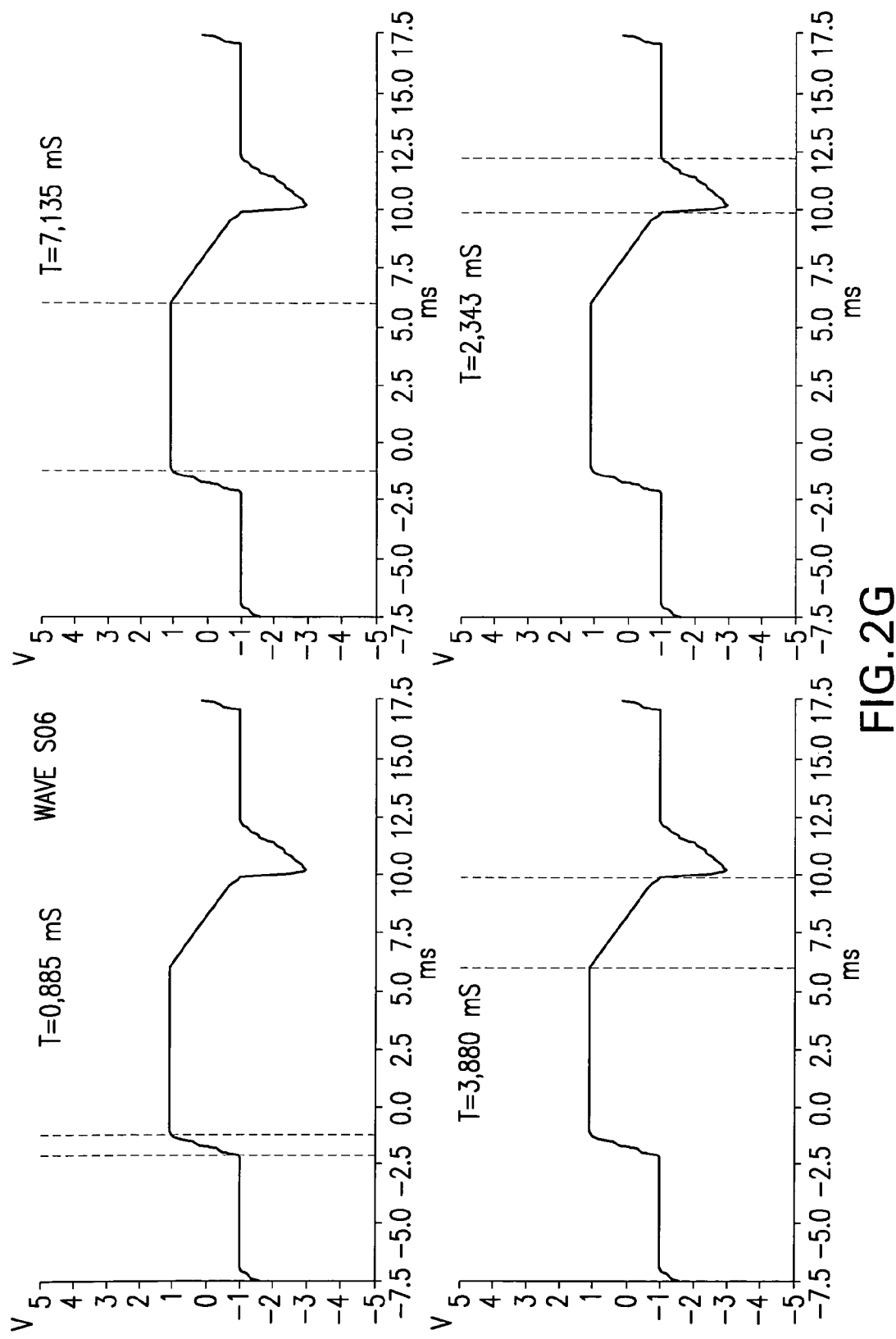
Figure 2H:
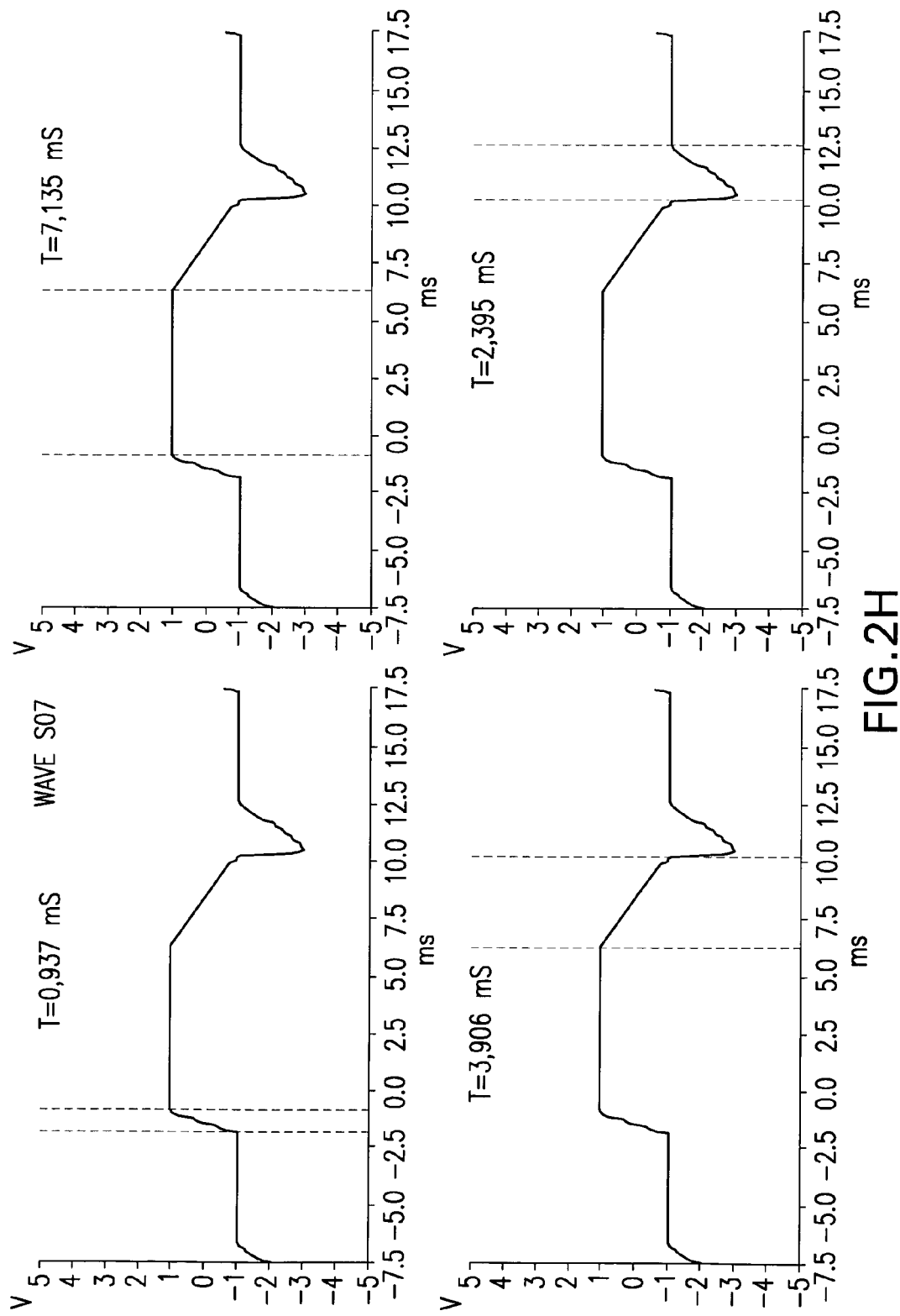
Figure 2I:
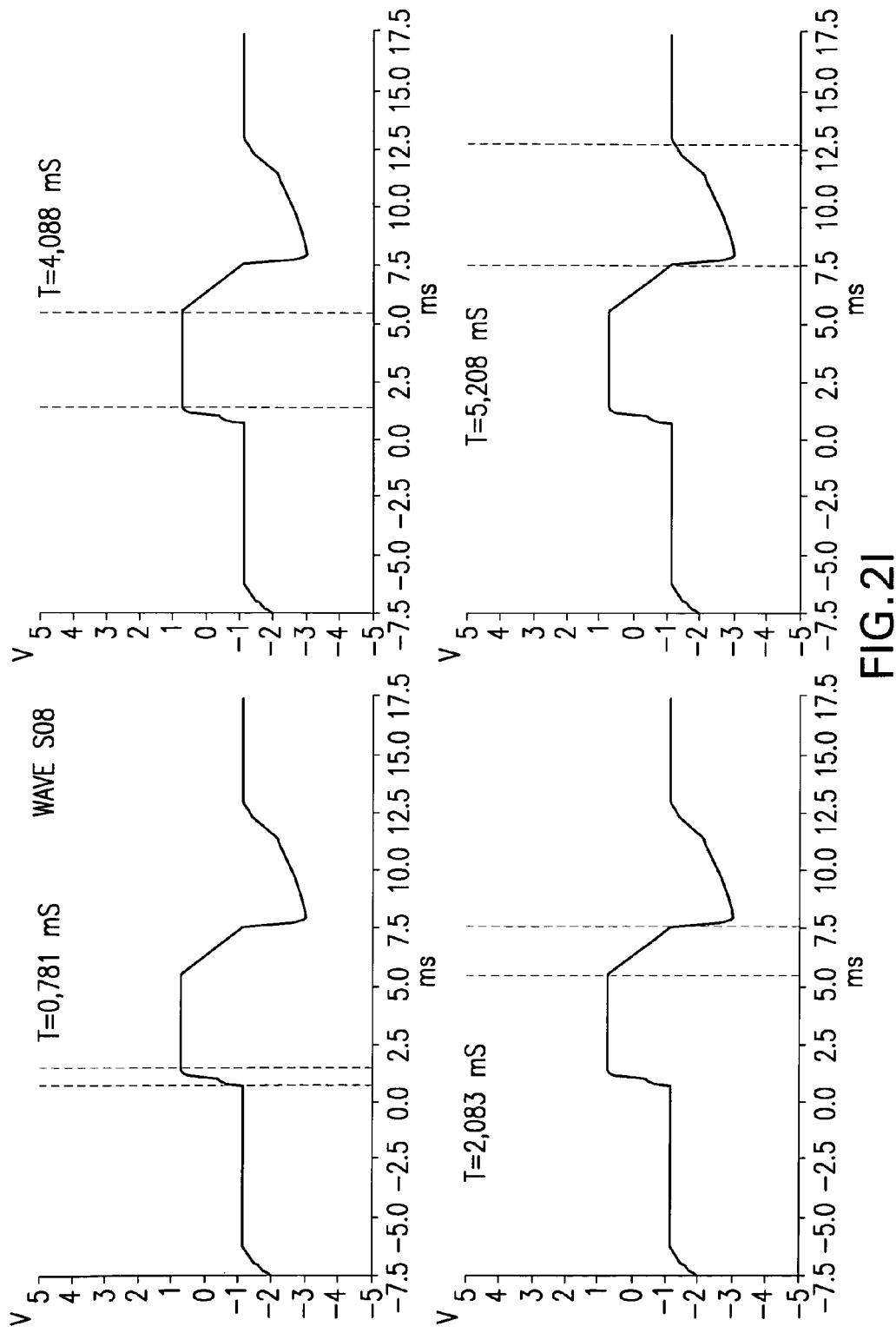
Figure 2J:
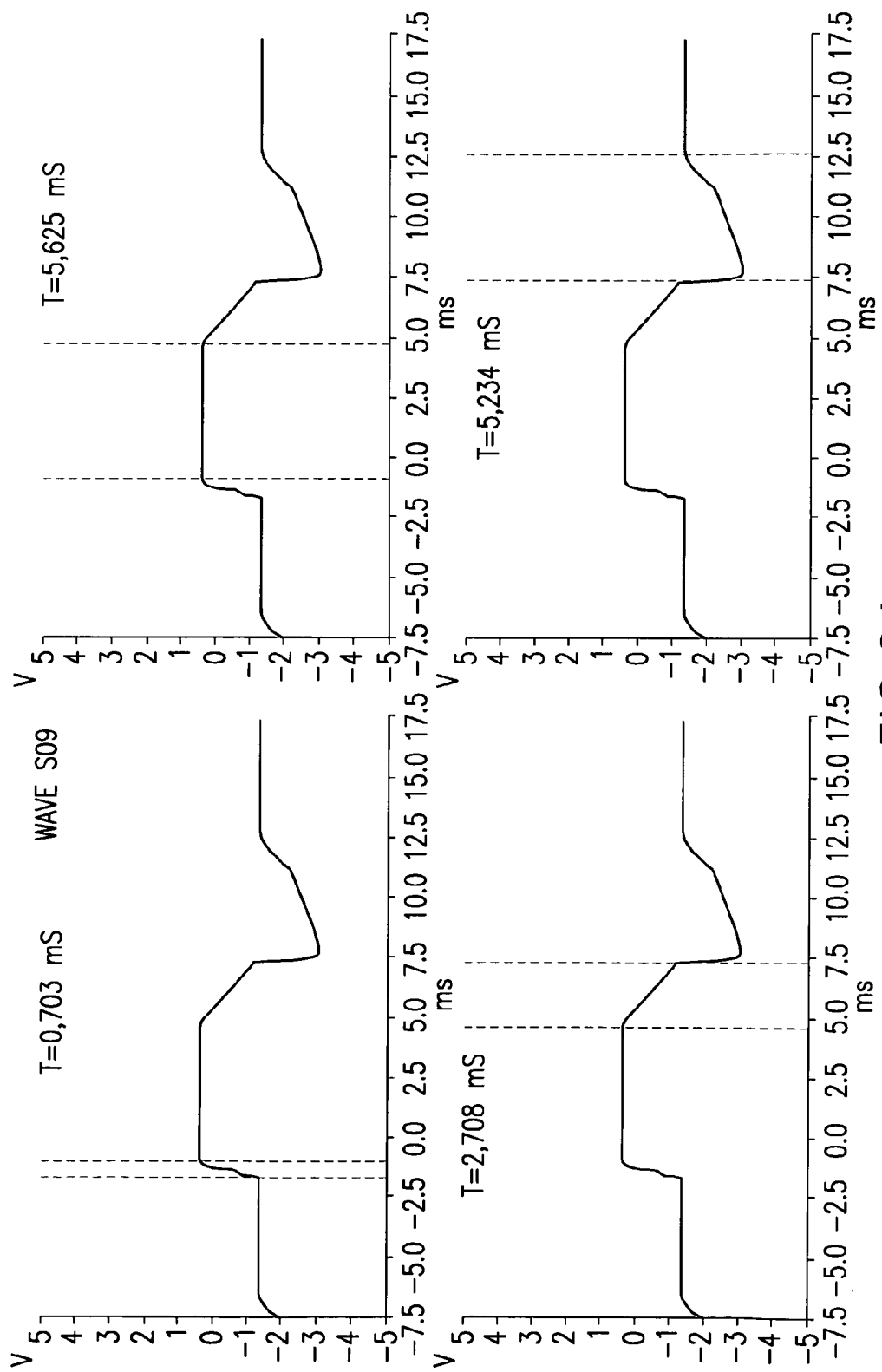
Figure 2K:
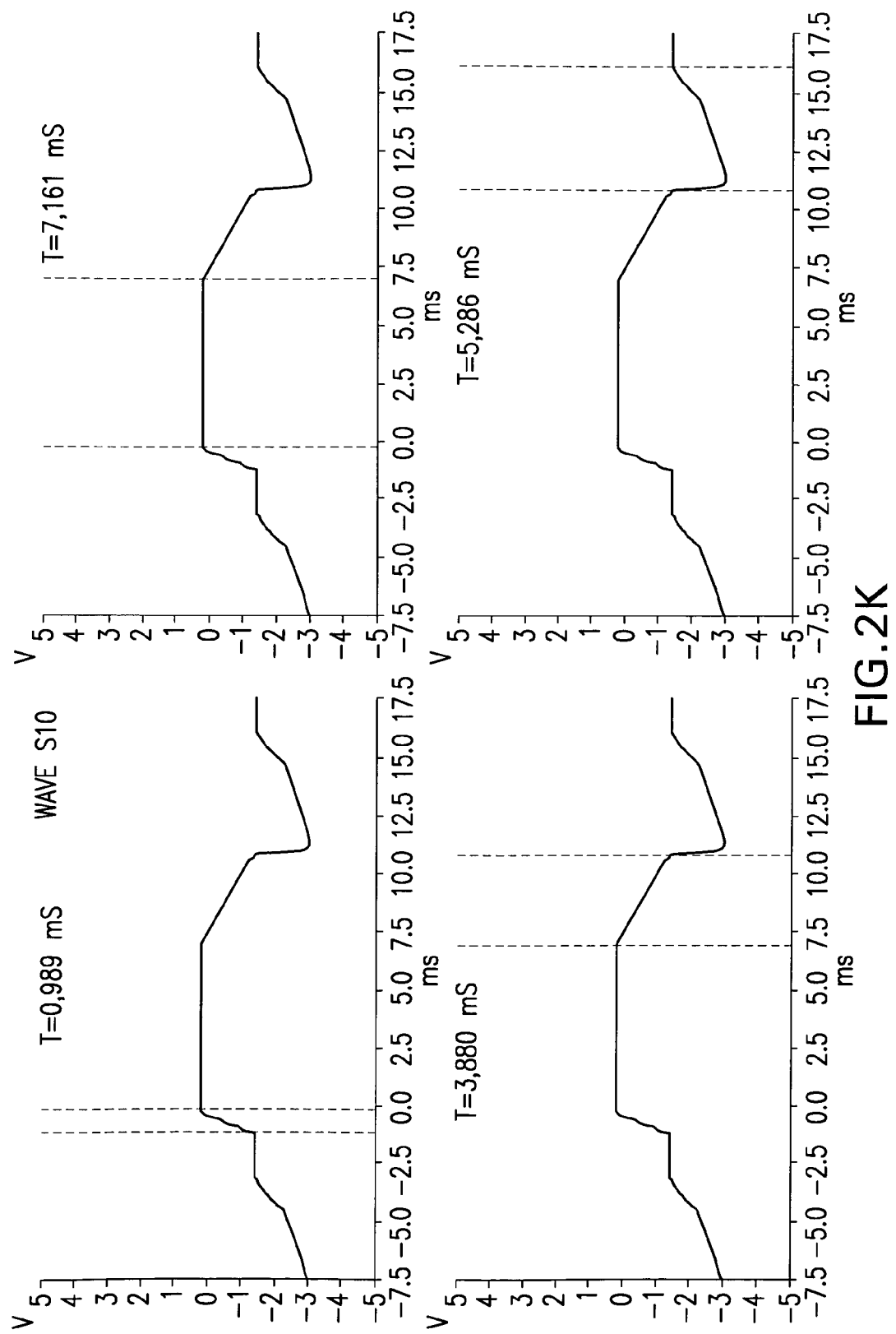
Figure 2L:
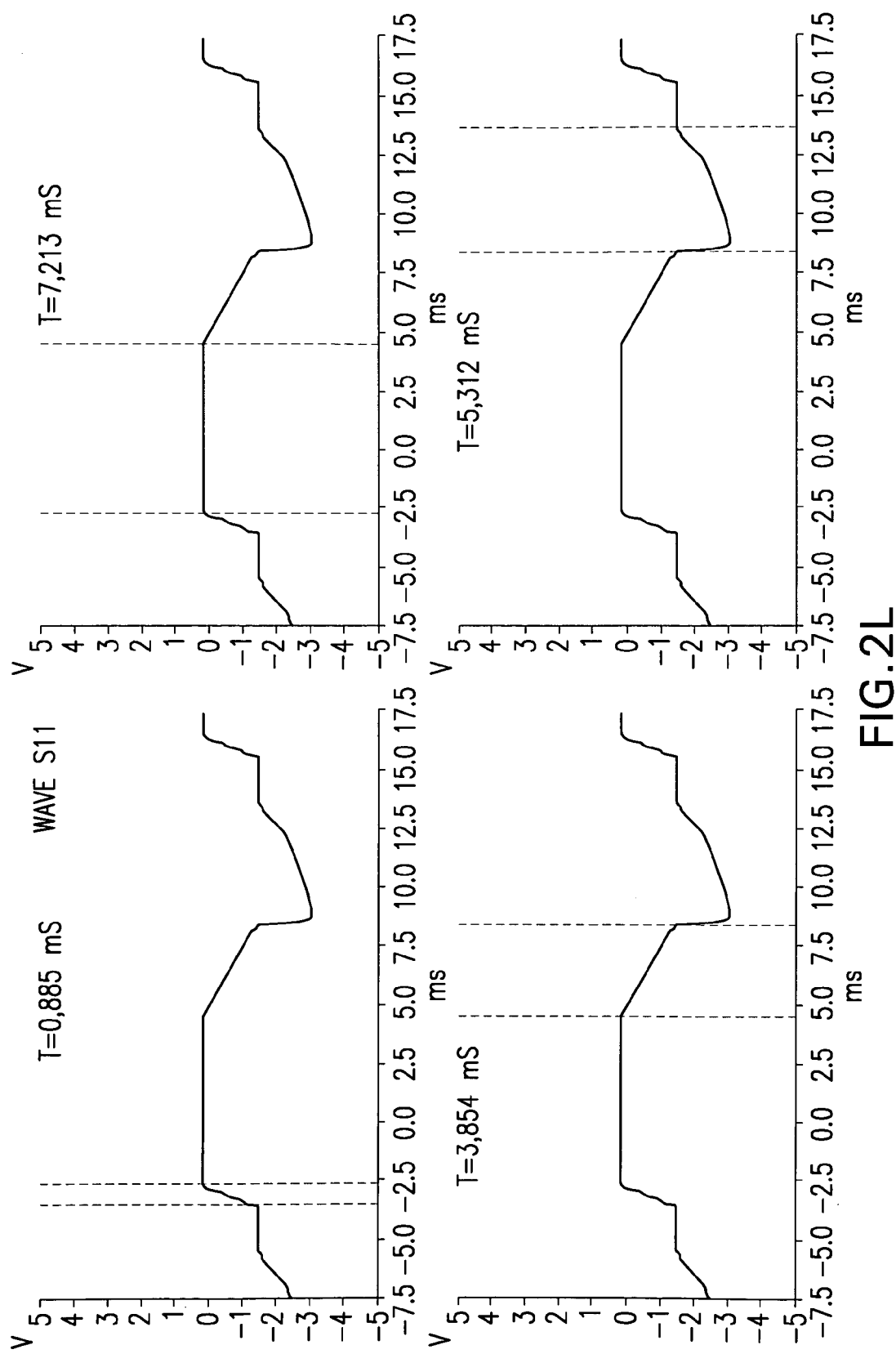
Figure 2M:
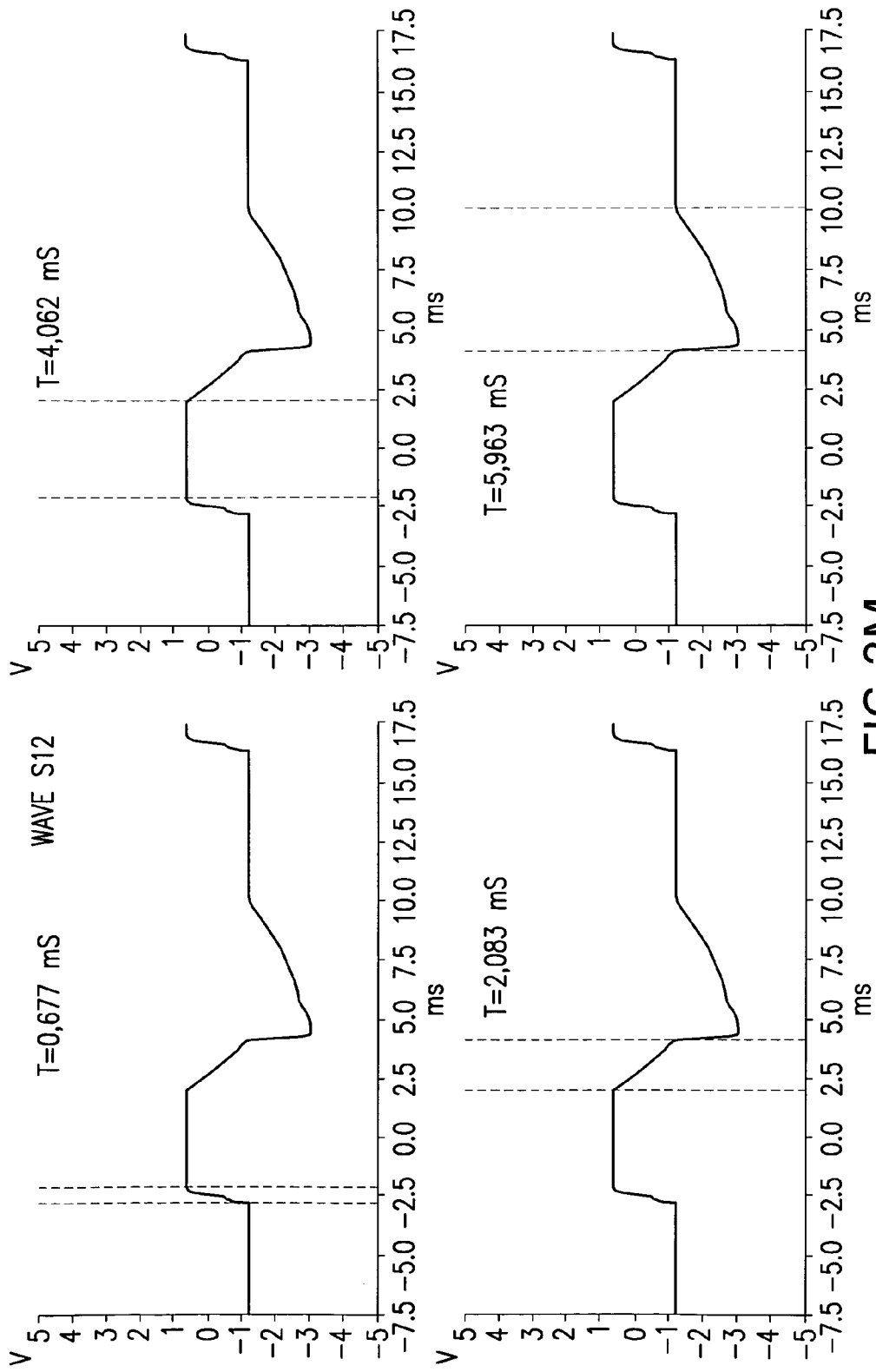
Figure 2N:
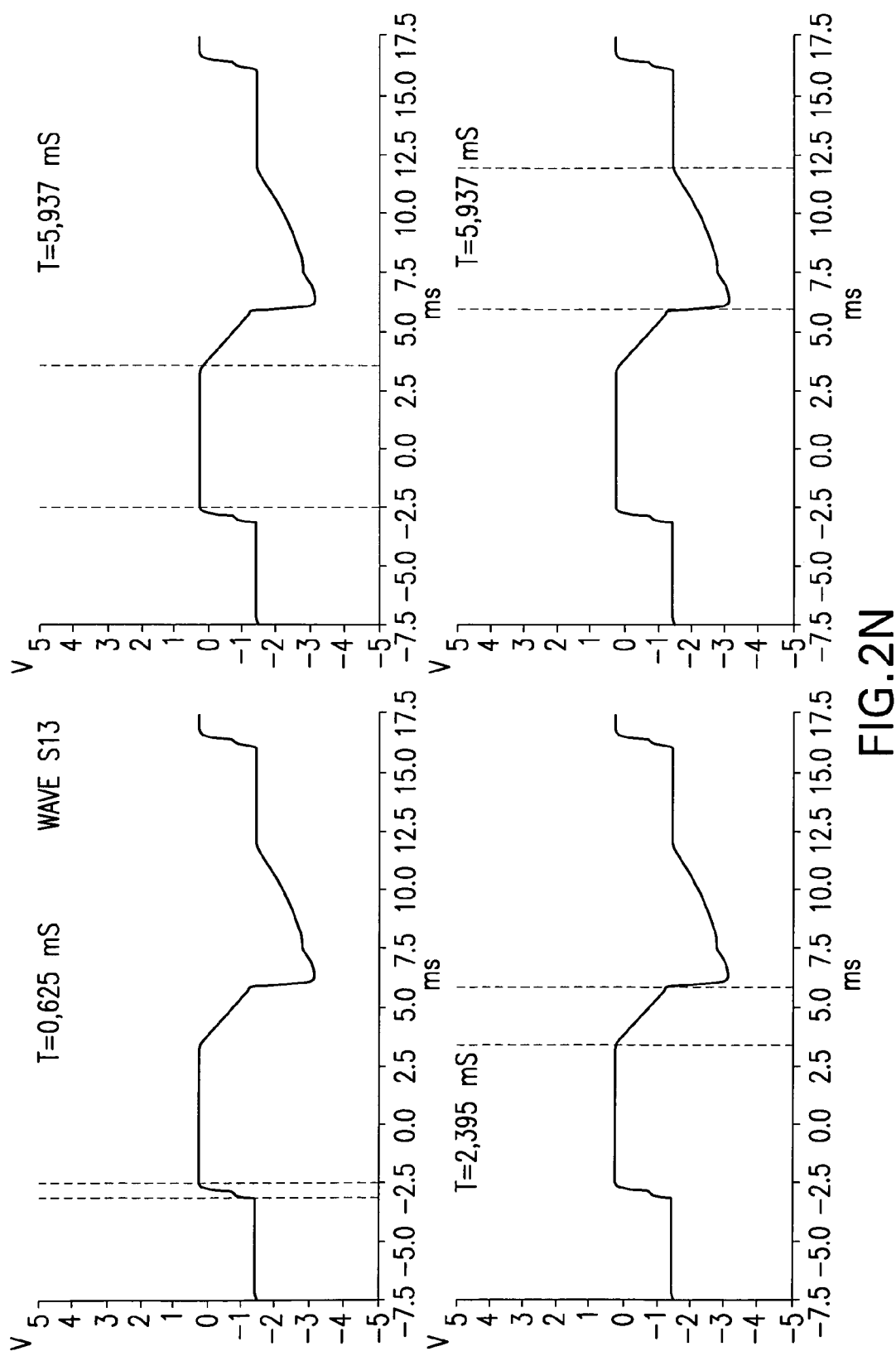
Figure 20:
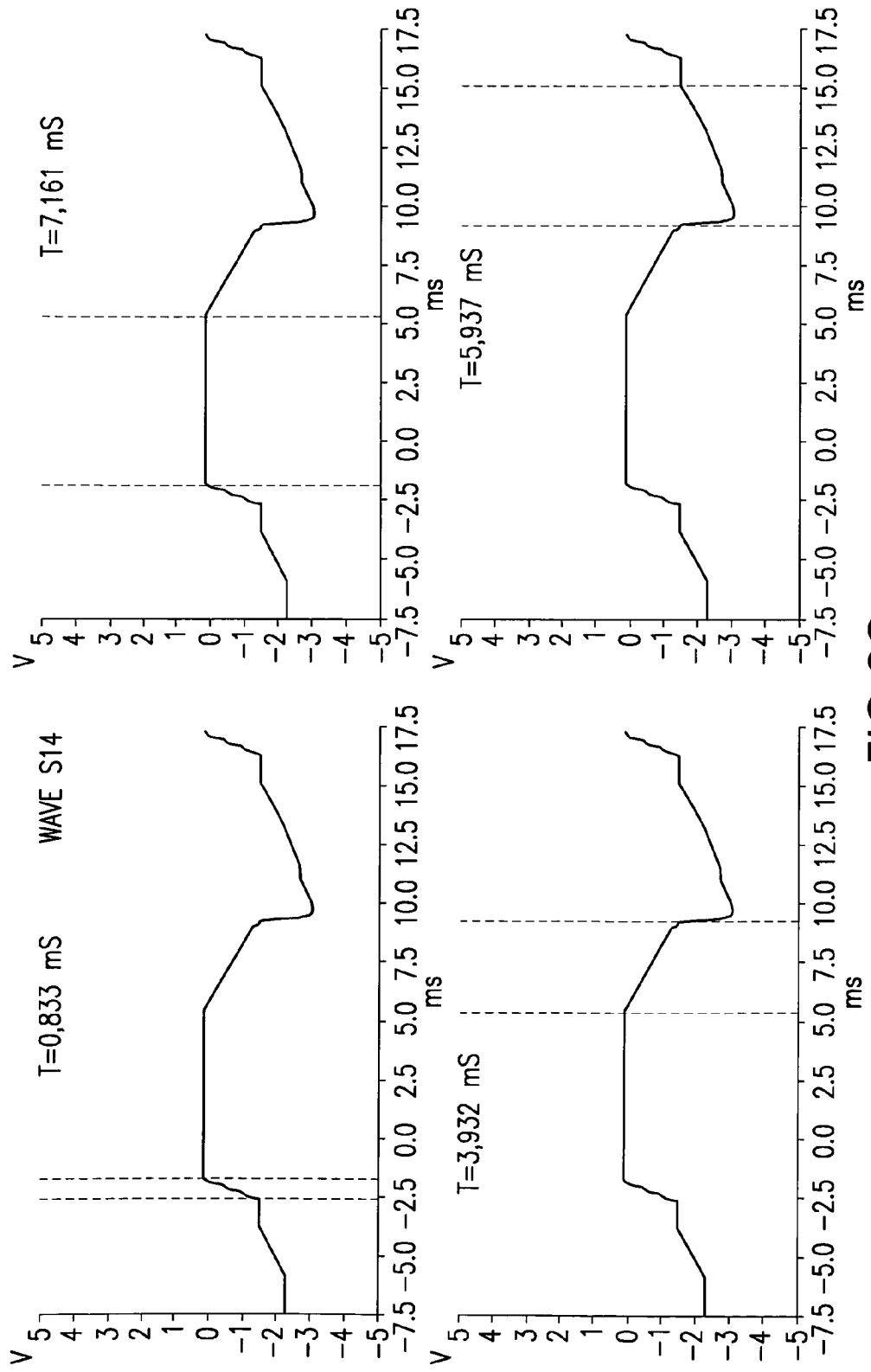
Figure 2P:
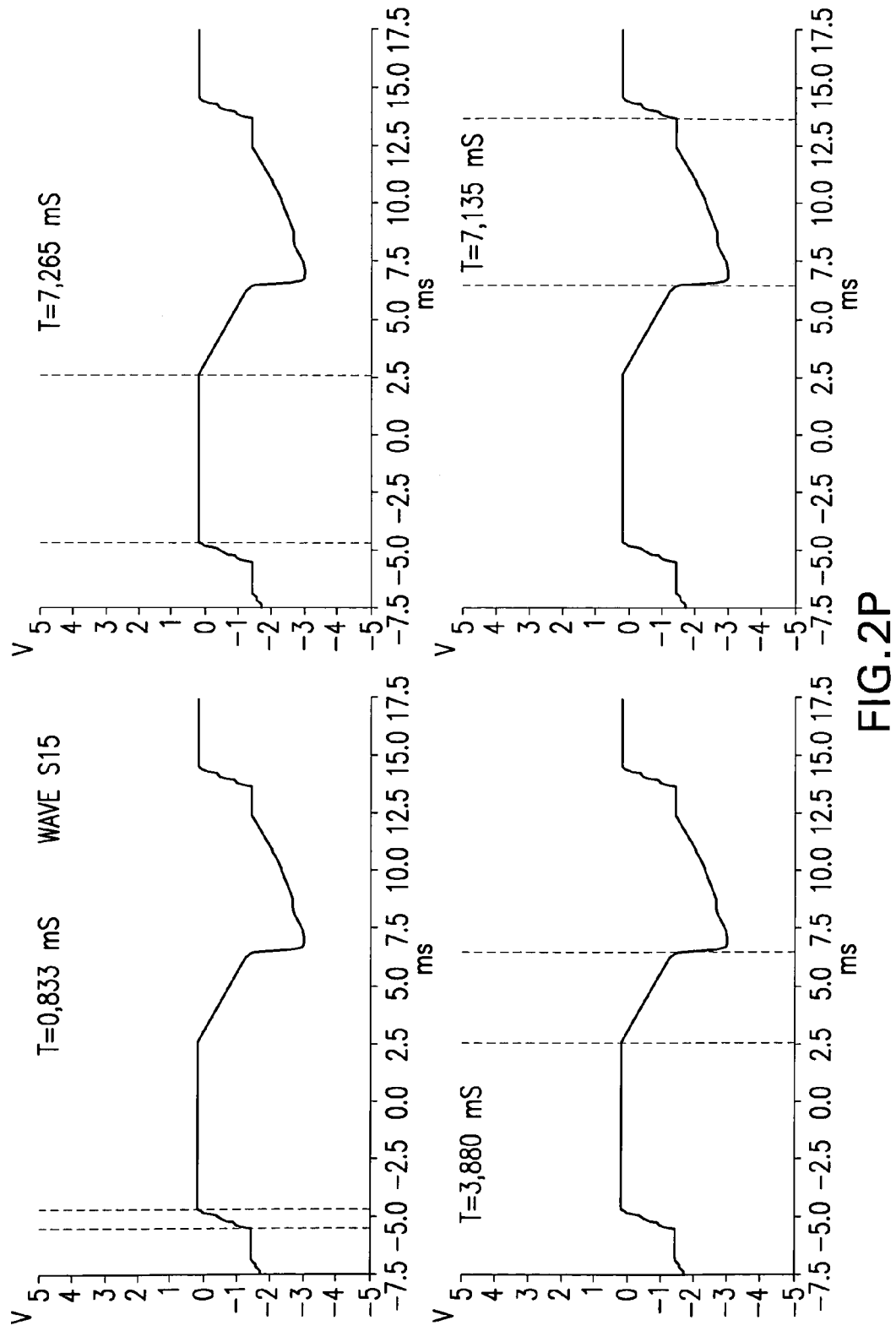

FIGS. 2A to 2P show the pattern of the waveforms preferentially selected according to the invention, S00 to S15. It should also be understood that even forms diverging from the above ones (for example variations in the amplitude of one or more samples) could be used for the application of a method such as that described here.

The images shown in those figures were obtained with a PC oscilloscope (Picoscope 3204), having the following technical features:

| Band | 50 MHz |
|---|---|
| Buffer size | 256K |
| Basic range of times | 5 ns/div to 50 s/div |
| Analog bandwidth | 50 MHz |
| Precision | 3% |
| Resolution | 8 Bit |
| Sampling rate | 50 MS/s |

Hereinafter, an apparatus according to the present technology will be described.

Figure 3:
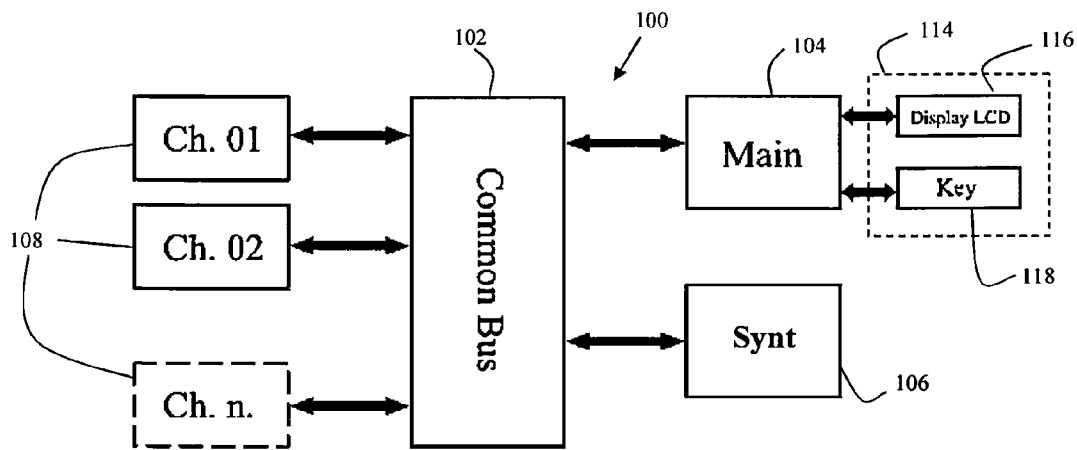
FIG. 3 is a block diagram of an apparatus according to the present invention.

FIG. 3 shows a block diagram of an apparatus 100 according to the present technology. Referring to the diagram of FIG. 3, it is possible to identify a Common Bus 102 to which there are connected the various apparatus modules that will be detailed.

In particular, the modules are: a main module "Main" 104 for management; a synthesizer module "Synt" 106 overseeing the digital/analog conversion of the sequence of primitive waveforms, as processed by the Main module 104; one or more channel output modules "$Ch_k$" 108 for carrying out a further analog processing of the signals, prior to the application of the latter to the patient's body, through electrodes 160 (see FIG. 7) precisely arranged as will be described hereinafter.

The Main module 104 provides for the full management of the treatment and the safety devices for the subject undergoing the therapy. Moreover, a serial output is provided for any communications and remote control of the device.

The hardware and the resident firmware mainly carry out three functions: a first one of user interfacing, a second one of controlling information string synthesis, and a third one of patient's safety.

At a circuit level, the Main module 104 preferably comprises data storage 110 and processing means 112, implemented with a first microprocessor, to which the I/O devices and the bus control flags interface. Such an architecture is to be deemed as within the reach of a person skilled in the art.

The user interface 114 is preferably made by means of an LCD display 116 and an array of keys 118 for commonly requested functions. Optionally, remote control via serial interface is possible. It is understood that other interface typologies are viable, e.g., a touch screen and the like.

In addition, the Main module 104, and specifically the storage 110 and processing means 112, is assigned to controlling the synthesis of data, data which comprises the above-indicated parameters $V_i$ and also second parameters $T-pack_i$, $Freq_i$, $T-slot_i$, associable to each primitive waveform $S_i$, whose meaning will be explained in detail.

Advantageously, the set of primitive waveforms S00-S15 may be stored on a storage medium, be it internal to the Main module 104, and an integral part thereof (nonvolatile memory modules or the like) or external thereto and/or removable, like e.g., a CD-ROM or the like.

Resident software continually processes the sequence S to be digitalized, sending on the bus 102 a data set $B_i$, identifying said sequence S, required by the synthesizer module 106 in order to produce, in real time, an electric output signal "Out", corresponding to the required sequence S.

Figure 4A:
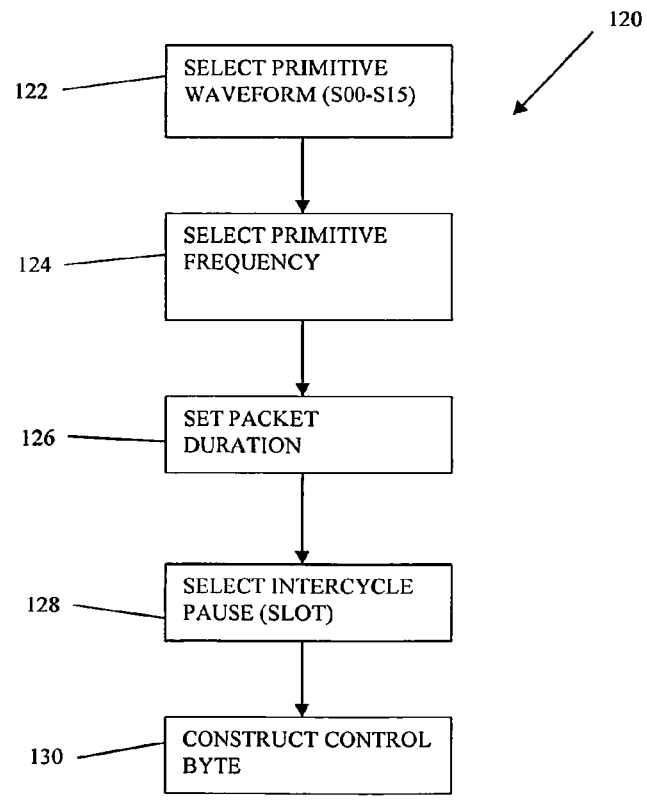
FIG. 4A is a flow chart schematically illustrating a control algorithm of the synthesis according to the present invention.

In particular, the software residing in the Main module 104 implements a selection algorithm, schematically illustrated in the flowchart 120 of FIG. 4A.

Figure 4B:
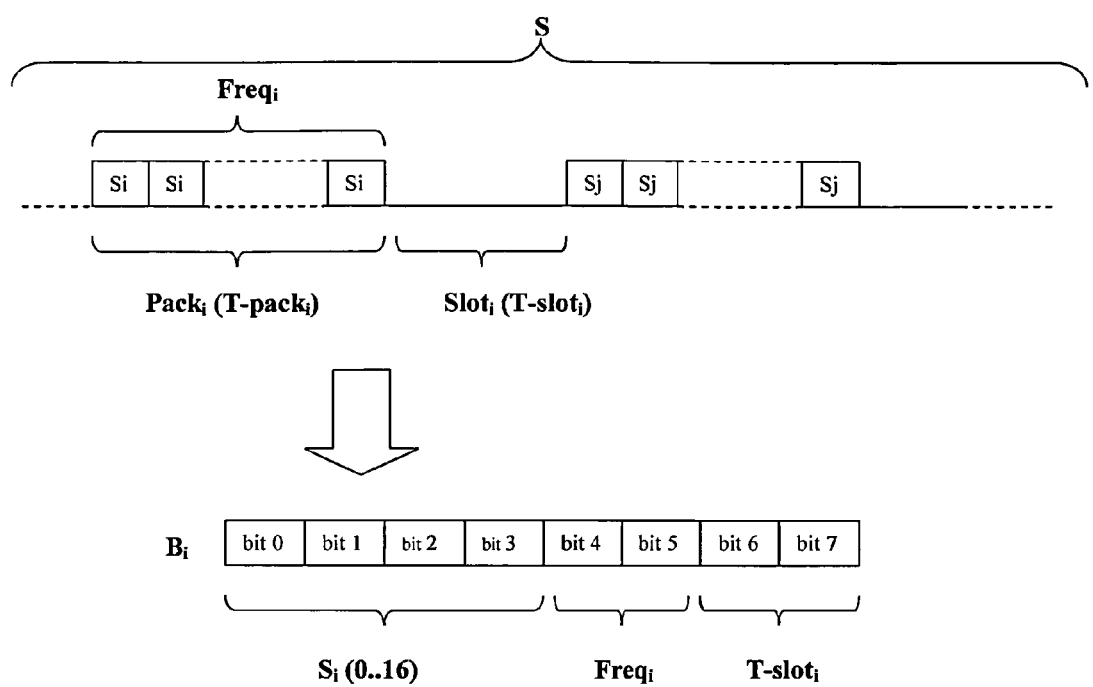
FIG. 4B schematically illustrates the algorithm result, in terms of sequence of data S and control bytes S.

For clarity's sake, in FIG. 4B a schematization of the outcome of the selection algorithm in flowchart 120 of FIG. 4A is shown. In FIGS. 4A and 4B, the description the following definitions will be used:

Packet—Pack: sequence of an individual primitive waveform, repeated over time. The time duration $T-pack_i$ of a packet $Pack_i$ is preferably of at least 700 mS, with a preferred upper limit of about 10 s. However, it is understood that a packet duration of could also be longer than 10 s, and even equal to the treatment duration.

Inter-cycle pause—Slot: pause interval between a packet and the next one of a time duration (value) $T-slot_i$ preferably ranging from 0 to 38 mS.

Frequency—Freq: frequency to be associated to the waveform of the packet, preferably ranging from about 43 to 52 Hz, values corresponding to a period ranging from about 23.26 ms to 19.23 ms.

Therefore, the sequence S will be processed as a composition of one or more of said primitive waveforms $S_i$ in a time sequence, each of which will in turn be processed on the basis of the parameters $T-pack_i$, $Freq_i$, $T-slot_i$, which are calculated according to predetermined modes that will be illustrated hereinafter.

The geometry of each individual primitive waveform $S_i$ described has an intrinsic content of information such as to induce analgesia.

In this sense, making a traditional-type TENS which, instead of using the classic waveforms derived from square, sinusoid, triangle, continually delivers even only one of the waveforms S00-S15 described here, would already constitute a remarkable advance in technology and results.

However, any processing, described hereinafter, of the basic information of the individual primitive waveforms, into packets and therefore more complex information strings, is preferable in order to optimize the analgesic effect in the most difficult cases, above all of chronic pain, to which the device 100 is explicitly destined; i.e., those cases not satisfactorily responding to any conventional pharmacological and/or surface or implanted electroanalgesic treatment.

Yet, before continuing with the description, a short premise is in order. CNS by its own nature discriminates and processes information, but in this process it also has the property of modifying over time the perception of information into ground noise if the content thereof is monotonous, e.g., always the same for long time intervals. An explanatory analogy is what happens when one is in a crowded place, full of people talking. At first, one will tend to concomitantly discriminate one or more voices present in the surrounding environment, yet over time perceptive adaptation will lead to consider the whole as environment noise, i.e., ground noise, ignoring the associated information content, though the latter is still present. This situation changes only if background noise changes briskly, i.e., if in monotony a new element is introduced which varies the average information content, e.g., a person suddenly raising his/her voice, a plate falling and breaking, etc.

A similar problem is known in the use of traditional TENS, with its known limitations in efficacy. Over time, initially responsive patients become resistant and the therapy is no longer effective.

Since acknowledged information always has the central role of controlling CNS discriminating properties, just as for the analgesic effectiveness in the different pain typologies, it is beneficial to synthesize different "non-pain" information sequences, thereby widening the dynamics of the resulting string and avoiding monotony, so that treatment proves effective. This principle was experimentally tested in clinical practice, with a favourable outcome for the object and the ends of the present technology.

The strategy of the dynamic construction of information is processed by the Main module 104, which, by writing control bytes $B_i$ on the bus, makes it available to the synthesizer module Synt 106; the latter, by reading the current byte, accordingly generates the required geometry with the associated properties of frequency, inter-cycle pause, packet duration.

Each control byte $B_i$ may contain at least the information related to an individual packet, and specifically:

a first four-bit portion to code the primitive waveform $S_i$ to be used for the current packet $Pack_i$, a second two-bit portion to set the frequency $Freq_i$ (43, 46, 49, 52 Hz) thereof, and a third two-bit portion to set the duration of the inter-cycle pause $T\text{-}slot_i$ (0-38 mS), subsequent to the current packet $Pack_i$.

The time duration $T\text{-}pack_i$ of the packet is instead determined by the time in which the corresponding control byte $B_i$ is kept unvaried and available on the BUS 102.

The dynamic construction of the control byte $B_i$ occurs by following probabilistic criteria, whose reference parameters have been identified in the fundamental scientific research of the subject inventor, propaedeutical to the development of the described.

The core for processing the probabilities of the control byte coming out in the composition is a random number generator slaved to a probabilistic filter that modifies its output in percent terms.

Essentially, a pseudo-random number ranging from 1 to 100 is continuously generated. This number passes through a conditional filter setting the probability thresholds of the actual user. For example, when desiring a variable P at each output of the random generator to have a 40% possibility of being 0 and a 60% possibility of being 1, a condition such as:

"IF random number<41 then P=0 else P=1" will be used.

This code carries out the filtering required in order that the arbitrary probability, which has been defined to modify the values of variable P starting from a random number, be complied with.

This design is explicitly recalled in the following descriptions, related to the algorithm for control byte construction, applying one or more of the conditional filters described hereinafter.

Selection Probability of Primitive Waveform.

Referring to FIG. 4A, at step 122, selection of primitive waveforms $S_i$ is performed on the basis of a first probabilistic criterion. Though it is understood that such a first criterion could entail a completely random selection, according to a preferred embodiment, it is preferable to vary each time the probability of selection of each of the waveforms, by dynamically varying a first probabilistic filter used for this purpose.

In particular, the 16 primitive waveforms are subdivided into 4 groups, each containing 4 different primitive waveforms. Initially, the same probability (25%) of coming out is assigned to each group, and the same probability (25%) of coming out is assigned to any group-associated primitive waveform.

When a group is selected, its probability of coming out is reduced to 10%, that of the immediately subsequent group is automatically increased to 40%, and that of the remaining groups is brought back to the 25%, with a circular pattern.

In practice, selection of group 1 implies setting at 10% its next probability of coming out, at 40% that of group 2, at 25% that of groups 3 and 4. Likewise, selection of group 4 implies setting at 10% its next probability of coming out, at 40% that of group 1, at 25% that of the remaining ones, etc.

Another step is the modifying of the probability of selection, within the selected group, of one of the 4 possible waveforms, initially equiprobable, within the same group. The selected waveform, in conjunction with the associated frequency, brings to 0% its next probability of coming out in the group, probability that is restored to 33.33% only when another waveform is selected which belongs to the same group and is associated to the same frequency, following the same procedure of modifying the next probability of coming out within the same group.

In practice, before setting at zero its probability of coming out in the absence of a general resetting, each waveform has 4 different possibilities of coming out in connection to the 4 possible associated frequencies. Therefore, consecutive coming out of the same waveform with a different frequency is possible, though it is a low-probability event, yet the consecutive coming out of the same waveform with the same frequency will not be possible in the preferred embodiment.

It has to be pointed out that the association of the 16 available waveforms to the 4 provided groups follows analytical criteria associated to experimental validations. One of the groupings experimentally detected as more effective is the following one:

Group 1: S00, S01, S02, S03
Group 2: S04, S05, S06, S07
Group 3: S08, S09, S10, S11
Group 4: S12, S13, S14, S15

However, it should be deemed valid in any possible combination thereof and even with repetitions, as anyhow the resulting analgesic information rate is always present, albeit with different effectiveness.

Concerning the further parameters indicated, $T\text{-}pack_i$, $Freq_i$, $T\text{-}slot_i$, probabilistic selection rules are still applied. In particular, parameters are selected from values, or value ranges, set on the basis of further and respective probabilistic criteria, which preferably are dynamically modified by applying further probabilistic filters, in order to vary each time the selection probability of set starting values.

Hereinafter there are described probabilistic filters related to the above-indicated parameters, as preferably used in a preferred embodiment. Once again, it is understood that said conditions may be modified, without thereby altering the inventive concept underlying the present invention.

Selection Probability of Frequency Associated to Selected Primitive Waveform

Still referring to FIG. 4A, at step 124, a primitive frequency is selected. It is envisaged that the four preferred frequencies, to be assigned to the selected primitive waveform, be the following ones:

| | |
|---|---|
| 43 Hz | 15%, |
| 46 Hz | 45%, |
| 49 Hz | 15%, |
| 52 Hz | 25%. |

As mentioned hereto, the selection of one of the frequencies also affects the subsequent probability of selection of the waveforms, as described above.

Selection Probability of Inter-Cycle Pause.

Still referring to FIG. 4A, at step 128 intercycle pause is selected. It is noted that step 126 could also occur next. Indeed, the order of the steps shown and described is merely illustrative and not meant to be limiting in any way. The overall therapy time is divided by 4, and differentiated into corresponding phases at which the selection probability of a duration is modified. The duration of inter-cycle pauses pause deriving in terms of probability is the following:

| | |
|---|---|
| Phase 1: | 70% - 0 mS, 30% - 12 mS |
| Phase 2: | 70% - 12 mS, 30% - 25 mS |
| Phase 3: | 70% - 25 mS, 30% - 38 mS |
| Phase 4: | 70% - 38 mS, 30% - 0 mS |

Time Duration Probability for a Packet.

Still referring to FIG. 4A, at step 126 packet duration is set. In this case, randomization is simpler and sets the time duration of a packet from a minimum of 0.7 seconds.

The synthesizer module "Synt" 106 comprises first of all means for generating an output electric signal "Out", corresponding to the sequence S as programmed by the Main module 104.

Synthesis preferably occurs by 8-bit digital/analog conversion, controlled by resident firmware.

Figure 5:
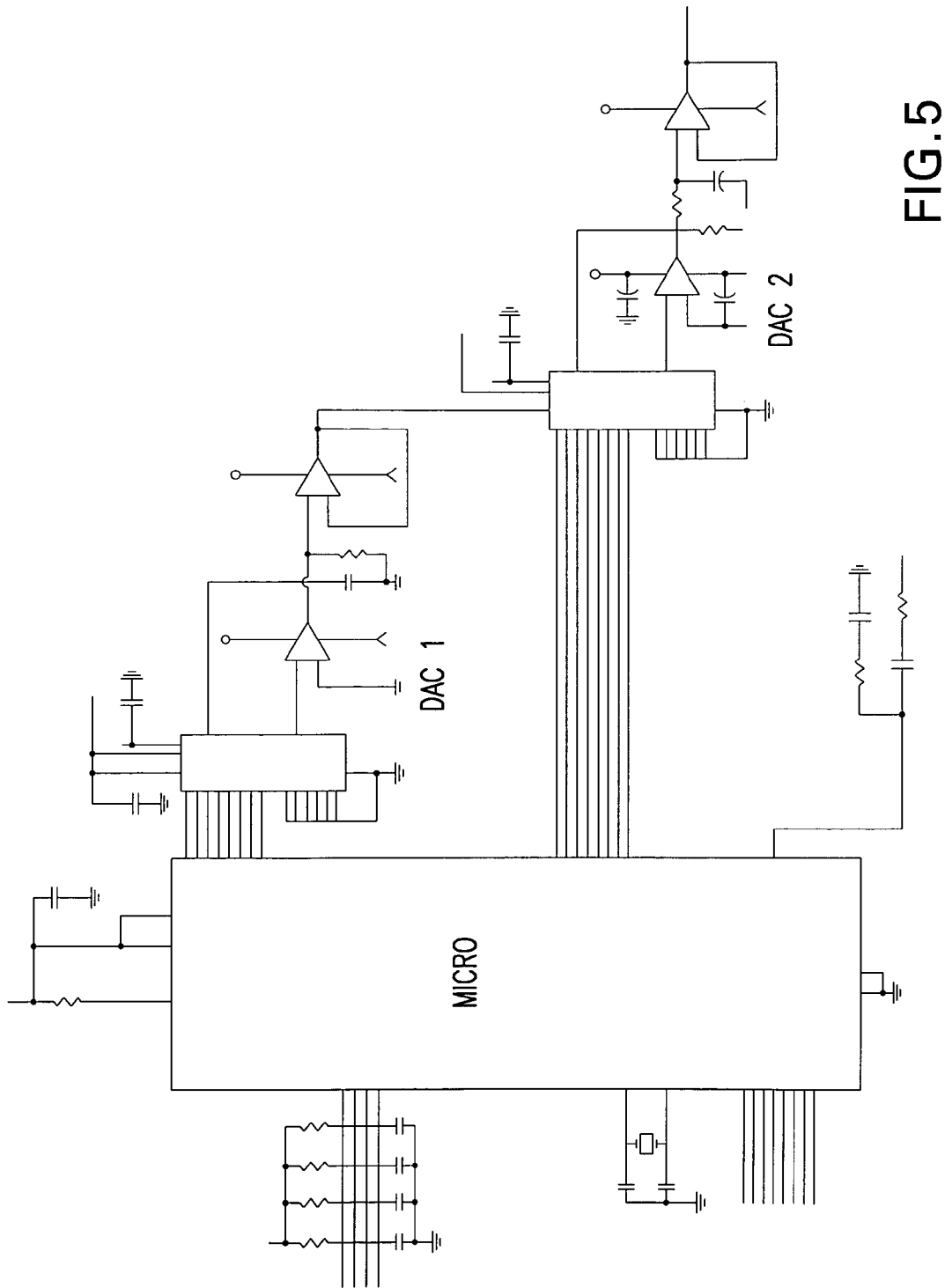
FIG. 5 is a circuit diagram of a synthesizer module according to the present invention.

Referring to the diagram of FIG. 5, there may be observed the use of two digital/analog converters (hereinafter DAC) 140, 142 slaved to a second microprocessor "Micro" of the processor 112 of the main module 104. The second Micro of the processor 112 is dedicated to synthesis, e.g., a synthesis microprocessor.

The synthesis microprocessor continually reads on the bus the current control byte $B_i$ processed and provided by the Main module 104, and, on the basis of the information contained therein, provides on the input port of the DAC2 142, the amplitude values (read by the corresponding vector S00-S15) to be converted for the synthesis of the selected waveform. Of course, each individual sample is timed according to the selected frequency $Freq_i$.

The DAC2 output, typically stepped, is preferably integrated by a low-pass filter made with an output operational amplifier, which also works as buffer. In the embodiment described, filter cutoff (frequency) is calculated at about 1592 Hz, and its slope is of 6 db/oct. At the output, the Out signal is made available on the bus 102 for the channel modules 108 connected thereto.

Preferably, the reference input of the converter DAC2 142, is not connected to a constant-value voltage source as usual, but supplied by the other DAC1 140.

The input port of the converter DAC1 140 is supplied with pre-programmed data, in order to carry out a rapid equalizing of the response of current feedback circuits present on the subsequent channel module, precision rectifier included, depending on the different waveforms synthesized at the moment.

Thus, at the beginning of each change of waveform, a first amplitude modulation is obtained of each packet due both to digital equalization and to the response time of the precision rectifier, whose output is continuously compared with the output level manually set to keep the output level constant even if the load modifies its impedance in the therapy time.

Modulation is useful to enhance the noise figure, in terms of amplitude non-linearity, present in long sequences of action potentials typical of a nerve cell subjected to prolonged stimuli. Overall dynamics of the output variation, considering 100% as maximum amplitude, can drop to 67% of the upper limit.

As mentioned, the analog signal thus produced is made available on the bus 102 for all channel modules $Ch_k$ 108 provided and connected thereto.

A channel module $Ch_k$ 108 may be made according to different architectures, from that envisaging merely the use of a microprocessor to that envisaging a wide use of operational amplifiers and wired logic. Alternatively, though requiring more componentry and higher circuit complexity, is usually intrinsically more stable and reliable, as well as less noisy on the level of processing and analog output.

These requirements are fundamental to the safety of a patient subjected to the treatment, and for this reason preferable with respect to other industrial demands.

Figure 6:
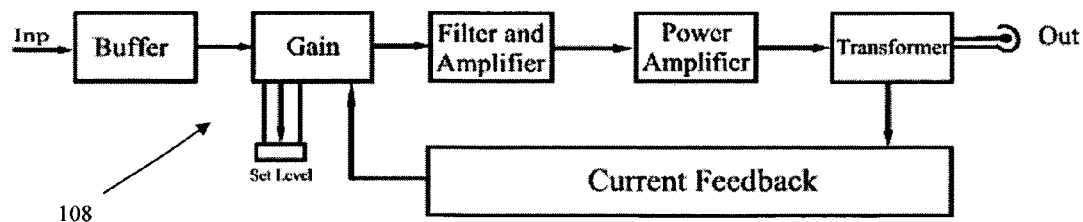
FIG. 6 is a block diagram of a channel module according to the present invention.

The block diagram of FIG. 6 schematically shows the structure of a general channel module $Ch_k$ 108 that should perform the required functions, substantially of filtering and amplifying the output signal provided by the Synt module 106, of adjusting in feedback the current level of the output signal, needed also to compensate for pressure variations on the electrodes 160, perspiration effects, alarm in case of cut-off or short-circuiting of the external wiring on the patient.

It is deemed that the implementation of a channel module 108, once its functionalities have been described and the needs to which it is subject, entails no specific technical problems and are within the skill of a person in this field.

Figure 7:
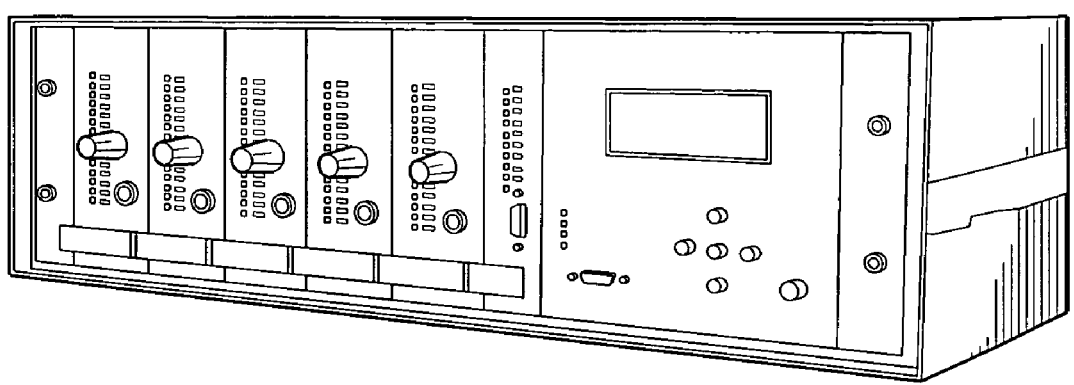
FIG. 7 is a view of a pair of electrodes to be used in the use of the present invention.

Referring to FIG. 7, two electrodes 160 are shown. In a preferred embodiment, single-use 5-cm electrodes 160 of ECG-type or of equivalent surface may be used.

Output signal amplitude control depends on a level, manually set by the user with a mere potentiometer, which, compared to a small fraction of the output signal, representative of the current actually delivered on the user, drives a digital potentiometer. This comparator-driven digital potentiometer sets the actual output current, but also performs the task of compensating for differences between the manually set value of current intensity and deviations of the effective value over time, due to electrode gel drying, skin dehydration, pressure variations on the electrode 160, and the like.

Current feedback is also monitored with a threshold comparator to ascertain whether standard operating limits have been exceeded, an event activating safety protections with cut-off of on-patient output, restorable only manually upon removing the causes of intervention of the protection.

The signal thus controlled is sent to a low-pass filter cut off at 159 Hz with a 20 slope of 6 dB/oct., and voltage-amplified to drive a class-B power amplifier, preferably comprised of two complementary Darlington pairs. The power stage has as load, a transformer/separator that works as a voltage raiser (1/39 ratio) and decouples the patient from the remainder of the circuitry, increasing the insulation level and the safety to any power-supply failures. Maximum voltage deliverable by the amplifier is preferably of 95V RMS on a>1 Kohm load. Maximum current delivered to the patient is limited by a series resistor at the output and by a varistor, preferably so as not to exceed 9 mA. Also the current output fraction feed-backed for the above-described adjustment purposes is preferably decoupled through a transformer, for the same user's safety reasons.

A further channel-associated function is that of a programmed amplitude desynchronization, necessary when more channels are used concomitantly in order to diversify the perception thereof by the CNS, as well as supplementing noise simulation.

This desynchronization is based on a second AM-type modulation; but, unlike that operated in the Synt module 106, which works in a synchronic and parallel manner on all channels, this second amplitude modulation is of local type, and is cyclically active in sequence only on one channel at a time. The rate of this second amplitude modulation is equal to about 8% of the reference value of voltage inputted to the manual-adjustment potentiometer, which is automatically affected thereby. Maximum duration of the modulation, cyclically repeated in sequence on each of the n channels, is of about 40 mS.

The channel module 108 may be repeated to increase the number of outputs available for the user. Therefore, it is possible to provide the use of one or more channel modules 108 (preferably 5 or more), all exactly alike and driven as described above.

Hence, for "non-pain" information strings, the system 100 provides a time sequence of packets and pauses with the modulation characteristics described above.

Figure 8A:
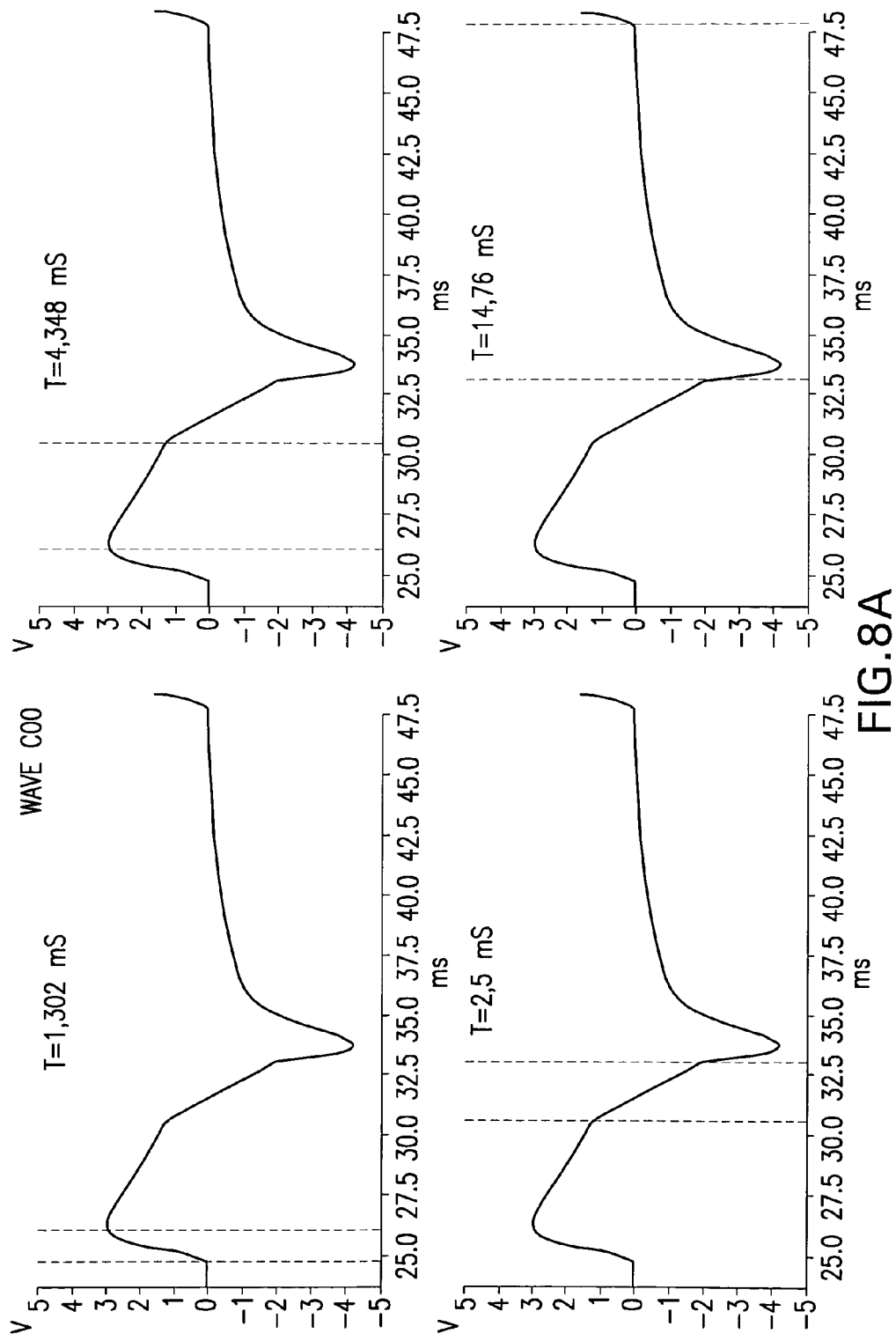
FIGS. 8A to 8P are graphs representing the pattern over time of the waveforms as processed and applied to a patient.
Figure 8B:
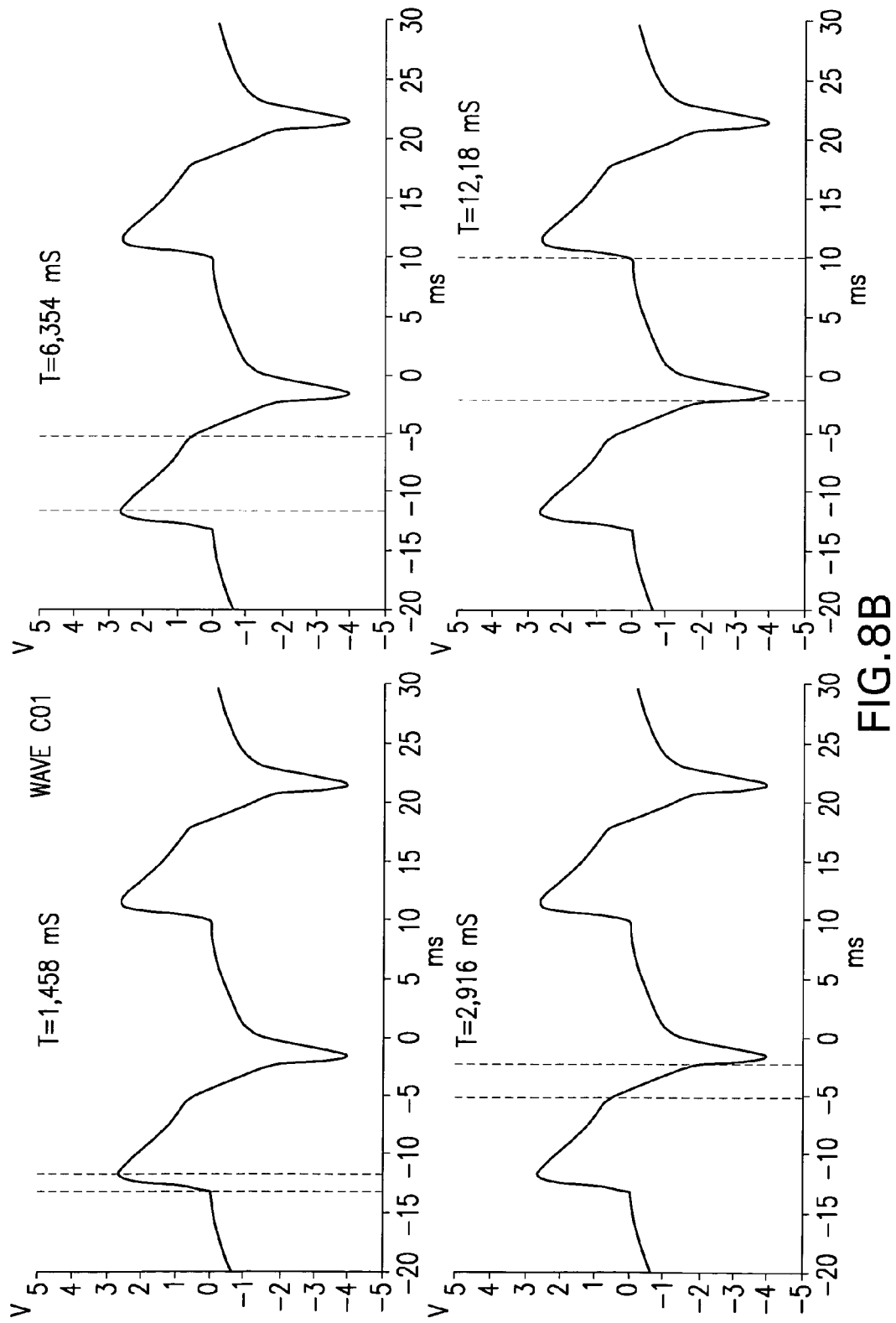
Figure 8C:
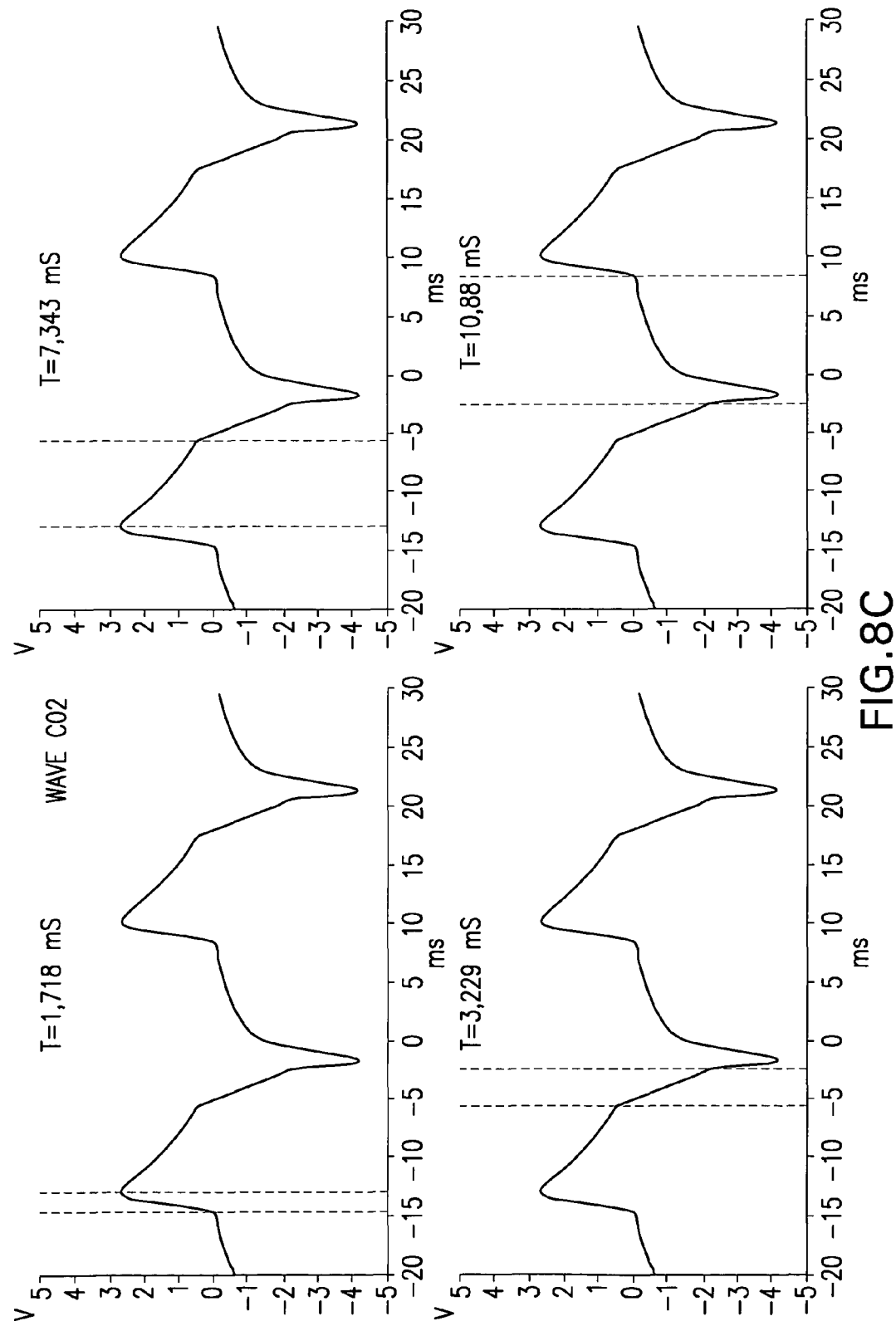
Figure 8D:
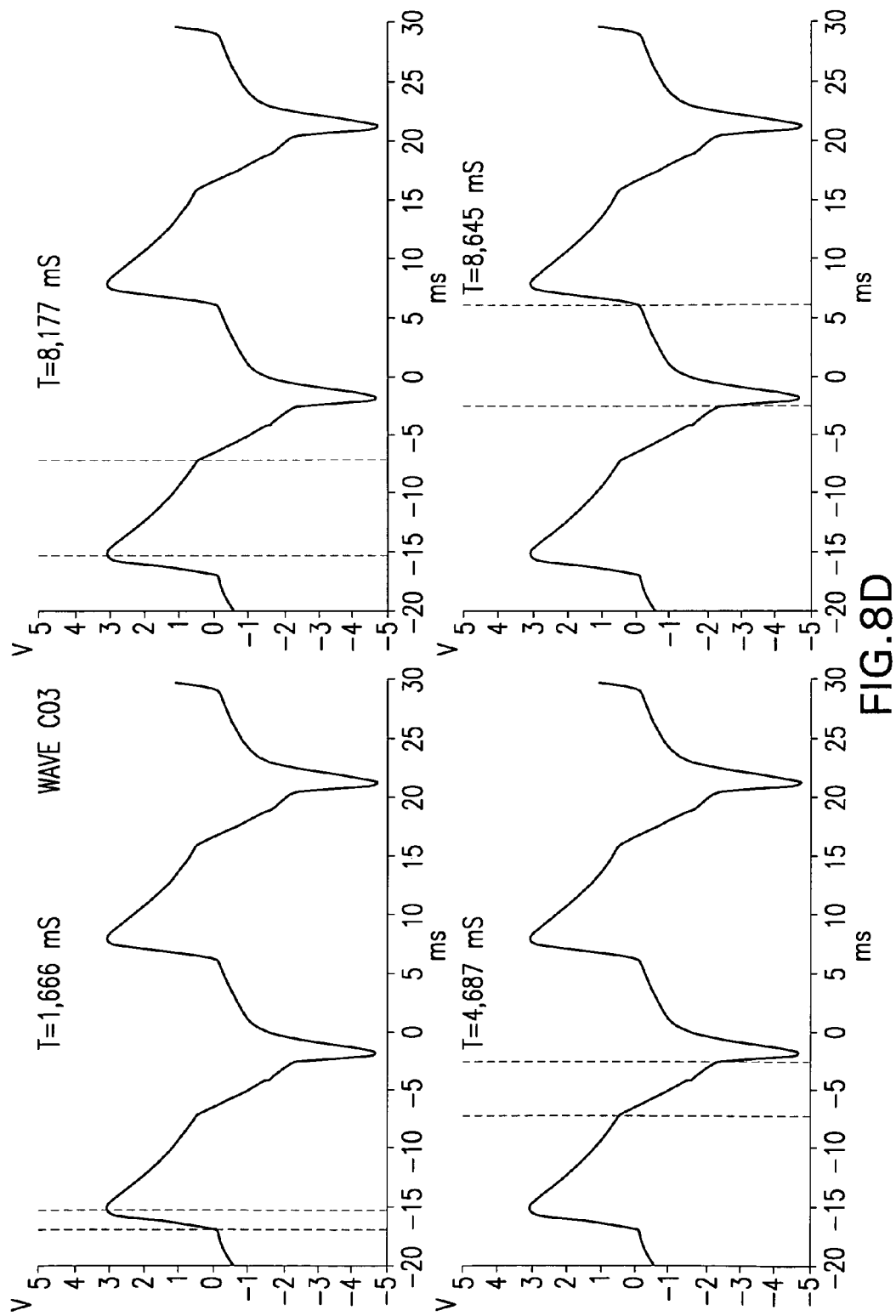
Figure 8E:
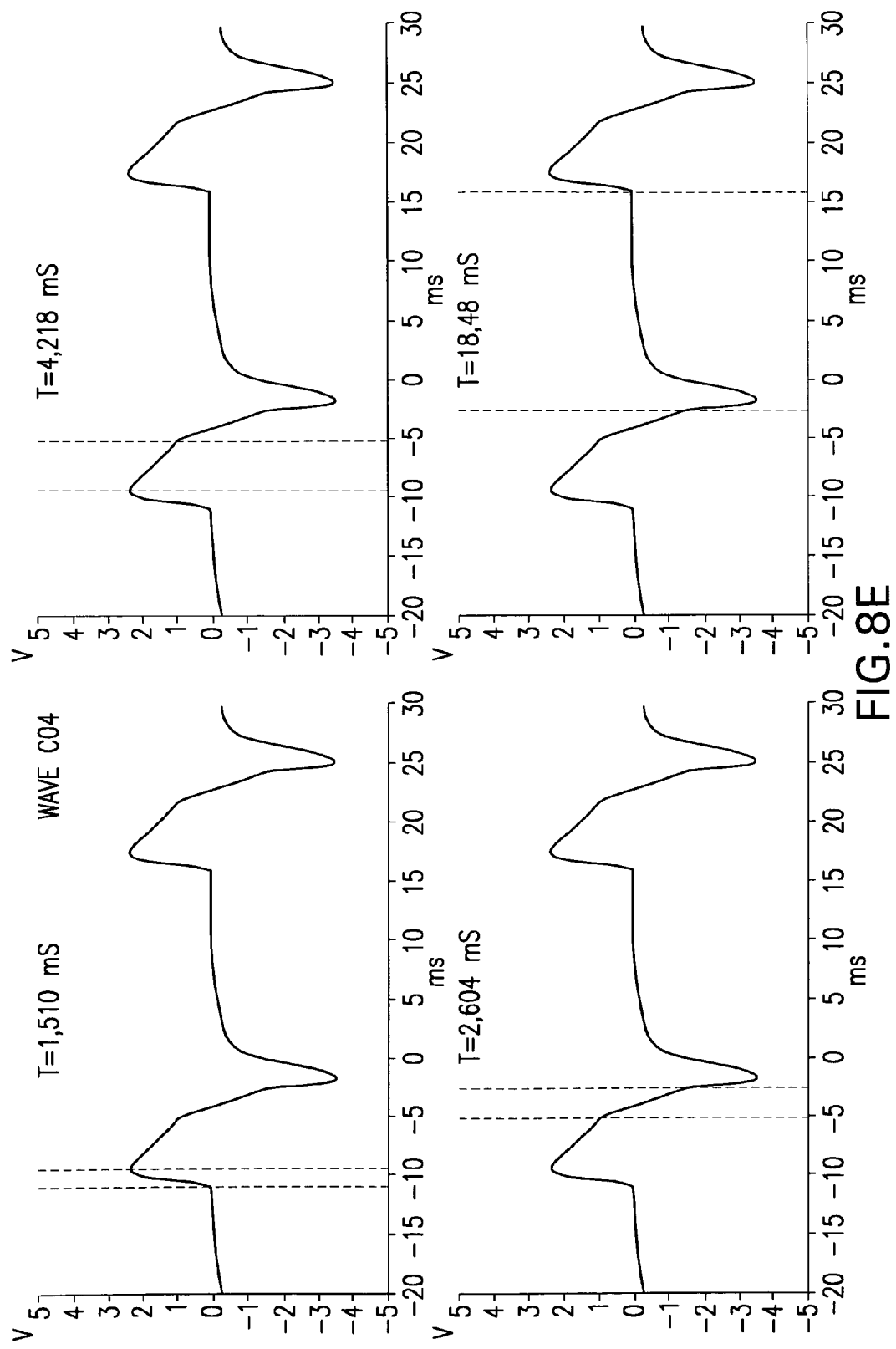
Figure 8F:
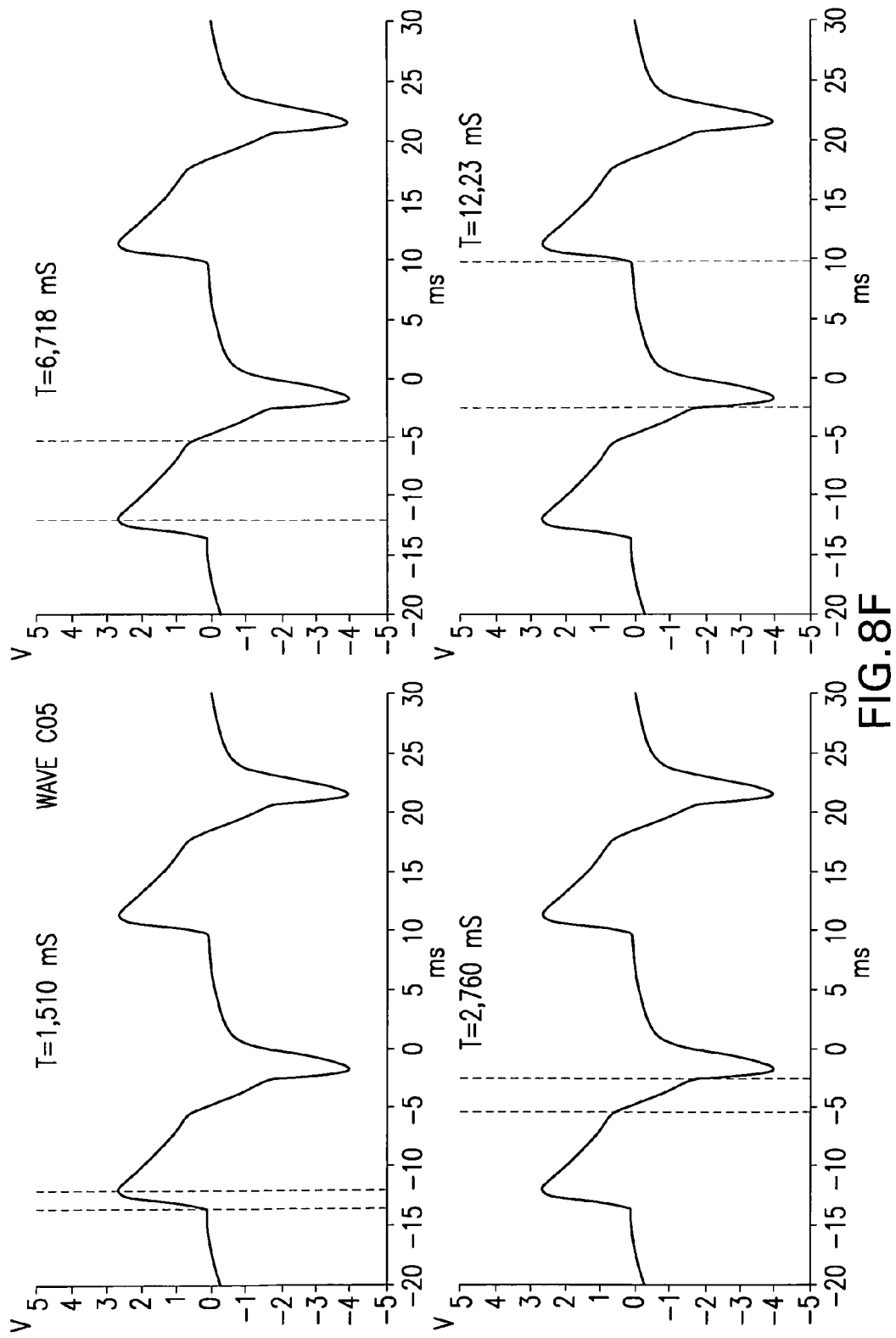
Figure 8G:
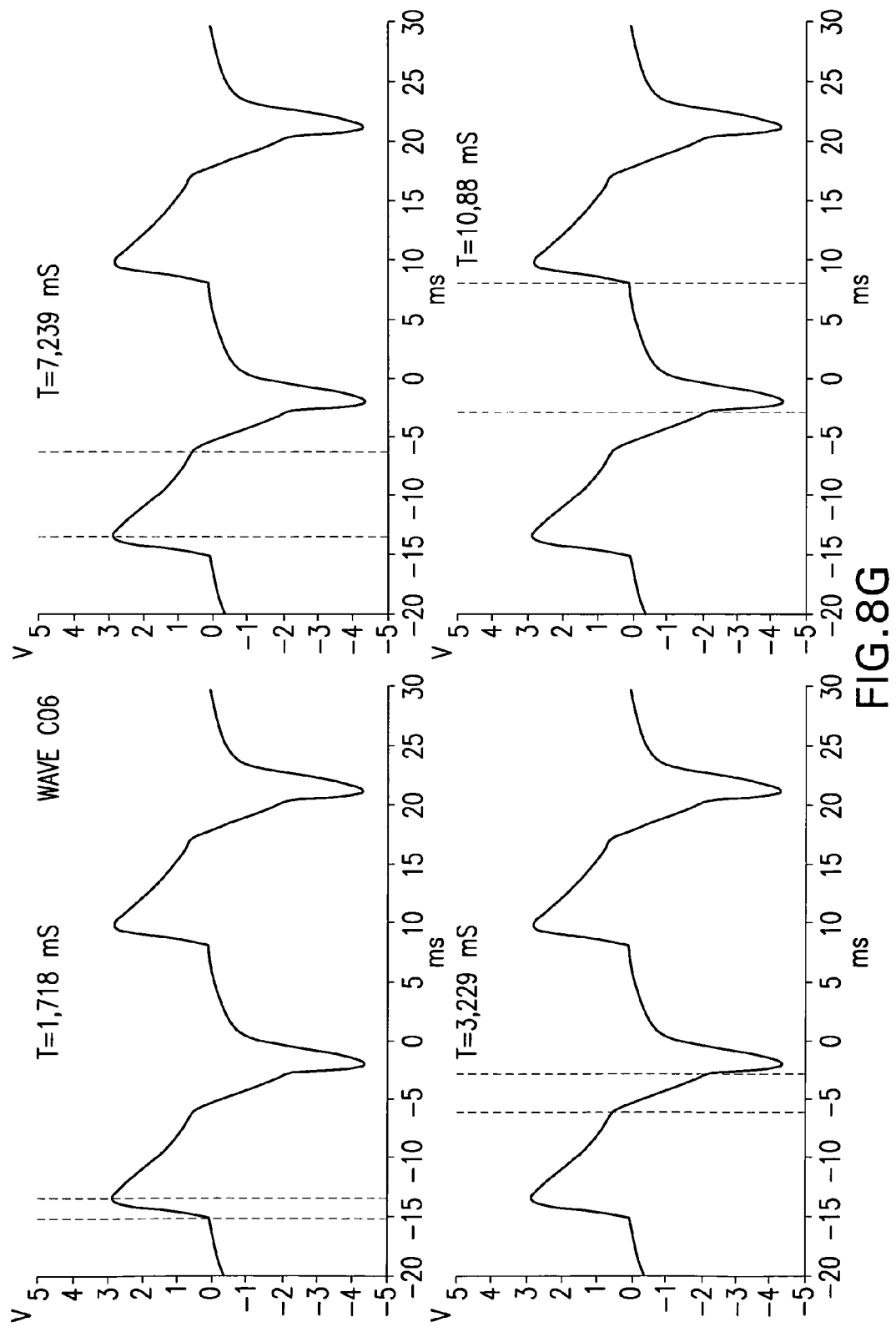
Figure 8H:
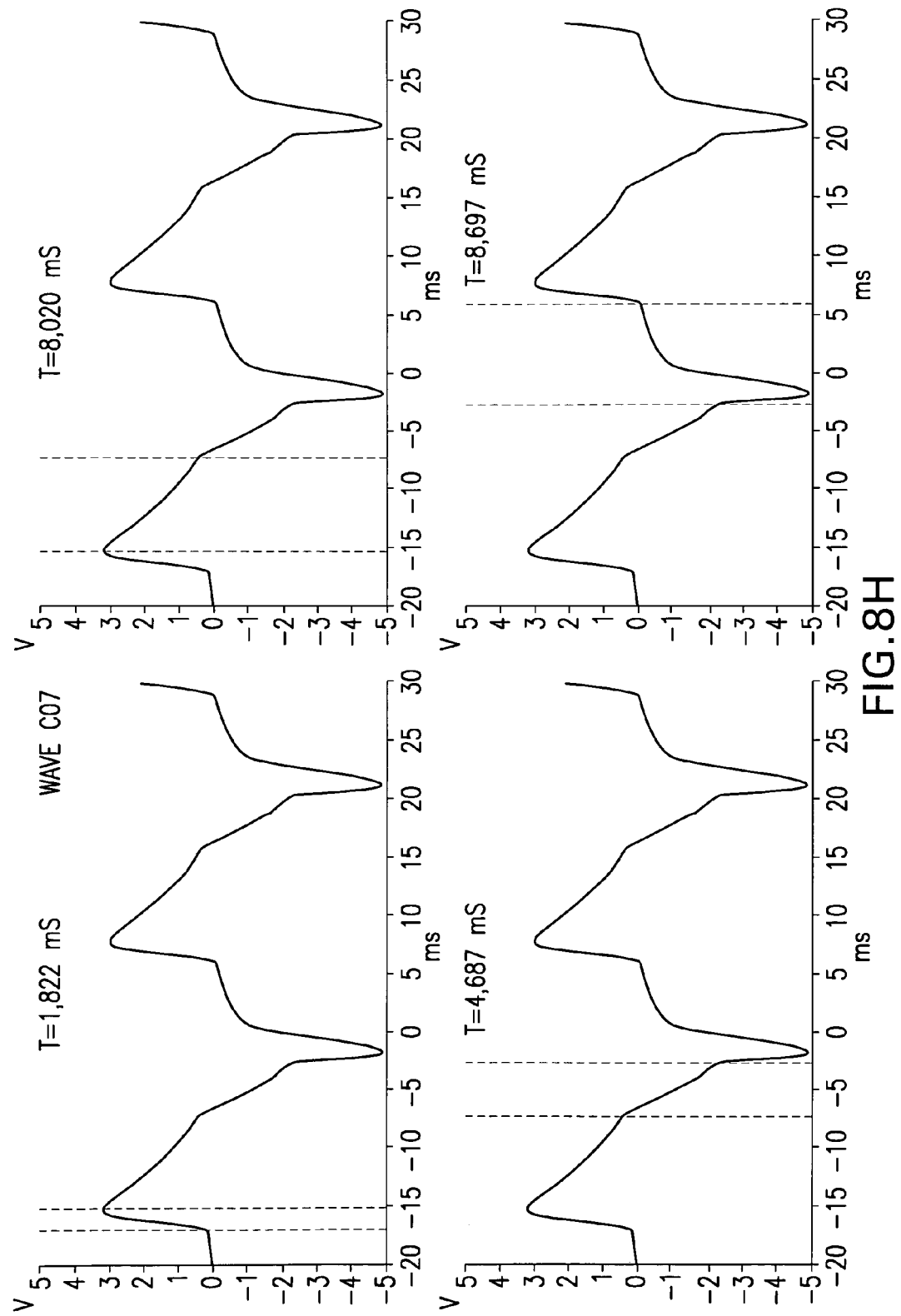
Figure 8I:
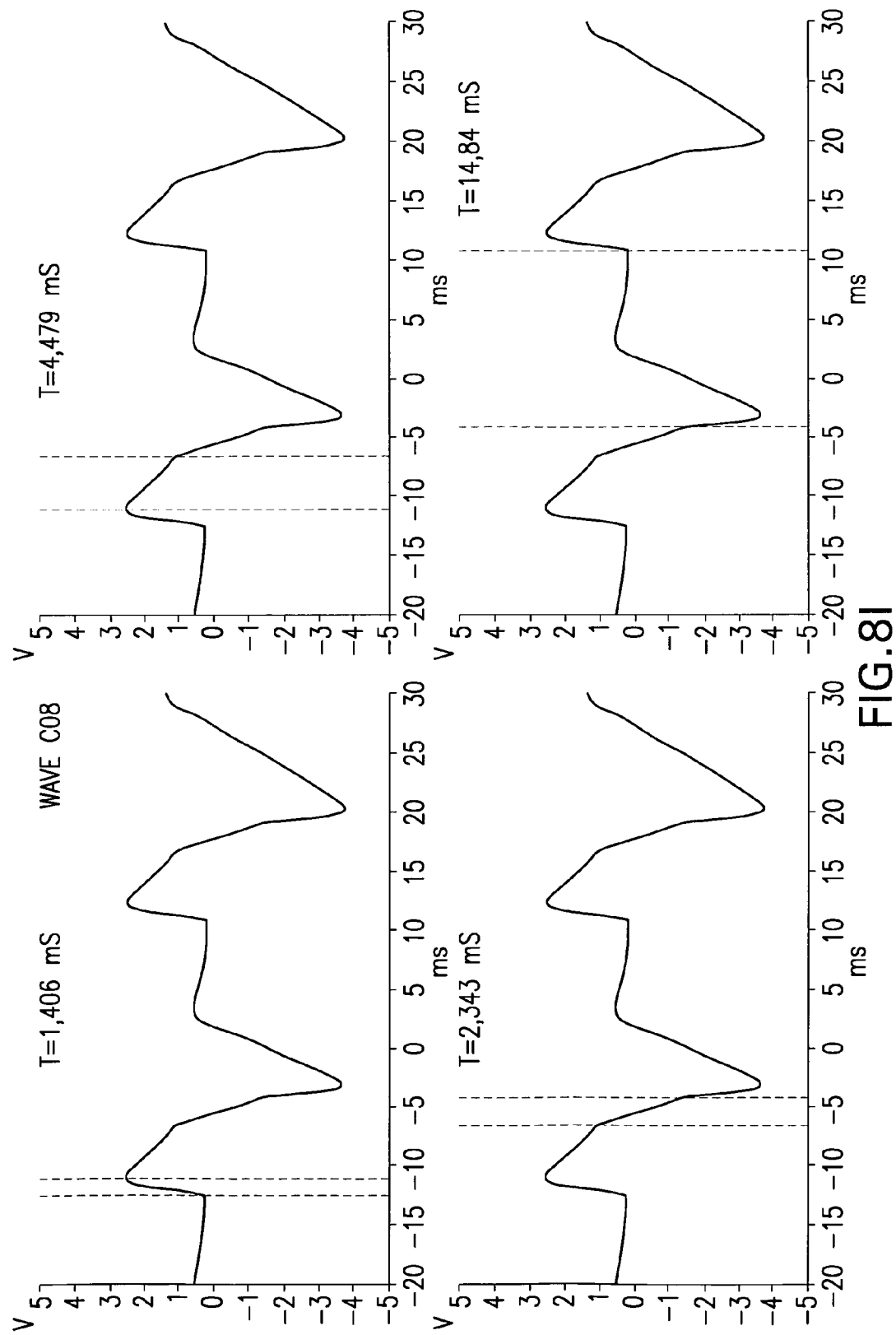
Figure 8J:
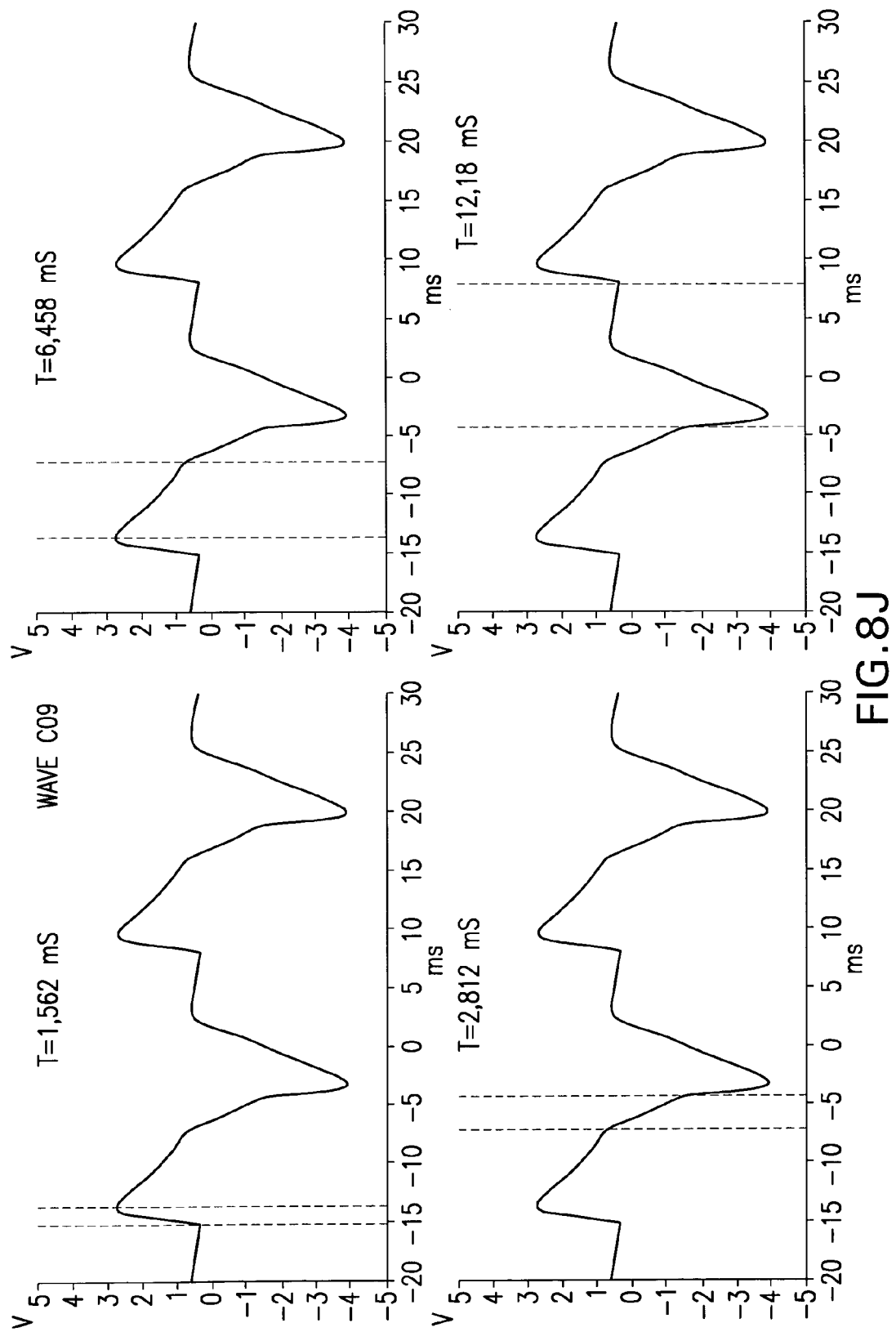
Figure 8K:
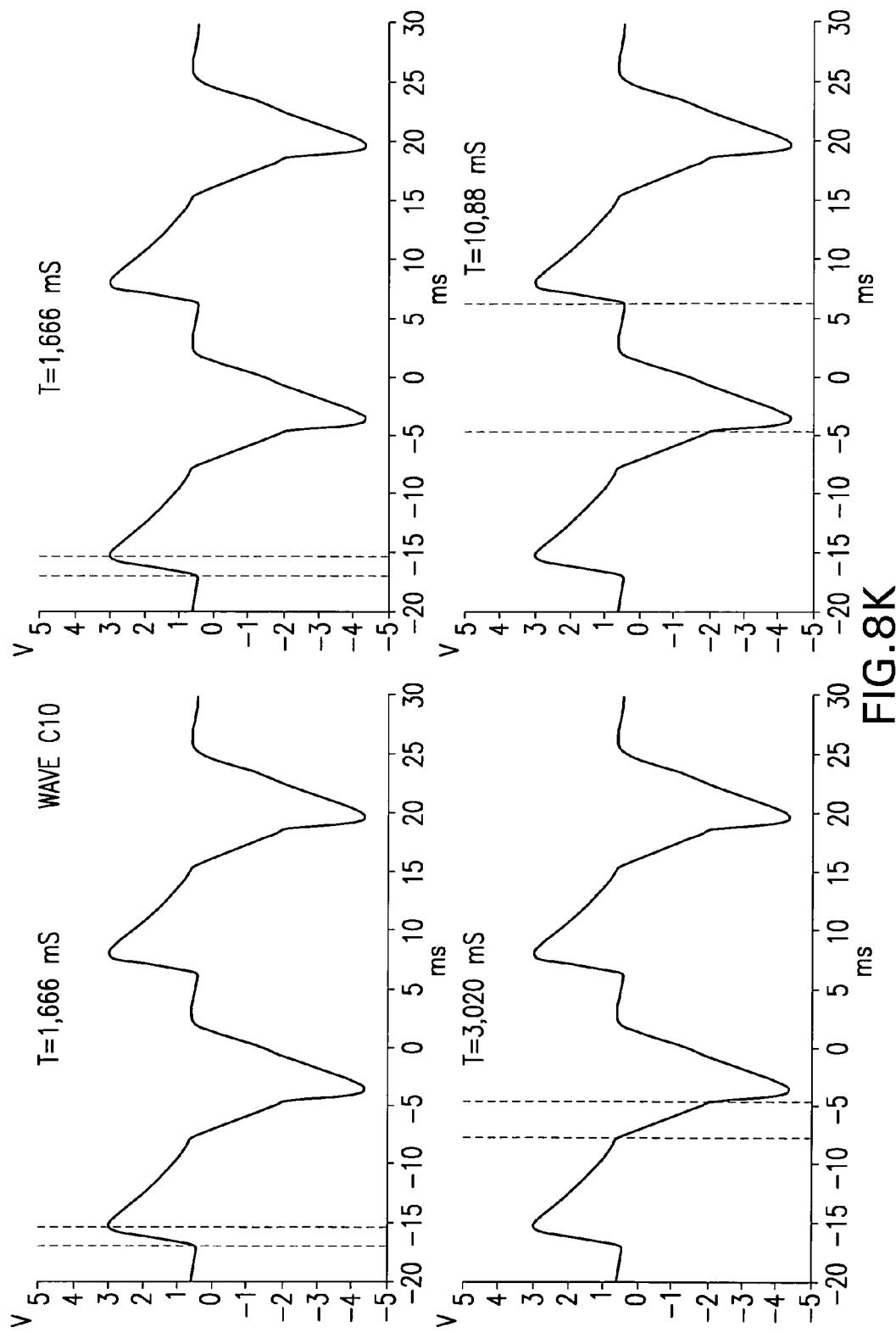
Figure 8L:
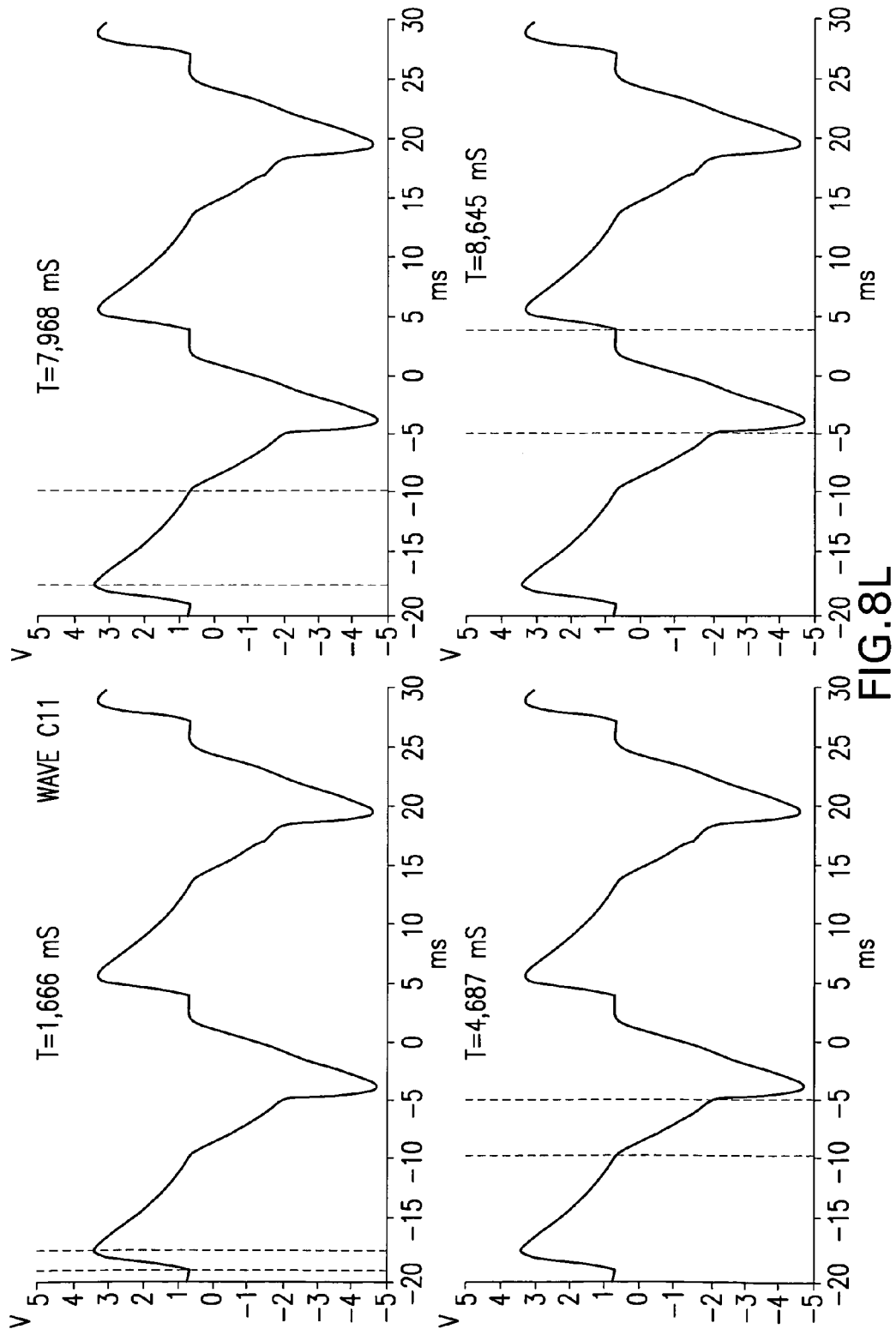
Figure 8M:
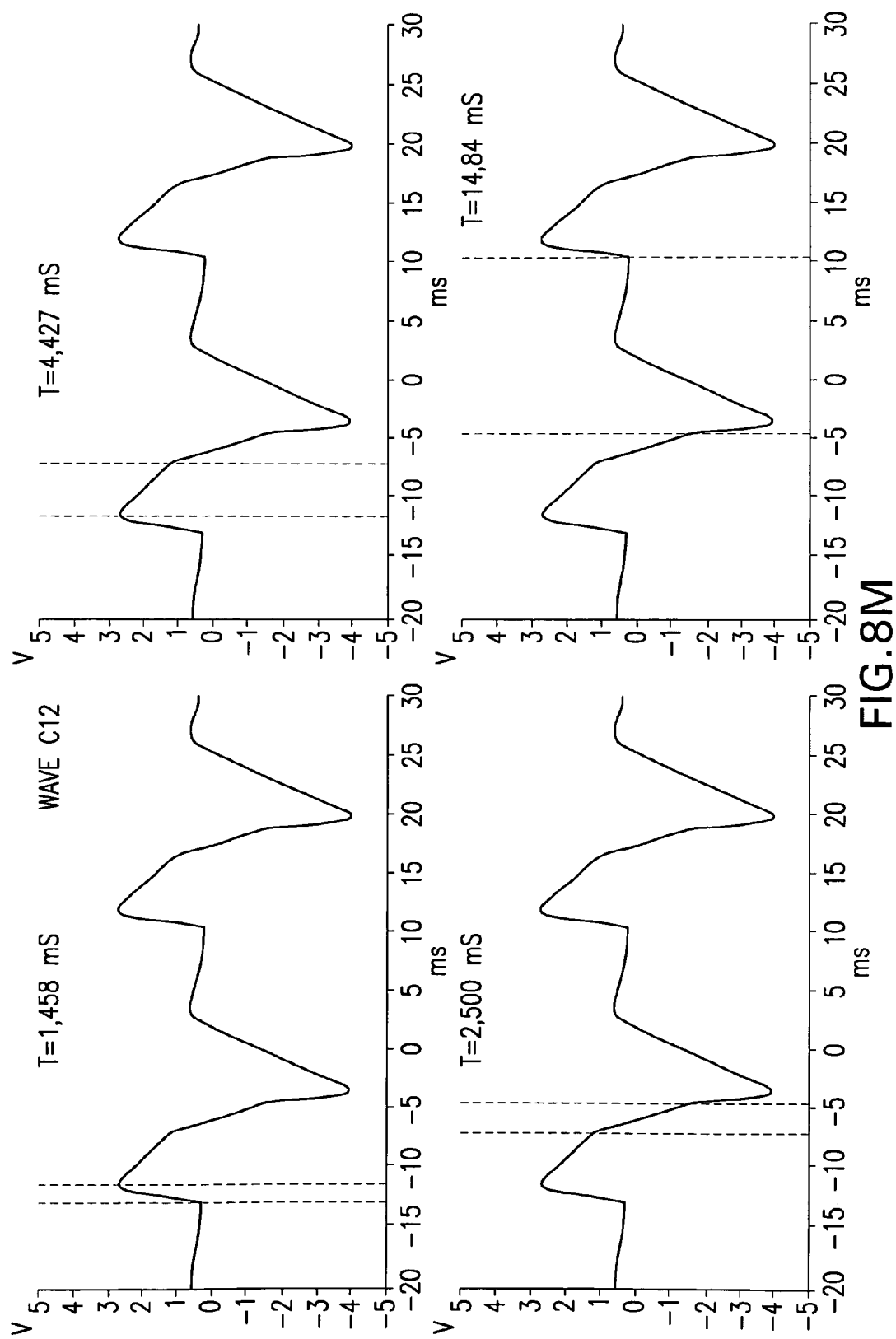
Figure 8N:
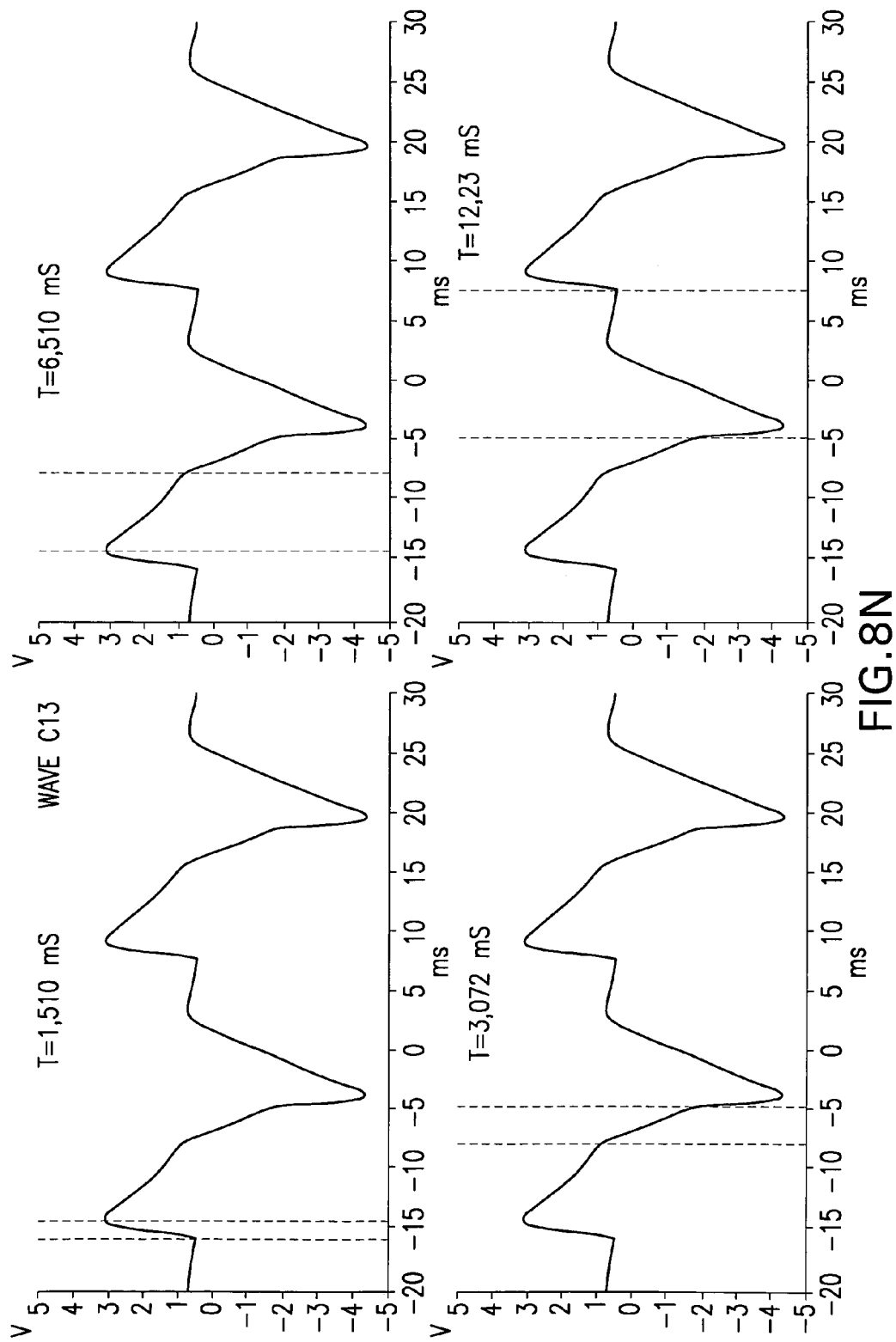
Figure 80:
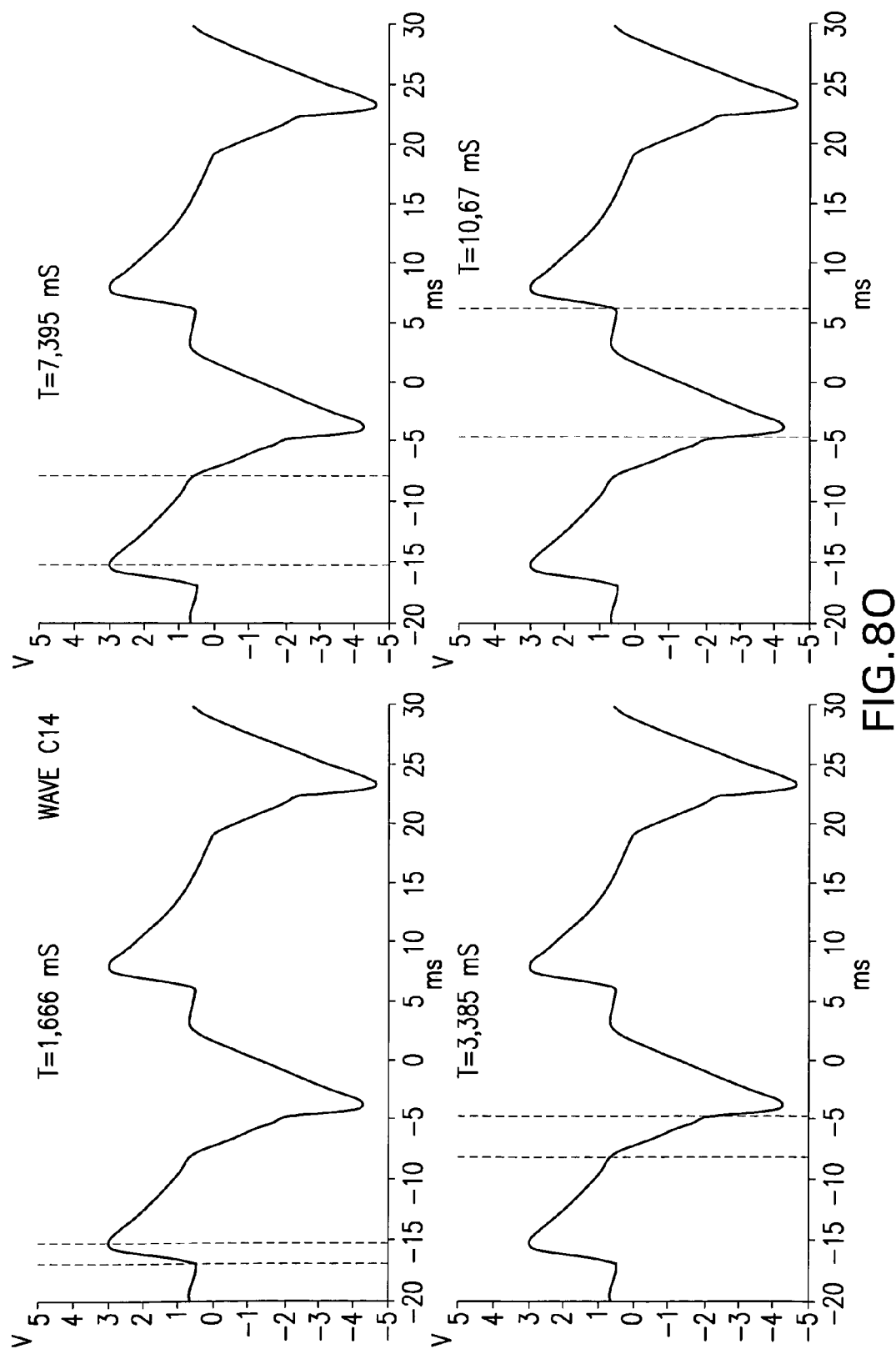
Figure 8P:
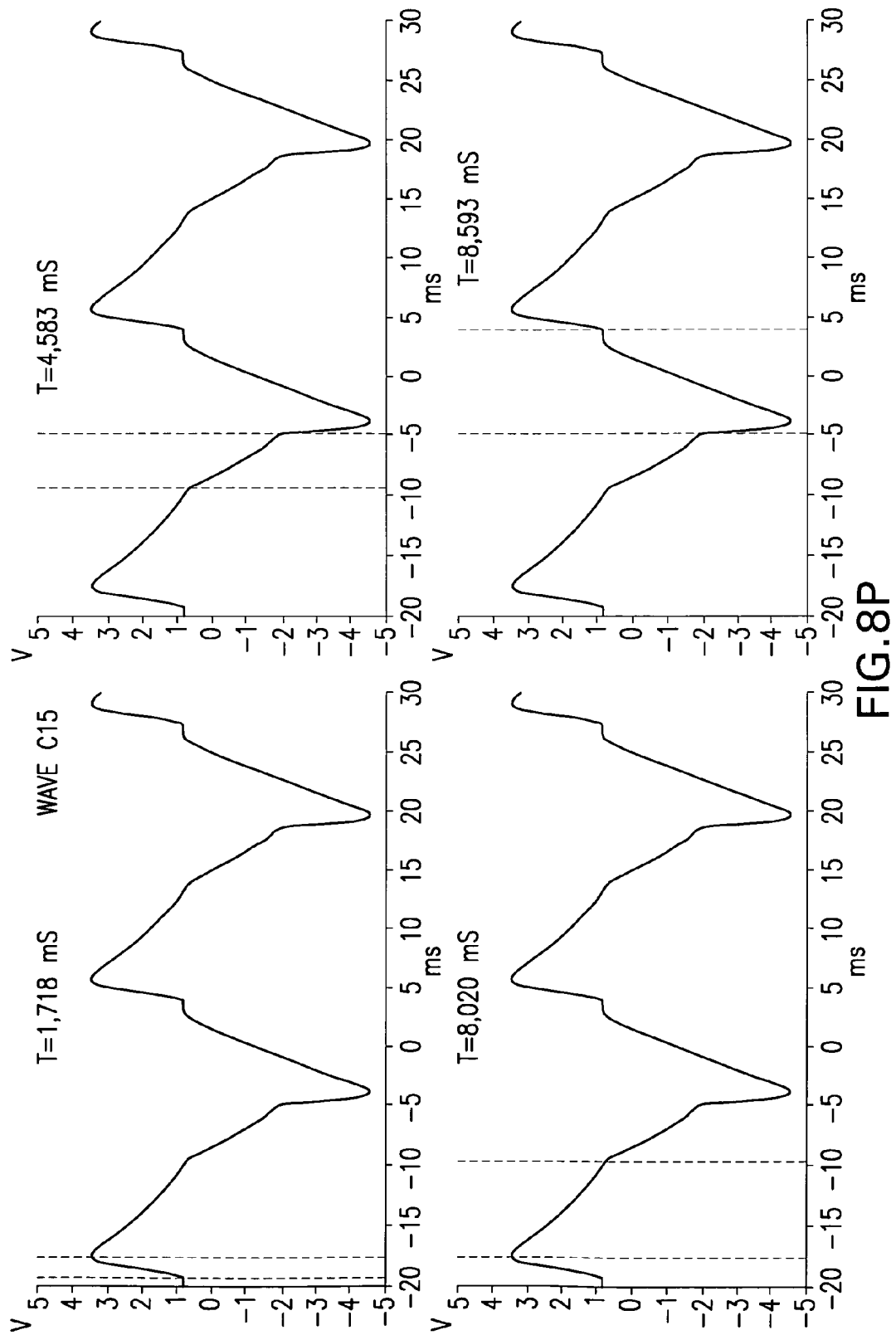

The waveforms denoted by C00 to C15, graphically illustrated in FIGS. 8A to 8P, refer to the real output on the patient.

For clarity's sake, the waveforms reported in FIGS. 8A to 8P are devoid of the modulations required to simulate the noise of the endogenous nerve conduction line, modulations anyhow not substantially varying the geometry thereof.

Moreover, by means of suitable digital signaling incoming from the channel modules 108, the Main module 104 can also check correct operativeness and any presence of critical failures.

Patient safety is ensured by three levels of simultaneous circuit responses in case of operation anomalies, operative errors and failures.

A first level of response is of software type, carried out through the monitoring of suitable signaling read by the Main module 104. A second level of protection is internal to the channel module 108, and is based on responses directly slaved to wired logic, therefore not sensitive to any program execution blocking. A last level of protection is of passive type and ensures, also in case of serious failures, non-exceeding of limit currents for the patient, thanks to the output resistor network, a branch of which is variable by means of the varistor.

From a therapeutic standpoint, the present technology is indicated in all cases of pain such as severe-grade, chronic, drug-resistant, resistant to opiates, TENS, implanted stimulators, of benign and oncological type.

In the envisaged conditions of correct use, detailed hereinafter, analgesia is very rapid; upon starting the treatment, only a few seconds are needed to attain complete disappearance of the perception of pain, even for maximum intensities and no response to opiates. A prolonged use increases treatment effectiveness, with a gradual raise in the pain threshold outside of the same treatment and an increase in the analgesic effect duration measured in hours.

During testing, no undesired effects were found under envisaged use conditions.

An apparatus according to the present technology, in order to apply the analgesic therapeutic method, may be used in a hospital context as well as in an outpatient care unit one, even in an autonomously patient-managed way, but of course always under a doctor's supervision.

For many conditions, optimal treatment time, ensuring immediate effectiveness as well as analgesia duration, is 30-45 minutes.

In case of oncological pain, save specific reasons, patient treatment should be performed when required.

It is advisable to reduce with a scaling down mode and, as far as possible, the analgesic support of pharmacological type, when used. It has been tested that a complete suspension of analgesic drugs is viable in the majority of cases affected by very severe-grade or untreatable oncological pain, whereas in other cases, it is possible to greatly reduce the dosage of opiates, or those can be replaced by other less invasive drugs. This precaution is required not only to optimize the effects of the treatment, but also to improve the patient's quality of life, a main aim of palliative care.

In the case of mild pain, the treatment should envisage (optionally repeatable) cycles consisting of 10 treatment sessions with a 5/week frequency. When possible, the sessions may be consecutively performed when required.

It is advisable to reduce with a scaling down mode and, as far as possible, the analgesic support of pharmacological type, when used. A special case is that of patients using anticonvulsants. In this case, responses are usually slower and less stable over time. The reduction in efficacy is likely due to depression of cerebral bioelectric activity induced by the anticonvulsant drug, a likely antagonist of the active principle of the method. Anticonvulsant scaling down, especially when too brisk, can cause rebound effects. Optimal adjuvant drugs, if required, generally belong to FANS or the paracetamol category.

i) Opiate use does not reduce effectiveness during treatment; yet, if not eliminated during the therapy cycle, opiates can prevent a favourable upward remodelling of the pain threshold, and produce less stable responses over time at the end of the cycle.

The therapy subject-matter of the present technology constitutes an extraordinarily effective pain control system as long as it is used correctly, following the rules illustrated hereinafter. It has been experimentally observed that in the near-totality of cases lacking a satisfactory response under treatment, this was exclusively due to an erroneous on-skin deployment of the electrodes 160, or to a faulty assembly thereof. Upon removing the faults, effectiveness was restored.

For a good effectiveness, it is preferable to use single-use 5-cm electrodes 160 of ECG-type or of equivalent surface. Electrodes that are too small can cause rashes, and electrodes that are too big can engage more nerve ends than required. If the surface to be treated is wide, plural channels can be used.

Each single-use electrode 160, even if pretreated, should preferably be covered with conductive gel on the spongy surface, using greater amounts if the skin is very dry.

Body portions where the electrodes 160 are to be positioned should not be cleaned with alcohol or other dehydrating substances and ought to be well-dried to allow correct electrode 160 adhesion. A bad contact, beside making the treatment less effective, may cause bothersome rashes.

Lastly, it is certainly preferable not to position the electrodes 160 on irritated or wound zones or on biological fluids and, as a general rule, to connect wires on the electrodes 160 only after having well positioned the latter.

Figure 9:
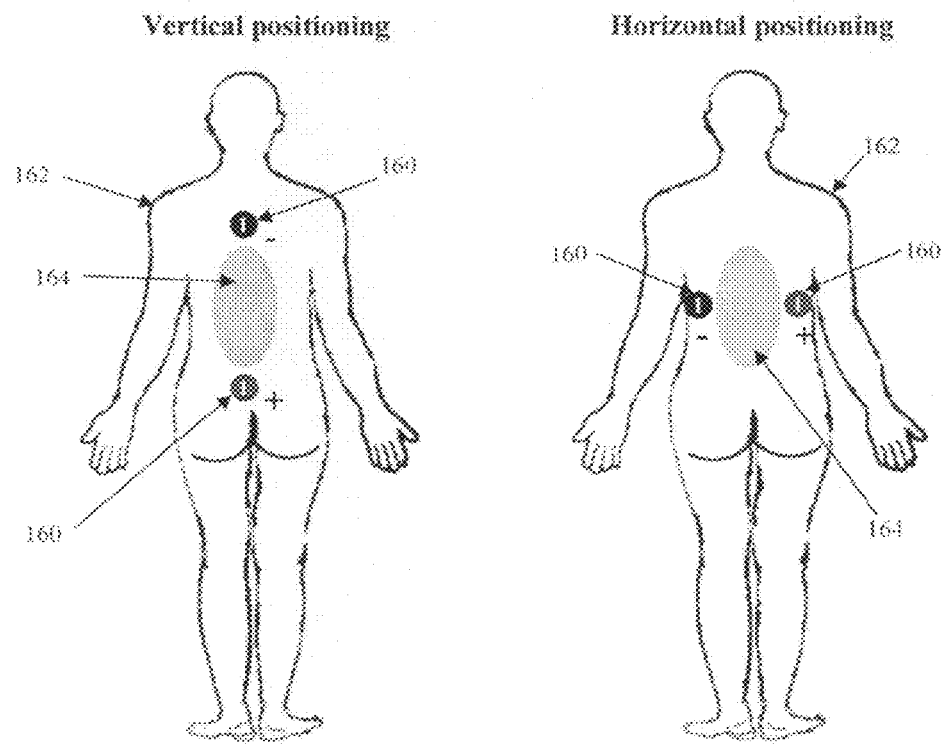
FIGS. 9 to 11 show examples of electrode arrangement on a patient's body, according to the method of the present invention.

Save from specific neurological damages, the electrodes 160 are to be arranged "immediately beside" the painful area, setting them vertical with respect thereto when possible, and anyhow preferably not positioning the electrodes 160 inside the painful area. FIG. 9 shows two examples of positioning of a pair of electrodes 160 on a schematic person 162, where the electrodes 160 are positioned about a painful area 164.

Imagining a straight line passing through the two points represented by the electrodes 160, the same should approximately pass at the center of the area 164 of maximum pain. When required, plural channels 108 (e.g., electrodes 160) can cover very wide painful areas 164, observing the electrical phases, which are identifiable e.g., by a conventional polarity marked, for instance, by a different colour of the electrodes 160 (e.g., red and black) or otherwise (+/−, etc.). Therefore, in general, all electrodes 160 of a same kind should be positioned on a same side. For simplicity's sake, in the figures electrodes 160 are conventionally identified by symbols "+" and "−".

Hence, if plural channels 108 are used, all vertical positionings should have at the top and bottom the electrodes 160 of the same type of each channel 108. The same for horizontal positionings, which for each channel 108 should have electrodes 160 of the same type both on the right and the left, under pain of loss of effectiveness.

Figure 10:
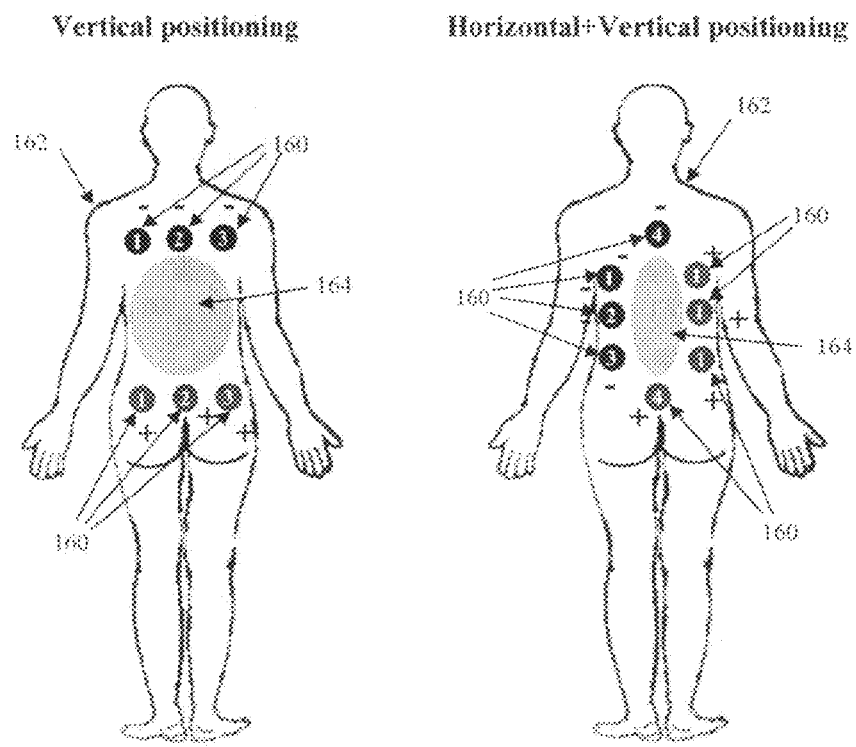

Moreover, by following the guidelines above, it is possible to perform mixed horizontal and vertical positionings, as illustrated in the representations of FIG. 10. Other configurations can also be effective.

In fact, at times finding the right arrangement of the electrodes 160 can be difficult owing to innervation modifications due to neuropathy, traumas, surgery, or other chronicization-induced modifications of the pain system. In this case, it is necessary to proceed by redundancy, and by subsequent attempts, taking into account that it can be immediately understood when a positioning is correct, as pain immediately disappears in a correctly treated zone. By using such feedback, it is possible to solve even the most complex situations thanks to the immediate confirmation on the pain symptom.

In some cases, difficulties may be found in identifying pain-free zones useful for the treatment. In these difficult situations, advanced positioning strategies may be used, which usually solve the problem. A first strategy, especially useful in facial pain, is that of using contralateral pathways. Generally, in a case of lack of response, it is possible to use an homolateral positioning for one of the two electrodes 160 of the channel 108, and a contralateral one for the second coupled electrode 160.

Figure 11:
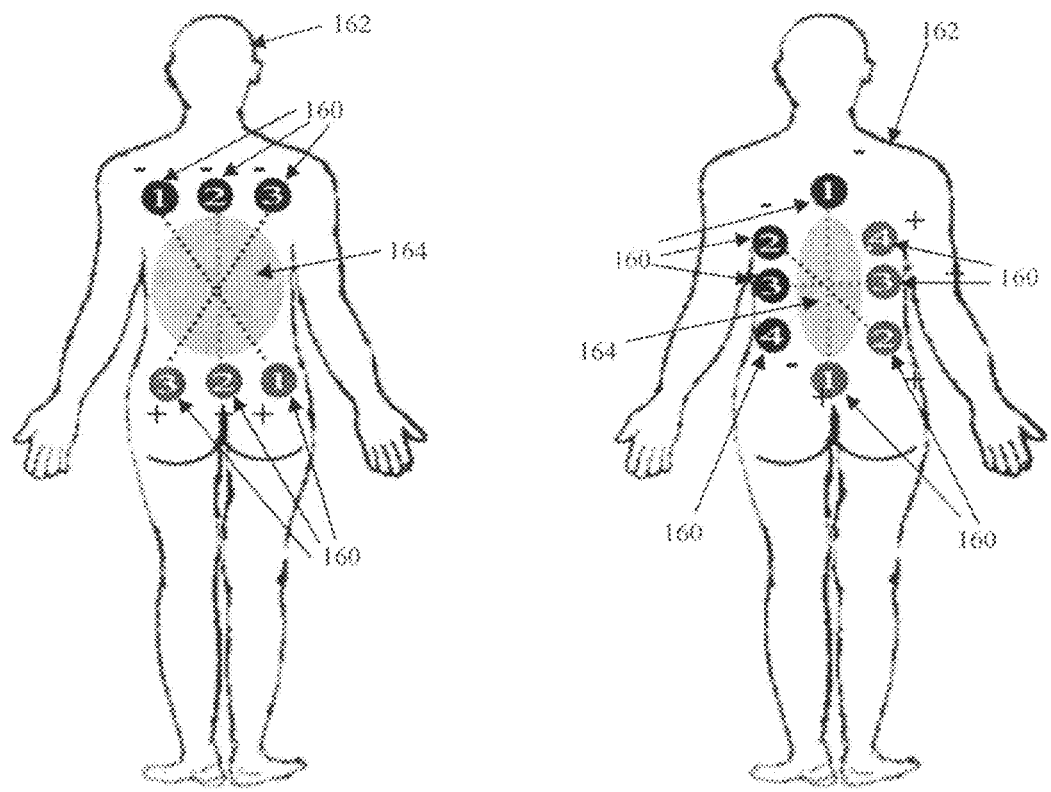

Another type of positioning often solving difficult situations in a very simple manner, is the X-crossed one, in conjunction, when required, to the traditional horizontal/vertical positioning using the other free channels 108. The X-crossed positioning is illustrated in the representations of FIG. 11.

Of course, it is understood that, beyond the exemplary illustrations shown, all described positioning types may validly be applied to any body area.

It should be borne in mind that the sign of a correct treatment is only the disappearance of pain in the treated areas. For this reason, it is not possible to treat pain prior to its appearance.

Moreover, in the case of pains appearing only in certain positions, it is preferable to ensure that the positioning and the checking of its effectiveness always occur in conditions in which pain is present, otherwise the therapy cannot be deemed as certainly effective. Once certain of the correct positioning, the patient could take on the positions he/she prefers for getting on with the treatment.

In addition, in difficult cases, it is preferable to always test one channel at a time, in sequence, by positioning one pair of electrodes 160 at a time and making sure of its analgesic effectiveness. If the overall time of the entire treatment has greatly reduced that of residual therapy, it suffices to set to zero the levels of each channel 108 without modifying the positioning any more, then stop the therapy with the appropriate controls, and restart the therapy to correctly perform an entire treatment.

In most applications, beneficial and positive effects are found already after a very short treatment, almost instantly. However, a treatment of at least 30 min. is preferable. In cases of very intense pain, typically oncological, the optimal value is to be brought preferably to 45 min.

The treatment starts automatically when the level of any one of the channels 108 rises, and automatically stops once the preset time (modifiable by setup if necessary) expires.

The treatment is completely automated and requires no individual setting of wave parameters, like, e.g., frequency, duty cycle, scanning, etc., also because irrelevant in the active principles used. The sole manual regulation required is that of the stimulus amplitude, to adapt it to the patient's individual sensitivity.

For this purpose, channel amplitudes should preferably be regulated to the limit of the individual tolerability threshold that the patient under treatment subjectively feels.

Preferably, levels should initially be regulated during the first instants of treatment, preferably within the first minute, and adjusted once the first minute is expired, when the apparatus is in a steady state, and thereafter whenever the stimulus is not correctly sensed anymore on both electrodes 160 of each channel 108 involved.

If at treatment start, the signal is sensed only on one of the two electrodes 160 of each channel 108, it is necessary to stop the treatment and modify the positioning of the electrodes 160.

In muscle pain, for improved effectiveness, at times it may be preferable that, beside what is expressed in (generally sufficing) indications on positioning, when certain of a correct positioning current flow be sensed between electrode pairs 160 of the same channel 108. If nevertheless the response is not good, then it is preferable to use plural channels 108 for the same area.

In order to prevent rebound effects during or after the therapy, it is preferable to always make sure that the patient does not report, in correspondence to one or more electrodes 160, a painful and/or extremely unpleasant sensation, expression of a residual recruiting of fibers in connection with the painful area. This sensation is easy to recognize, as generally a synthesis of "non-pain" information (i.e., the desired one) is optimally tolerated, and the sensation associated thereto is often defined as pleasant. In this case, the electrodes 160 are to be repositioned slightly farther from the selected spot, until eliminating the problem and obtaining effective analgesia. Noncompliance with this indication may result in undesired rebound effects during or after the treatment.

A further relevant check to understand whether the positioning is correct under an electric and functional standpoint, is that of asking the patient under treatment, after activation of each channel, if perceived pain sensation varies in that sector. In fact, regardless of initial pain intensity, which may also be very high, the answer should always be negative (i.e., no pain perception=optimal positioning) already after just a few seconds from the correct adjustment of the stimulus intensity.

If, upon complete activation of all channels 108, the patient still reports pain, coverage is not complete and the therapy will yield effects significantly lower than what can be done. Less than complete analgesia depends on a mismatching of involved innervations, or by a very wide and incompletely treated area 164. In the first case, the electrodes 160 should be better positioned, as explained in the various positioning strategies. In the second case, other channels 108 should be used, as explained above.

If positioning cannot be modified and after some minutes of treatment—preferably after about 5 min—perception of pain persists, even though dimmed, the result will not be good. During treatment there should always be a decrease in the perception of pain, even when the latter is of an extremely high degree.

If pain—even though not present during the application—recurs (even in a dimmed form) at the end of the treatment, or reappears a few minutes later, application has to be repeated making sure that all of the above-described steps have been complied with.

Figure 12A:
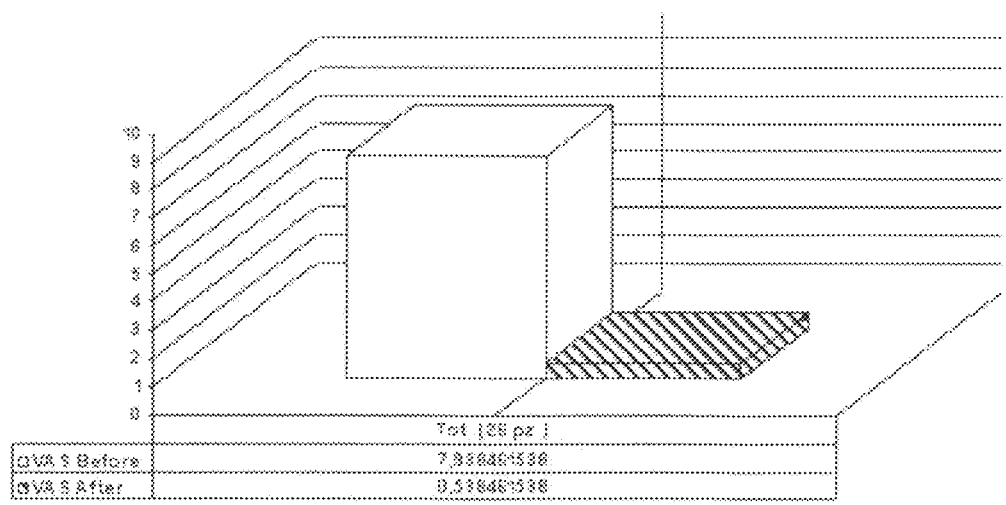
FIGS. 12A to 12C are graphs showing the results of performed testing.
Figure 12B:
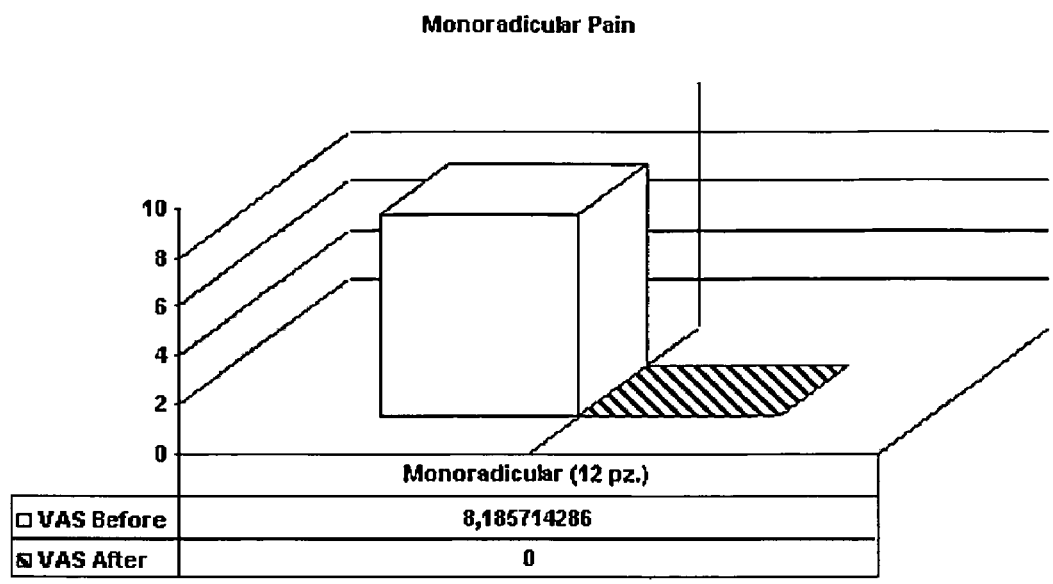
Figure 12C:
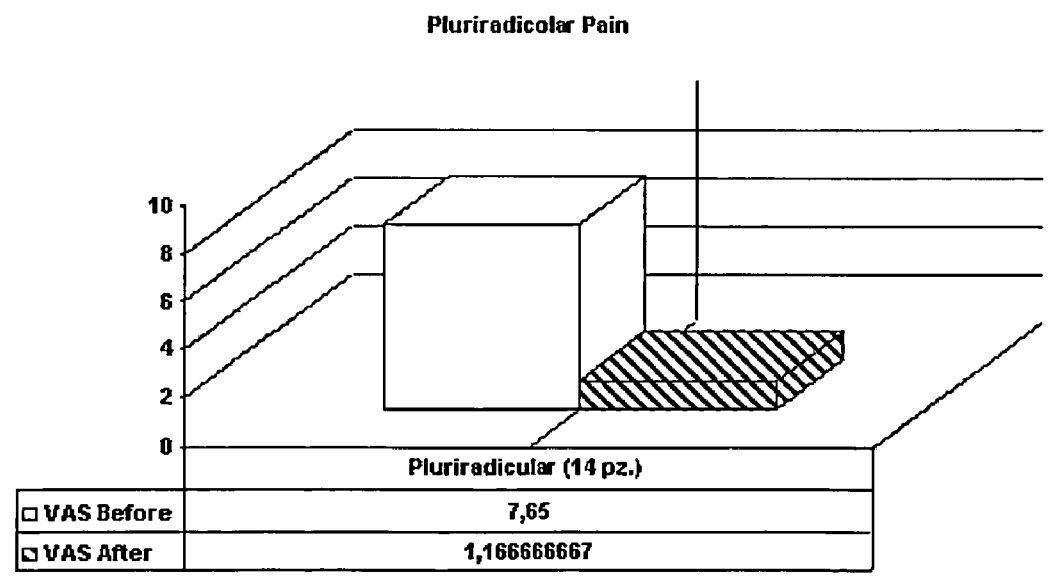

For completeness' sake in the description, though by way of example and without limitation, some results of tests performed are reported in the graphs of FIGS. 12A to 12C.

Referring to FIGS. 12A to 12C, the data relates only to chronic pain non-responsive to other protocol therapies including opiates, TENS, implanted electroanalgesia. Pain intensities were measured on a VAS scale from 0 (e.g., no pain) to 10 (e.g., unbearable pain), and refer to a treatment cycle consisting of 10 applications. From an analysis of said data, it could easily be assessed how the latter provide clear evidence of treatment effectiveness.

The present invention has been hereto described with reference to a preferred embodiment thereof. It is understood that other embodiments might exist, all falling within the concept of the present invention, and all comprised within the protective scope of the claims hereinafter.

The invention claimed is:

1. An apparatus for suppression of chronic and/or neuropathic pain, the apparatus comprising:
 a main module comprising data storage means and data processing means, said data storage means comprising:
  first parameters $V_i$ corresponding uniquely to a set of sixteen different primitive waveforms S00-S15, each primitive waveform $S_i$ having a periodic and predetermined pattern over lime; and
  second parameters including T-pack$_i$, Freq$_i$, and T-slot$_i$ associated with each of said different primitive waveforms $S_i$,
  wherein said data processing means is adapted and configured to process a data set $B_i$ identifying a sequence consisting of a plurality of at least two of said different primitive waveforms $S_i$ in a time sequence, each of the primitive waveforms of the sequence being processed on the basis of one or more of said second parameters T-pack$_i$, Freq$_i$, T-slot$_i$;
 a synthesizer module comprising means for generating an electric output signal corresponding to said sequence; and
 one or more channel modules $Ch_k$ for applying said electric output signal on skin of a patient's body so that surface receptors in polymodal nerve fibers of a nervous system carry the electric output signal as non-pain information to suppress chronic and/or neuropathic pain.

2. The apparatus according to claim 1, wherein said first parameter $V_i$ comprises amplitude values of each primitive waveform $S_i$ of said set of primitive waveforms S00-S15.

3. The apparatus according to claim 2, wherein each of said primitive waveforms $S_i$ is represented in digital format by the corresponding first parameter $V_i$ of values, expressed in the hexadecimal system:

$V_0$=B6 FE FE FE FE FE FE FE FE FE FE FE FE FE FE EC DA C8 B6 A4 92 80 00 20 40 60 6E 80 80 80 80 80 80 80 80 80 80 80 80 80 80 80 80 80 80 80 80 80 80 80 80 80 80 80 80 80 80 80 80 80, $V_1$=81 B6 FE FE FE FE FE FE FE FE FE FE FE FE FE FE FE FE FE FE FE FE FA EC DE D0 C2 B4 A6 9A 8E 00 20 40 60 6E 80 80 80 80 80 80 80 80 80 80 80 30 80 80 80 80 80 80 80 80 80 80 80 80 80 80 80, $V_2$=81 AA D4 FE FE FE FE FE FE FE FE FE FE FE FE FE FE FE FE FE FE FE FE FE FE FE F0 E2 D4 C6 B8 AA 9C 8E 80 00 20 40 60 6E 80 80 80 80 80 80 80 80 80 80 80 80 80 80 80 80 80 80 80 80 80 80 80 80, $V_3$=81 AA D4 FE FE FE FE FE FE FE FE FE FE FE FE FE FE FE FE FE FE FE FE FE FE FE FE F5 EC E3 DA D1 C8 BF B6 AD A5 9B 92 80 00 20 40 60 6E 80 80 80 80 80 80 80 80 80 80 80 80 80 80 80 80 80 80 80, $V_4$=B6 FE FE FE FE FE FE FE FE FE FE FE FE FE FE EC DA C8 B6 A4 92 80 00 10 20 30 40 60 70 80 80 80 80 80 80 80 80 80 80 80 80 80 80 80 80 80 80 80 80 80 80 80 80 80 80 80 80 80 80 80, $V_5$=81 B6 FE FE FE FE FE FE FE FE FE FE FE FE FE FE FE FE FE FE FE FE FA EC DE D0 C2 B4 A6 9A 8E 00 10 20 30 40 60 70 80 80 80 80 80 80 80 80 80 80 80 80 80 80 80 80 80 80 80 80 80 80 80 80, $V_6$=81 AA D4 FE FE FE FE FE FE FE FE FE FE FE FE FE FE FE FE FE FE FE FE FE FE FE F0 E2 D4 C6 B8 AA 9C 8E 80 00 10 20 30 40 60 70 80 80 80 80 80 80 80 80 80 80 80 80 80 80 80 80 80 80 80 80, $V_7$=81 AA D4 FE FE FE FE FE FE FE FE FE FE FE FE FE FE FE FE FE FE FE FE FE FE FE FE F5 EC E3 DA D1 C8 BF B6 AD A5 9B 92 80 00 10 20 30 40 60 70 80 80 80 80 80 80 80 80 80 80 80 80 80 80 80, $V_8$=B6 FE FE FE FE FE FE FE FE FE FE FE FE FE FE EC DA C8 B6 A4 92 80 00 04 08 0C 10 16 1C 22 28 2E 34 3A 40 50 60 70 78 80 80 80 80 80 80 80 80 80 80 80 80 80 80 80 80 80 80 80 80 80 80, $V_9$=81 B6 FE FE FE FE FE FE FE FE FE FE FE FE FE FE FE FE FE FE FE FE FA EC DE Do C2 B4 A6 9A 8E, 00 04 08 OC 10 16 1C 22 28 2E 34 3A 40 50 60 70 78 80 80 80 80 80 80 80 80 80 80 80 80 80 80 80, $V_{10}$=81 AA D4 FE FE FE FE FE FE FE FE FE FE FE FE FE FE FE FE FE FE FE FE FE FE FE F0 E2 D4 C6 B8 AA 9C 8E 80 00 04 08 OC 10 16 10 22 28 2E 34 3A 40 50 60 70 78 80 80 80 80 80 80 80 80 80 80 80 80, $V_{11}$=81 AA D4 FE FE FE FE FE FE FE FE FE FE FE FE FE FE FE FE FE FE FE FE FE FE FE FE F5 EC E3 DA D1 C8 BF B6 AD A5 9B 92 80 00 04 08 0C 10 16 1C 22 28 2E 34 3A 40 50 60 70 78 80 80 80 80 80 80, $V_{12}$=06 FE FE FE FE FE FE FE FE FE FE FE FE FE FE EC DA C8 B6 A4 92 89 00 05 09 0E 18 1E 20 22 28 2E 34 3A 40 49 52 5B 64 6D 77 7F 80 80 80 80 80 80 80 80 80 80 80 80 80 80 80 80 80 80 80 80, $V_{13}$=81 B6 FE FE FE FE FE FE FE FE FE FE FE FE FE FE FE FE FE FE FE FE FA EC DE D0 C2 B4 A6 9A 8E 00 05 09 0E 18 1E 20 22 28 2E 34 3A 40 49 52 5B 64 6D 77 7F 80 80 80 80 80 80 80 80 80 80 80 80, $V_{14}$=81 AA D4 FE FE FE FE FE FE FE FE FE FE FE FE FE FE FE FE FE FE FE FE FE FE FE F0 E2 D4 C6 B8 AA 9C 8E 80 00 05 09 0E 18 1E 20 22 28 2E 34 3A 40 49 52 5B 64 6D 77 7F 80 80 80 80 80 80 80 80, $V_{15}$=81 AA D4 FE FE FE FE FE FE FE FE FE FE FE FE FE FE FE FE FE FE FE FE FE FE FE FE F5 EC E3 DA D1 C8 BF B6 AD A5 9B 92 80 00 05 09 0E 18 1E 20 22 28 2E 34 3A 40 49 52 5D 64 6D 77 7F 80 80 80.

4. The apparatus according to claim 1, wherein said data storage means and said data processing means generates said data set $B_i$, in digital format, each data set $B_i$ comprising at least:
 a first portion identifying a selected primitive waveform $S_i$ to be subsequently repeated at least twice in said sequence, forming a packet Pack$_i$;
 a second portion identifying a frequency value Freq$_i$ to be associated with said selected primitive waveform $S_i$ in sequence; and a third portion identifying a First time duration value T-slot$_i$ to be associated with a pause interval, subsequent to said packet Pack$_i$ and wherein said data storage and processing means further calculate a second time duration value T-pack$_i$ to be associated with the duration of add packet Pack$_i$.

5. The apparatus according to claim 1, wherein said data storage means includes a first probabilistic criterion and said data processing means selects the waveforms S$_i$ with which to compose the sequence on the basis of the first probabilistic criterion.

6. The apparatus according to claim 5, wherein said first probabilistic criterion entails the selection of the waveforms S$_i$ depending on a specific probability, wherein the specific probability varies dynamically for each new packet generated.

7. The apparatus according to claim 5, wherein said first probabilistic criterion is dynamically modified by the data processing means according to a first probabilistic filter stored in the data storage means based on rules stored in the data storage means to vary a selection probability of each of said waveforms S$_i$.

8. The apparatus according to claim 1, wherein said data processing means calculates said second parameters T-pack$_i$, Freq$_i$, T-slot$_i$ for each waveform S$_i$ comprised in sequence on the basis of a probabilistic criteria stored in the data storage program means, from set values and wherein said probabilistic criteria for calculating said second parameters T-pack$_i$, Freq$_i$, T-slot$_i$ are dynamically modified according to probabilistic filters based on corresponding rules set in advance and stored in the data storage means to vary the selection probability of said set values.

9. The apparatus according to claim 1, wherein said main module processes each data set B$_i$ is available as input for said synthesizer module and each data set B$_i$ is represented by a byte.

10. The apparatus according to claim 1, wherein said synthesizer module comprises a microprocessor adapted and configured to read the data set B$_i$ provided by said main module and a first digital/analog converter adapted and configured to convert the electric output signal generated by said second microprocessor into an analog signal corresponding to said sequence, wherein said synthesizer module further comprises a second digital/analog converter adapted and configured to produce a modulating signal based on a pre-programmed signal provided by the second microprocessor, and used as reference for said first digital/analog converter, thereby currying out an amplitude modulation of the electric output signal.

11. The apparatus according to claim 1, wherein said channel modules Ch$_k$ for applying said electric output signal to a patient's body comprises:
a first circuit for filtering and amplifying the electric signal generated by said synthesizer module;
a second circuit feedback-adjusting the current level of the electric output signal; and
a third circuit for safety electric decoupling.

12. The apparatus according to claim 11, wherein each of said channel modules Ch$_k$, further comprises a fourth circuit for amplitude modulation of the electric output signal and said modulation is cyclically activated on only one of said one or more channel modules Ch$_k$.

13. The apparatus according to claim 1, further comprising a series resistor coupled to the one or more channels for limiting a maximum current delivered to the patient's body so as not to exceed 9 mA for safety.

14. The apparatus according to claim 1, wherein the suppression is automated to not require operator intervention by not requiring individual setting of waveform parameters or packet modulation except for stimulus amplitude to adapt said electric output signal to a sensitivity of the patient, wherein the data processing mean performs the individual setting of waveform parameters or packet modulation.

15. The apparatus according to claim 1, wherein the main module, the data, storage means, the data processing means, the synthesizer module and the means for generating are each a computer.

16. An apparatus for suppression of pain comprising:
a main modulo comprising data storage means and data processing means, said data storage means comprising:
first parameters V$_i$ corresponding uniquely to a set of sixteen different primitive waveforms S00-S15, each primitive waveform S$_i$ having a periodic and predetermined pattern over lime; and
second parameters including T-pack$_i$, Freq$_i$, and T-slot$_i$ associated with each of said different primitive waveforms S$_i$,
wherein said data processing means is adapted and configured to process a data set B$_i$ identifying a sequence consisting of a plurality of at feast two of said different primitive waveforms S$_i$ in a time sequence, each of the primitive waveforms of the sequence being processed on the basis of one or more of said second parameters T-pack$_i$, Freq$_i$, T-slot$_i$;
an electronic synthesizer module for generating an electric output signal corresponding to said sequence; and
one or more channel modules Ch$_k$ for applying said electric output signal to engage surface receptors in polymodal nerve fibers so that the electric output signal is carried by the polymodal nerve fibers us non-pain information to suppress pain.

17. The apparatus according to claim 16,
wherein said first parameter V$_i$ comprises amplitude values of each primitive waveform S$_i$ of said set of primitive waveforms S00-S15, and
wherein each of said primitive waveforms S$_i$ is represented in digital format by the corresponding first parameter V$_i$ of values, expressed in the hexadecimal system:
V$_0$=B6 FE FE FE FE FE FE FE FE FE FE FE FE FE FE FE EC DA C8 B6 A4 92 80 00 20 40 60 6E 80 80 80 80 80 80 80 80 80 80 80 80 80 80 80 80 80 80 80 80 80 80 80 80 80 80 80 80 80 80 80 80 80 80 80,
V$_1$=81 B6 FE FE FE FE FE FE FE FE FE FE FE FE FE FE FE FE FE FE FE FE FA EC DE D0 C2 B4 A6 9A 8E 00 20 40 60 6E 80 80 80 80 80 80 80 80 80 80 80 30 80 80 80 80 80 80 80 80 80 80 80 80 80 80 80 80,
V$_2$=81 AA D4 FE FE FE FE FE FE FE FE FE FE FE FE FE FE FE FE FE FE FE FE FE FE F0 E2 D4 C6 B8 AA 9C 8E 80 00 20 40 60 6E 80 80 80 80 80 80 80 80 80 80 80 80 80 80 80 80 80 80 80 80 80 80 80 80,
V$_3$=81 AA D4 FE FE FE FE FE FE FE FE FE FE FE FE FE FE FE FE FE FE FE FE FE FE FE F5 EC E3 DA D1 C8 BF B6 AD A5 9B 92 80 00 20 40 60 6E 80 80 80 80 80 80 80 80 80 80 80 80 80 80 80 80 80 80 80,
V$_4$=B6 FE FE FE FE FE FE FE FE FE FE FE FE FE FE EC DA C8 B6 A4 92 80 00 10 20 30 40 60 70 80 80 80 80 80 80 80 80 80 80 80 80 80 80 80 80 80 80 80 80 80 80 80 80 80 80 80 80 80 80 80 80 80 80,
V$_5$=81 B6 FE FE FE FE FE FE FE FE FE FE FE FE FE FE FE FE FE FE FA EC DE D0 C2 B4 A6 9A 8E 00 10 20 30 40 60 70 80 80 80 80 80 80 80 80 80 80 80 80 80 80 80 80 80 80 80 80 80 80 80 80 80 80, $V_6$=81 AA D4 FE FE FE FE FE FE FE FE FE FE FE FE FE FE FE FE FE FE FE FE FE FE FE FO E2 D4 C6 B8 AA 9C 8E 80 00 10 20 30 40 60 70 80 80 80 80 80 80 80 80 80 80 80 80 80 80 80 80 80 80 80 80 80, $V_7$=81 AA D4 FE FE FE FE FE FE FE FE FE FE FE FE FE FE FE FE FE FE FE FE FE FE FE FE F5 EC E3 DA D1 C8 BP B6 AD A5 9B 92 80 00 10 20 30 40 60 70 80 80 80 80 80 80 80 80 80 80 80 80 80 80 80, $V_8$=B6 FE FE FE FE FE FE FE FE FE FE FE FE FE FE FE EC DA C8 B6 A4 92 80 00 04 08 0C 10 16 1C 22 28 2E 34 3A 40 50 60 70 78 80 80 80 80 80 80 80 80 80 80 80 80 80 80 80 80 80 80 80 80, $V_9$=81 B6 FE FE FE FE FE FE FE FE FE FE FE FE FF FE FE FE FE FE FE FE FE EC DE Do C2 B4 A6 9A 8E 00 04 08 OC 10 16 1C 22 28 2E 34 3A 40 50 60 70 78 80 80 80 80 80 80 80 80 80 80 80 80 80 80 80 80, $V_{10}$=81 AA D4 FE FE FE FE FE FE FE FE FE FE FE FE FE FE FE FE FE FE FE FE FE FE FE FO E2 D4 C6 B8 AA 9C 8E 80 00 04 08 OC 10 16 10 22 28 2E 34 3A 40 50 60 70 78 80 80 80 80 80 80 80 80 80 80 80 80 80, $V_{11}$=81 AA D4 FE FE FE FE FE FE FE FE FE FE FE FE FE FE FE FE FE FE FE FE FE FE FE FE F5 EC E3 DA D1 C8 BF B6 AD A5 9B 92 80 00 04 08 0C 10 16 1C 22 28 2E 34 3A 40 50 60 70 78 80 80 80 80 80 80, $V_{12}$=B6 FE FE FE FE FE FE FE FE FE FE FE FE FE FE FE FE EC DA C8 B6 A4 92 89 00 05 09 0E 18 1E 20 22 28 2E 34 3A 40 49 52 5B 64 6D 77 7F 80 80 80 80 80 80 80 80 80 80 80 80 80 80 80 80 80 80 80, $V_{13}$=81 D6 FE FE FE FE FE FE EE FE FE FE FE FE FE FE FE FE FE FE FE FA EC DE D0 C2 B4 A6 9A 8E 00 05 00 0E 18 1E 20 22 28 2E 3A 40 49 52 5B 64 6D 77 7F 80 80 80 80 80 80 80 80 80 80 80, $V_{14}$=81 AA D4 FE FE FE FE FE FE FE FE FE FE FE FE FE FE FE FE FE FE FE FE FE FE FE F0 E2 D4 C6 B8 AA 9C 8E 80 00 05 09 0E 18 1E 20 22 28 2E 34 3A 40 49 52 5B 64 6D 77 7F 80 80 80 80 80 80 80 80, $V_{15}$=81 AA D4 FE FE FE FE FE FE FE FE FE FE FE FE FE FE FE FE FE FE FE FE FE FE FE FE F5 EC E3 DA D1 C8 BF B6 AD A5 9B 92 80 00 05 09 0E 18 1E 20 22 28 2E 34 3A 40 49 52 5B 64 6D 77 7F 80 80 80.

18. The apparatus according to claim 16, wherein said data storage means and said data processing means generates said data set $B_i$, in digital format, each data set $B_i$ comprising at least:
a first portion identifying a selected primitive waveform $S_i$ to be subsequently repeated at least twice in said sequence, forming a packet $Pack_i$:
a second portion identifying a frequency value $Freq_i$ to be associated with said selected primitive waveform $S_i$ in sequence; and
a third portion identifying a first lime duration value $T\text{-}slot_i$ to be associated with a pause interval, subsequent to said packet $Pack_i$ and wherein said data storage and processing means further calculate a second time duration value $T\text{-}pack_i$ to be associated with the duration of said packet $Pack_i$.

19. The apparatus according to claim 16,
wherein said data storage means includes a first probabilistic criterion and said data processing means selects the waveforms $S_i$ with which to compose the sequence on the basis of the first probabilistic criterion, and
wherein said first probabilistic criterion emails the selection of the waveforms $S_i$ depending on a specific probability, wherein the specific probability varies dynamically for each new packet generated.

20. The apparatus according to claim 16, wherein said data processing means calculates said second parameters $T\text{-}pack_i$, $Freq_i$, $T\text{-}slot_i$ for each waveform $S_i$ comprised in sequence on the basis of a probabilistic criteria stored in the data storage means, from set values and wherein said probabilistic criteria for calculating said second parameters $T\text{-}pack_i$, $Freq_i$, $T\text{-}slot_i$ are dynamically modified according to probabilistic filters based on corresponding rules set in advance and stored in the data storage means to vary the selection probability of said set values.

21. The apparatus according to claim 16, wherein said main module processes each data set $B_i$ is available as input for said synthesizer module and each data set $B_i$ is represented by a byte.

22. The apparatus according to claim 16, wherein said synthesizer module comprises a microprocessor adapted and configured to read the data set $B_i$ provided by said main module and a first digital/analog converter adapted and configured to convert the electric output signal generated by said second microprocessor into an analog signal corresponding to said sequence, wherein said synthesizer module further comprises a second digital/analog converter adapted and configured to produce a modulating signal based on a pre-programmed signal provided by the second microprocessor, and used as reference for said first digital/analog converter, thereby carrying out an amplitude modulation of the electric output signal, wherein the main module, the data storage means, the data processing means, the synthesizer module and the means for generating are each a computer.

23. The apparatus according to claim 16, wherein said channel modules $Ch_k$ for applying said electric output signal to a patient's body comprises;
a first circuit for filtering and amplifying the electric signal generated by said synthesizer module;
a second circuit feedback-adjusting the current level of the electric output signal; and
a third circuit for safety electric decoupling,
wherein each of said channel modules $Ch_k$, further comprises a fourth circuit for amplitude modulation of the electric output signal and said modulation is cyclically activated on only one of said one or more channel modules $Ch_k$ and
further comprising a series resistor coupled to the one or more channels for limiting a maximum current delivered to the patient's body so as not to exceed 9 mA for safety, wherein the suppression is automated to not require operator intervention by not requiring individual setting of waveform parameters or packet modulation except for stimulus amplitude to adapt said electric output signal to a sensitivity of the patient, wherein the data processing mean performs the individual setting of waveform parameters or packet modulation.

24. An apparatus for suppression of pain comprising:
a) a main module including data storage and a microprocessor in communication with the data storage,
wherein the data storage includes:
first parameters $V_i$ corresponding uniquely to a set of sixteen different primitive waveforms S00-S15, each primitive waveform $S_i$ having a periodic and predetermined pattern overtime; and
second parameters including $T\text{-}pack_i$, $Freq_i$, and $T\text{-}slot_i$ associated with each of the different primitive waveforms $S_i$,
wherein the microprocessor is adapted and configured to process a data set $B_i$ identifying a sequence consisting of a plurality of at least two of the different primitive waveforms $S_i$ in a time sequence, each of the primitive waveforms of the sequence being processed on the basis of one or more of said second parameters T-pack$_i$, Freq$_i$, T-slot$_i$;

b) an electronic synthesizer module for generating an electric output signal corresponding to the sequence; and c) at least one channel module Ch$_k$ for applying the electric output signal to engage surface receptors in polymodal nerve fibers so that the electric output signal is carried by the polymodal nerve fibers as non-pain information to suppress pain.

25. The apparatus according to claim 24, wherein said main module generates said data set B$_i$, in digital format, each data set B$_i$ comprising at least:

a first portion identifying a selected primitive waveform S$_i$ to be subsequently repealed at least twice in said sequence, forming a packet Pack$_i$;

a second portion identifying a frequency value Freq$_i$ to be associated with said selected primitive waveform S$_i$ in sequence; and a third portion identifying a first time duration value T-slot$_i$ to be associated with a pause interval, subsequent to said packet Pack$_i$ and wherein said data storage and microprocessor further calculate a second time duration value T-pack$_i$ to be associated with the duration of said packet Pack$_i$.

26. The apparatus according to claim 24, wherein said data storage includes a first probabilistic criterion and said microprocessor selects the waveforms S$_i$ with which to compose the sequence on the basis of the first probabilistic criterion, and wherein, said first probabilistic criterion entails the selection of the waveforms S$_i$ depending on a specific probability, wherein the specific probability varies dynamically for each new packet generated.

27. The apparatus according to claim 24, wherein said microprocessor calculates said second parameters T-pack$_i$, Freq$_i$, T-slot$_i$ for each waveform S$_i$ comprised in sequence on the basis of a probabilistic criteria stored in the data storage, from set values and wherein said probabilistic criteria for calculating said second parameters T-pack$_i$, Freq$_i$, T-slot$_i$, are dynamically modified according to probabilistic fillers based on corresponding rules set in advance and stored in the data storage to vary the selection probability of said set values.

28. The apparatus according to claim 24, wherein said synthesizer module comprise a microprocessor adapted and configured to read the data set B$_i$ provided by said main module and a first digital/analog converter adapted and configured to convert the electric output signal generated by said second microprocessor into an analog signal corresponding to said sequence, wherein said synthesizer module further comprises a second digital/analog converter adapted and configured to produce a modulating signal based on a pre-programmed signal provided by the second microprocessor, and used as reference for said first digital/analog converter, thereby carrying out an amplitude modulation of the electric output signal.

29. The apparatus according to claim 24, wherein said channel modules Ch$_k$ for applying said electric output signal to a patient's body comprises:

a first circuit for filtering and amplifying the electric signal generated by said synthesizer module;

a second circuit feedback-adjusting the current level of the electric output signal; and a third circuit for safety electric decoupling, wherein each of said channel modules Ch$_k$, further comprises a fourth circuit for amplitude modulation of the electric output signal and said modulation is cyclically activated on only one of said one or more channel modules Ch$_k$ and further comprising a series resistor coupled to the one or more channels for limiting a maximum current delivered to the patient's body so as not to exceed 9 mA for safety, wherein the suppression is automated to not require operator intervention by not requiring individual setting of waveform parameters or packet modulation except for stimulus amplitude to adapt said electric output signal to a sensitivity of the patient, wherein the data processing mean performs the individual setting of waveform parameters or packet modulation.

* * * * *